(12) United States Patent
Acharjee

(10) Patent No.: US 9,926,352 B2
(45) Date of Patent: Mar. 27, 2018

(54) CHIMERIC DYSTROPHIN-VSV-G PROTEIN TO TREAT DYSTROPHINOPATHIES

(71) Applicant: Sujata Acharjee, New York, NY (US)

(72) Inventor: Sujata Acharjee, New York, NY (US)

(73) Assignee: SERENDIPITY BIOTECH INC., New York, NY (US)

( * ) Notice: Subject to any disclaimer, the term of this patent is extended or adjusted under 35 U.S.C. 154(b) by 0 days.

(21) Appl. No.: 14/635,012

(22) Filed: Mar. 2, 2015

(65) Prior Publication Data

US 2015/0246950 A1      Sep. 3, 2015

Related U.S. Application Data

(60) Provisional application No. 61/946,961, filed on Mar. 3, 2014.

(51) Int. Cl.
   *A61K 38/00* (2006.01)
   *C07K 14/47* (2006.01)
   *C07K 7/06* (2006.01)

(52) U.S. Cl.
   CPC .......... *C07K 14/4708* (2013.01); *A61K 38/00* (2013.01); *C07K 7/06* (2013.01); *C07K 2319/10* (2013.01); *C07K 2319/50* (2013.01)

(58) Field of Classification Search
   None
   See application file for complete search history.

(56) References Cited

U.S. PATENT DOCUMENTS

| 2003/0148521 | A1 | 8/2003 | Bell et al. | |
| 2003/0211590 | A1 | 11/2003 | Hwu | |
| 2003/0219402 | A1* | 11/2003 | Rutter | 424/85.1 |
| 2006/0078542 | A1 | 4/2006 | Mah et al. | |
| 2007/0286856 | A1* | 12/2007 | Brown et al. | 424/133.1 |
| 2009/0041724 | A1 | 2/2009 | Jensen | |
| 2012/0322147 | A1 | 12/2012 | Mangeot et al. | |

FOREIGN PATENT DOCUMENTS

| EP | 2684892 | 1/2014 |
| WO | WO 2008/124646 | * 10/2008 |
| WO | WO 2010040023 | 4/2010 |
| WO | WO 2011161260 | 12/2011 |

OTHER PUBLICATIONS

Chen et al, Design of an in vivo cleavable disulfide linker in recombinant fusion proteins, Biotechniques. Jul. 2010;49(1):513-8.*
Saito et al (Oncogene (2008) 27, 1821-1833).*
Widera et al (Pharm Res. Feb. 2004;21(2):278-84).*
Bartz et al (Methods, Aug. 1997;12(4):337-42).*
Peng et al (Gene Therapy (1999) 6, 1552-1557).*
Dahiya et al (J Immunol 2011; 187:2723-2731).*
Albright et al (Mol Cancer Ther. May 2005;4(5):751-60).*
GenBank CAA24523.1 (downloaded on Aug. 3, 2017 from URL:< https://www.ncbi.nlm.nih.gov/protein/61831?report=genbank &log$=protalign&blast_rank=1&RID=S6600YT301R>).*
Kohli et al. (Cancer Investigation, 2011, 29:1, 62-67).*
Sonnemann KJ, Heun-Johnson H, Turner AJ, Baltgalvis KA, Lowe DA, Ervasti JM. Functional substitution by TAT-utrophin in dystrophin-deficient mice. PLoS Med. 2009.
Ahn, Andrew H.; Kunkel, Louis M.; Syntrophin binds to an alternatively spliced exon of dystrophin. The Journal of Cell Biology. 1995;128(3):363-371.
Amenta AR, Yilmaz A, Bogdanovich S, et al. Biglycan recruits utrophin to the sarcolemma and counters dystrophic pathology in mdx mice. Proceedings of the National Academy of Sciences of the United States of America. 2011;108(2):762-767.
Weisbart, Richard H. et al.; An intracellular delivery vehicle for protein transduction of micro-dystrophin. Journal of Drug Targeting. vol. 13, Iss. 2, 2005, 81-87.
Bies RD, Phelps SF, Cortez MD, Roberts R, Caskey CT, Chamberlain JS. Human and murine dystrophin mRNA transcripts are differentially expressed during skeletal muscle, heart, and brain development. Nucleic Acids Research. 1992;20(7):1725-1731.
Blau HM, Webster C, Pavlath GK. Defective myoblasts identified in Duchenne muscular dystrophy. Proceedings of the National Academy of Sciences of the United States of America. 1983;80(15):4856-4860.
Briggs D, Morgan JE. Recent progress in satellite cell/myoblast engraftment—relevance for therapy. The Febs Journal. 2013;280(17):4281-4293.
Crosbie, Rachelle H. Sarcospan, the 25-kDa Transmembrane Component of the Dystrophin-Glycoprotein Complex. J. Biol. Chem. 1997 272: 31221-31224.
Danialou, Gawiyou. Dystrophin-deficient cardiomyocytes are abnormally vulnerable to mechanical stress-induced contractile failure and injury. FASEB J Jul. 15, 2001:1655-1657; published ahead of print May 29, 2001.
Darras BT, Miller DT, Urion DK. Dystrophinopathies. Sep. 5, 2000 [Updated Nov. 26, 2014]. In: Pagon RA, Adam MP, Ardinger HH, et al., editors. GeneReviews® [Internet]. Seattle (WA): University of Washington, Seattle; 1993-2015. Available from: http://www.ncbi.nlm.nih.gov/books/NBK1119/.
Delfin DA, Zang KE, Schill KE, et al. Cardiomyopathy in the dystrophin/utrophin-deficient mouse model of severe muscular dystrophy is characterized by dysregulation of matrix metalloproteinases. Neuromuscular disorders: NMD. 2012;22(11):1006-1014. doi:10.1016/j.nmd.2012.05.002.

(Continued)

*Primary Examiner* — Jennifer Pitrak McDonald
*Assistant Examiner* — Sergio Coffa
(74) *Attorney, Agent, or Firm* — Wiggin and Dana LLP; Gregory S. Rosenblatt; Andrew D. Bochner

(57) ABSTRACT

A chimeric protein that is a fusion construct of a series of functional domains is used to deliver a therapeutic agent to a human subject suffering from disease. In some embodiments, the chimeric protein includes a therapeutic region, a transportation region, and a cleavage region disposed between the therapeutic region and the transportation region. The transportation region allows the chimeric protein to be moved across a cellular membrane of an affected cell within the subject. Cleavage of the chimeric protein at the cleavage region once within the cell separates the therapeutic region from the transportation region, enabling the therapeutic region to function normally within the cell. The therapeutic region can be effective in the treatment of, for example, muscular dystrophy, diastrophic dysplasia, malignant melanoma, porphyria, alpha-1 antitrypsin deficiency, Aicardi-Goutieres syndrome, cystic fibrosis, progeria, Marfan syndrome, tuberous sclerosis, adrenoleukodystrophy, and the like.

7 Claims, 8 Drawing Sheets

(56) References Cited

OTHER PUBLICATIONS

De Luca A. Pre-clinical drug tests in the mdx mouse as a model of dystrophinopathies: an overview. Acta Myologica. 2012;31(1):40-47.
Den Dunnen JT, Grootscholten PM, Bakker E, et al. Topography of the Duchenne muscular dystrophy (DMD) gene: FIGE and cDNA analysis of 194 cases reveals 115 deletions and 13 duplications. American Journal of Human Genetics. 1989;45(6):835-847.
"Dystrophin protein—Protein—NCBI", http://www.ncbi.nlm.nih.gov/protein/Q14205, printed May 28, 2015.
Epstein, Wallace V. Treatment of Rheumatoid Arthritis with a Tumor Necrosis Factor Receptor-Fc Fusion Protein. The New England Journal of Medicine. 337(21):1559-1560.
Vessillier, Sandrine et al. Latent cytokines: development of novel cleavage sites and kinetic analysis of their differential sensitivity to MMP-1 and MMP-3. Protein Engineering, Design and Selection (2004) 17 (12): 829-835.
Chen X, Zaro J, Shen W-C. Fusion Protein Linkers: Property, Design and Functionality. Advanced drug delivery reviews. 2013;65(10):1357-1369.
Kanda, Teru et al. Histone—GFP fusion protein enables sensitive analysis of chromosome dynamics in living mammalian cells. Current Biology, vol. 8, Issue 7, 377-385.Kanda, Teru et al. Histone—GFP fusion protein enables sensitive analysis of chromosome dynamics in living mammalian cells. Current Biology, vol. 8, Issue 7, 377-385.
Vesicular stomatitis Indiana virus, http://www.uniprot.org/uniprot/P04884.txt?version=71, printed May 28, 2015.
Invitation to Pay Additional Fees from International Patent Application No. PCT/US2015/027496 dated Aug. 13, 2015.
International Search Report and Written Opinion from International Patent Application No. PCT/US2015/018263, dated Sep. 14, 2015.
Randall J. Owens et al., "Mutations in the membrane-spanning domain of the human immunodeficiency virus envelope glycoprotein that affect fusion activity," Journal of Virology, Jan. 1, 1994, pp. 570-574, vol. 68 No. 1, U.S.
Hsin-Lung Lo et al., "Production of vesicular stomatitis virus G glycoprotein (VSV-G) pseudotyped retroviral vectors," Current Protocols in Human Genetics, Jan. 1, 2007, Chapter 12.
Rahkila Paavo et al., "Protein Targeting to the Plasma Membrane of Adult Skeletal Muscle Fiber: An Organized Mosaic of Functional Domains," Experimental Cell Research, Jul. 1, 2001, pp. 61-72, vol. 267 No. 1, Amsterdam, Netherlands.
R.H. Weisbart et al., "An intracellular delivery vehicle for protein transduction of micro-dystrophin," Journal of Drug Targeting, Feb. 1, 2005, pp. 81-87, vol. 13 No. 2, Taylor & Francis.
Supplementary European Search Report, dated Jul. 7, 2017, prepared for related EP Application 15758031.7, 15 pages.
Kyle Chamberlain et al, Expressing Transgenes That Exceed the Packaging Capacity of Adeno-Associated Virus Capsids, Human Gene Therapy Methods, Feb. 1, 2016, pp. 1-12, vol. 27 Issue 1, Mary Ann Liebert, Inc.

* cited by examiner

CHIMERIC DYSTROPHIN-VSV-G PROTEIN TO TREAT DYSTROPHINOPATHIES

CROSS-REFERENCE TO RELATED APPLICATIONS

This application claims the benefit of U.S. Provisional No. 61/946,961, filed Mar. 3, 2014, which is incorporated herein by reference in its entirety.

FIELD OF THE DISCLOSURE

Disclosed is a chimeric or fusion protein including a therapeutic construct that is designed for use in the treatment of human subjects suffering from diseases such as muscular dystrophy, diastrophic dysplasia, malignant melanoma, porphyria, alpha-1 antitrypsin deficiency, Aicardi-Goutieres syndrome, cystic fibrosis, progeria, Marfan syndrome, tuberous sclerosis, adrenoleukodystrophy, and the like.

BACKGROUND OF THE DISCLOSURE

The Dystrophin Glycoprotein complex (DGC) is a very crucial structural component of skeletal and cardiac muscles. It is comprised of dystrophin and a plurality of proteins associated with it and imparts structural stability to the muscle membrane. The physical interactions between the proteins of the DGC form the basis for mechanical linking of the outside of the membrane to the inside and play an important role in mediating biological signaling process. These proteins form an intricate network which stabilizes the membrane as it contracts and relaxes. These interactions are essential in maintaining the structural integrity of the muscle membrane. Lack of any of these components owing to mutation compromises the structural stability leading to muscle damage.

Dystrophin was originally identified through its deficiency in the lethal neuromuscular disorder, Duchenne Muscular Dystrophy (DMD). Skeletal and cardiac muscles that lack functional full-length dystrophin protein are extremely susceptible to tear and damage from the contraction-relaxation activity. In the heart, aortic banding experiments performed on the dystrophin-deficient mdx mouse similarly result in accelerated cardiac damage. These studies demonstrated the essential role of dystrophin and the DGC in protecting the plasma membrane against contraction-induced damage.

The absence of dystrophin in DMD patients leaves the muscle membrane fragile and susceptible to damage upon contraction, leading to destruction of the DGC with loss of mechanical stability and proper mechano-transduction signaling. The dystrophin deficient myofibers undergo repeated rounds of contraction mediated injury with consequent myofiber necrosis that ultimately results in the replacement of myofibers by fibrous and fat tissue; a progressive degeneration and failure of regeneration efficiency also occurs owing to the continuous depletion of muscle precursor cells or satellite cells and their incapability to proliferate, multiply, and differentiate.

Dystrophin has four functional domains: a calponin-like actin binding domain at the amino terminal, a central rod domain of 24 spectrin-like repeats, a cysteine-rich region at the carboxy terminal, and an extreme helical carboxy terminal region. The amino terminal actin binding domain is responsible for anchoring dystrophin to cytoskeletal filamentous actin. Within the central rod domain, spectrin repeats 11 through 17 constitute a second site for binding actin. The cysteine rich region interacts with the intracellular portion of the transmembrane protein beta-dystroglycan and anchors dystrophin to the sarcolemma. The extreme carboxyl-terminal mediates its interaction with syntrophins.

The human dystrophin gene is the largest gene characterized so far. It contains 79 exons, several splicing sites and a number of tissue specific promoters that result in a range of transcripts which form amino terminal truncated dystrophin proteins of varying lengths. Dystrophin is a huge gene with an open reading frame that is 11058 nucleotides long, making it a difficult target to work with. The large size of the dystrophin gene is also responsible for its high frequency of spontaneous mutation, with most of the mutations being deletions. The extent of severity caused by these mutations varies depending on the kind of deletion. Where a deletion results in complete absence of dystrophin protein due to disruption of the reading frame of the gene, severe forms of muscular dystrophy or DMD can occur. Deletions which lead to the formation of truncated proteins result in milder forms of muscular dystrophy such as Becker Muscular Dystrophy. One deletion which removes a central part of dystrophin protein encompassing 5,106 base pairs, almost half the coding sequence, has been reported to cause a very mild form of muscular dystrophy with patients being ambulant even at the age of 61.

Dystrophin gene is one of the first genes identified by reverse genetics. DMD is an X-linked muscular dystrophy with an incidence of one in 3500 young males. DMD is one of the most common hereditary diseases known. The onset can be between the age of 3 to 5 yrs. and depending on the severity of the disease the affected males become non-ambulatory by the age of 13. The other clinical features include scoliosis, muscle weakness and damage, muscle hypertrophy, cardiomyopathy, mental retardation and very high serum creatine kinase levels. This disease ultimately causes death between the ages of 15 to 25 years. The most common cause of death in these patients is respiratory or cardiac failure. Tens of thousands of individuals are living with DMD in the United States, Europe, Australia, Canada, Israel, and Japan alone.

DMD has also been reported in a number of animals including mouse, cats and dogs. Mdx mice that have a premature stop codon mutation on exon 23 of the dystrophin gene, leading to a lack of the mature protein, have long been used as an animal model to study the pathogenesis of the disease. The absence of dystrophin results in an acute onset of skeletal muscle necrosis around 3 weeks of post-natal life, followed by an extensive period of degeneration and regeneration until necrosis gradually decreases and a relatively low level is reached in adult mice (3-4 months) with pathology stabilization. However, the pathology is far more benign than in DMD.

Vesicular Stomatitis Viruses have long been known to cause a number of diseases in humans, such as rabies. These viruses enter their hosts by making an envelope of proteins around them also known as VSV-G glycoproteins which facilitate the fusion of viral membrane with the host cell membrane. VSV-G has been widely used as a tool for gene transfer by pseudo typing viral vectors with VSV-G envelope. Recently it has been shown that LDL receptors present in the membrane of mammalian cells serve as a receptor for the VSV-G proteins and port of entry for the vesicular stomatitis viruses. This probably justifies the pantropic nature of vesicular stomatitis viruses as the LDL receptors are present in a wide range of mammalian cells and tissues.

DMD therapies that are currently being developed include DNA- and cell-based therapies, as well as drugs which aim to modulate cellular pathways or gene expression. Attempts have been made to restore the expression of full-length functional protein or short truncated protein either via exon-skipping, gene therapy, stem cells, or small molecules to induce read-through of premature stop-codon mutations. Other promising approaches include small molecules or recombinant proteins to enhance the dystrophin surrogate utrophin, and stabilize or reduce degradation of DGC.

Although the approaches previously used are promising, alternative strategies need to be developed because of the limitations of these approaches, e.g. oligonucleotides used for exon-skipping could not be effectively delivered to all the non-skeletal target muscle tissues such as heart; ataluren aimed to induce read-through of premature stop codons in dystrophin gene could only be used for a patient subpopulation exhibiting mutations displaying premature stop codons; ataluren was not potent enough to show any significant effect during clinical trials on patients treated with the drug. Currently there is no treatment available for DMD and current therapies rely in delaying the progression of the disease by clinically using Prednisone and supportive care with a mean life expectancy in the thirties.

What is desired therefore is a simple yet effective system and method for treating patients with DMD. What is also desired is a singular system and method that allows for treatment of multiple types of dystrophinopathy across a plurality of patient types, resulting in increasing or maintaining the structural integrity of the muscle fiber, limiting muscle damage, and improved muscle strength.

BRIEF SUMMARY

Disclosed herein is a system and method to alleviate the symptoms associated with certain conditions by delivering chimeric proteins in patients exhibiting symptoms of those conditions.

In some embodiments, the system includes a chimeric protein comprising a therapeutic region, a transportation region, and a cleavage region disposed between the therapeutic region and the transportation region, wherein the transportation region allows for transport of the chimeric protein across a cellular membrane. In some embodiments, the cleavage region is disposed at the N-terminal end of the therapeutic region. In some embodiments, the cleavage region is disposed at the C-terminal end of the therapeutic region. In some embodiments, the therapeutic region is selected from the group consisting of: a full-length dystrophin, a truncated dystrophin, and combinations thereof.

In some embodiments, the transportation region is selected from the group consisting of: a vesicular stomatitis virus G and functional variants of a vesicular stomatitis virus G. In some embodiments, the vesicular stomatitis virus G variants allow for up to at least 4 amino acid substitutions. In some embodiments, the vesicular stomatitis virus G variants has at least a sequence identity with a wild-type vesicular stomatitis virus G selected from the group consisting of: at least 90%, at least 95%, at least 96%, at least 97%, at least 98%, or at least 99% sequence identity.

In some embodiments, the cleavage region is configured to be cleaved subsequent to transport of the chimeric protein across the cellular membrane. In some embodiments, the cleavage region is a cleavage site for a membrane metalloprotease. In some embodiments, the cleavage region comprises the amino acid sequence PLGLWAL (SEQ ID NO: 9), characterized in that each amino acid may be conservatively substituted. In some embodiments, the cleavage region comprises the amino acid sequence P-X-X-Hy-(S/T), characterized in that P identifies proline, X is any residue, Hy is a hydrophobic residue, and S/T may either serine or threonine.

In some embodiments, at least a portion of a sequence of the chimeric protein is selected from the group consisting of: SEQ. ID NO.: 1, SEQ. ID NO.: 2, SEQ. ID NO.: 3, SEQ. ID NO.: 4, SEQ. ID NO.: 5, SEQ. ID NO.: 6, SEQ. ID NO.: 7, SEQ. ID NO.: 8, and pharmacologically acceptable equivalents thereof.

In some embodiments, the present disclosure is directed to a method of treating a subject having a medical condition comprising the steps of preparing a therapeutic dose of a chimeric protein comprising a therapeutic region, a transportation region, and a cleavage region disposed between the therapeutic region and the transportation region wherein the transportation region allows for transport of the chimeric protein across a cellular membrane, and administering the therapeutic dose to the subject. In some embodiments, the medical condition includes a muscular dystrophy, diastrophic dysplasia, malignant melanoma, porphyria, alpha-1 antitrypsin deficiency, Aicardi-Goutieres syndrome, cystic fibrosis, progeria, Marfan syndrome, tuberous sclerosis, adrenoleukodystrophy, and the like. In some embodiments, the nucleotide sequence of the therapeutic region comprises a sequence selected from the group consisting of: SEQ. ID NO.: 1, SEQ. ID NO.: 3, SEQ. ID NO.: 5, and SEQ. ID NO.: 7. In some embodiments, the amino acid sequence of the therapeutic region comprises a sequence selected from the group consisting of: SEQ. ID NO.: 2, SEQ. ID NO.: 4, SEQ. ID NO.: 6, and SEQ. ID NO.: 8.

In some embodiments, the present disclosure is directed to a method of making a chimeric protein for use in the treatment of a condition, the method comprising the steps of cloning a nucleotide sequence into a vector, the nucleotide sequence coding for a chimeric protein comprising a therapeutic region, a transportation region, and a cleavage region disposed between the therapeutic region and the transportation region wherein the transportation region allows for transport of the chimeric protein across a cellular membrane, transfecting the vector into a host cell, proliferating the host cell, and isolating the chimeric protein from the host cell. In some embodiments, the nucleotide sequence of the therapeutic region comprises a sequence selected from the group consisting of: SEQ. ID NO.: 1, SEQ. ID NO.: 3, SEQ. ID NO.: 5, and SEQ. ID NO.: 7. In some embodiments, the nucleotide sequence coding for the therapeutic region codes for a protein selected from the group consisting of: a full-length dystrophin, a truncated dystrophin, and combinations thereof.

In some embodiments of the method of making a chimeric protein for use in the treatment of a condition, the nucleotide sequence coding for the transportation region codes for a protein selected from the group consisting of: a vesicular stomatitis virus G and functional variants of a vesicular stomatitis virus G. In some embodiments of the method of making a chimeric protein for use in the treatment of a condition, the nucleotide sequence coding for the cleavage region codes for a membrane metalloprotease. In some embodiments of the method of making a chimeric protein for use in the treatment of a condition, the medical condition includes a muscular dystrophy, diastrophic dysplasia, malignant melanoma, porphyria, alpha-1 antitrypsin deficiency, Aicardi-Goutieres syndrome, cystic fibrosis, progeria, Marfan syndrome, tuberous sclerosis, adrenoleukodystrophy, and the like. In some embodiments of the method of making a chimeric protein for use in the treatment of a condition, the step of isolating the chimeric protein from the host cell includes the step of isolating the chimeric protein from a lysate of the host cell.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention will be apparent from the following detailed description taken in conjunction with the accompanying drawings.

DETAILED DESCRIPTION

Figure 1:
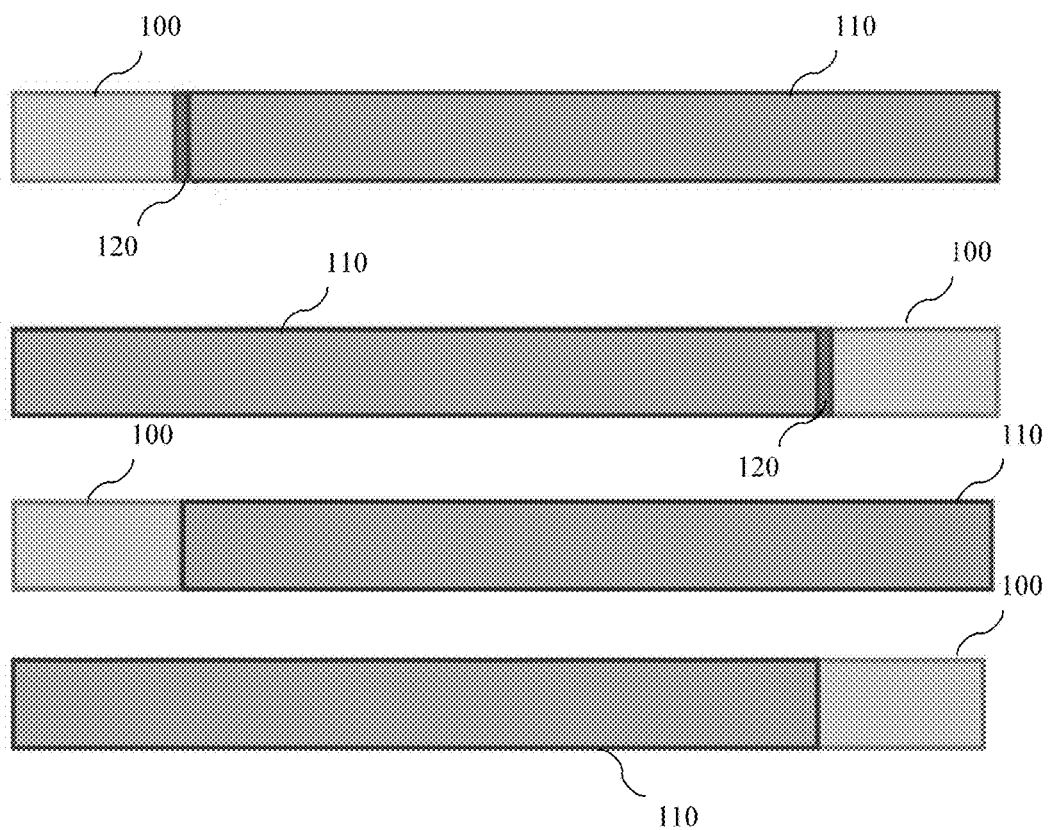
FIG. 1 shows a schematic view of a chimeric protein for the treatment of dystrophinopathies consistent with some embodiments of the present disclosure.

The embodiments disclosed by the invention are only examples of the many possible advantageous uses and implementations of the innovative teachings presented herein. In general, statements made in the specification of the present application do not necessarily limit any of the various claimed inventions. Moreover, some statements may apply to some inventive features but not to others. In general, unless otherwise indicated, singular elements may be in plural and vice versa with no loss of generality. In the drawings, like numerals refer to like parts through several views.

FIG. 1 shows a schematic diagram of a chimeric protein consistent with some embodiments of the present disclosure. In some embodiments, a transportation region is fused to the N-terminal end of a therapeutic region. In some embodiments, the transportation region is fused to the C-terminal end of the therapeutic region. In some embodiments, a cleavage region is disposed between the therapeutic region and the transportation region. As used herein, the term "transportation regions" may also be interchangeably referred to as "delivery mechanisms" or "carriers". In some embodiments, the transportation region is VSV-G. In some embodiments, the therapeutic region is a full length dystrophin protein. In some embodiments, the therapeutic region is a truncated dystrophin protein. In some embodiments, the cleavage region is a cleavage site for membrane metalloproteases.

In some embodiments, the chimeric protein of the present disclosure has a nucleotide sequence wherein at least a portion of the sequence is selected from the group consisting of: SEQ. ID NO.: 1, SEQ. ID NO.: 3, SEQ. ID NO.: 5, SEQ. ID NO.: 7, and pharmacologically acceptable equivalents thereof. In some embodiments, the chimeric protein of the present disclosure has an amino acid sequence wherein at least a portion of the sequence is selected from the group consisting of: SEQ. ID NO.: 2, SEQ. ID NO.: 4, SEQ. ID NO.: 6, SEQ. ID NO.: 8, and pharmacologically acceptable equivalents thereof. In some embodiments, the sequence for the chimeric protein has at least 90%, at least 95%, at least 96%, at least 97%, at least 98%, or at least 99% sequence identity with at least one of SEQ. ID NO.: 1, SEQ. ID NO.: 2, SEQ. ID NO.: 3, SEQ. ID NO.: 4, SEQ. ID NO.: 5, SEQ. ID NO.: 6, SEQ. ID NO.: 7, SEQ. ID NO.: 8. In some embodiments, any suitable mutations, substitutions, additions, and deletions may be made to the chimeric protein so long as the pharmacological activity of the resulting variant chimeric protein is retained.

SEQ. ID NO.: 1 is a nucleotide sequence of a dystrophin-VSV-G chimeric protein, with the VSV-G at the N-terminus, consistent with some embodiments of the present invention.

SEQ. ID NO.: 2 is an amino acid sequence of a dystrophin-VSV-G chimeric protein, with the VSV-G at the N-terminus, consistent with some embodiments of the present invention.

SEQ. ID NO.: 3 is a nucleotide sequence of a truncated dystrophin-VSV-G chimeric protein, with the VSV-G at the N-terminus, consistent with some embodiments of the present invention.

SEQ. ID NO.: 4 is an amino acid sequence of a truncated dystrophin-VSV-G chimeric protein, with the VSV-G at the N-terminus, consistent with some embodiments of the present invention.

SEQ. ID NO.: 5 is a nucleotide sequence of a dystrophin-VSV-G chimeric protein, with the VSV-G at the C-terminus, consistent with some embodiments of the present invention.

SEQ. ID NO.: 6 is an amino acid sequence of a dystrophin-VSV-G chimeric protein, with the VSV-G at the C-terminus, consistent with some embodiments of the present invention.

SEQ. ID NO.: 7 is a nucleotide sequence of a truncated dystrophin-VSV-G chimeric protein, with the VSV-G at the C-terminus, consistent with some embodiments of the present invention.

SEQ. ID NO.: 8 is an amino acid sequence of a truncated dystrophin-VSV-G chimeric protein, with the VSV-G at the C-terminus, consistent with some embodiments of the present invention.

Recombinant and chimeric proteins have been available in the market as therapies for various conditions and have proven to be extremely potent in curing diseases such as arthritis. In some embodiments, the present disclosure is directed to a dystrophin (or functional mutant or truncated form of dystrophin) protein fused either at the N-terminal or C-terminal with a VSV-G (or variants of VSV-G) protein with or without a short linker between the two proteins, which will be a cleavage site for membrane metalloproteases (MMPs). This therapy will rely on administering biologically effective amounts of recombinant dystrophin protein that will be transduced in different muscle tissues and ameliorate the pathologies associated with the lack of dystrophin. The therapy will allow the subject to compensate for the lack of certain functional protein production.

In some embodiments, VSV-G protein serves as the transportation region or carrier for delivering the dystrophin protein to various tissues. LDL receptors, through which VSV-G establishes initial contact to enter the cells, are present in a wide range of tissues. Therefore, this approach mitigates the issues related to the delivery of dystrophin protein at different target sites found in previous approaches. In some embodiments, the VSV-G used in the chimeric protein of the instant application is a wild-type VSV-G. In some embodiments, the VSV-G is a variant of wild-type VSV-G. Any suitable mutations, substitutions, additions, and deletions may be made to the VSV-G so long as the cellular membrane transport activity of the resulting variant VSV-G is retained. In some embodiments, suitable VSV-G variants include the thermostable and serum resistant mutants of VSV-G, which include the following point mutations to wild-type VSV-G: S162T, T230N, T368A, or combined mutants T230N+T368A, or K66T+S162T+T230N+T368A. In some embodiments, variant VSV-G has at least 90%, at least 95%, at least 96%, at least 97%, at least 98%, or at least 99% sequence identity with wild-type VSV-G.

Sometimes fusing a protein with another protein interferes with the function of the proteins and leads to a decrease in their biological activity. In order to overcome this problem, in some embodiments, a cleavage region including a cleavage site for MMPs is provided. In some embodiments, a cleavable linker is disposed between the dystrophin and VSV-G. In such an embodiment, dystrophin will only be released from the chimeric construct with VSV-G when it is cleaved by MMPs. MMPs are overexpressed during various pathologic conditions and inflammation, including muscular dystrophy. Therefore, when the chimeric dystrophin-VSV-G protein reaches the sites of inflammation upon delivery, the MMPs cleave the chimeric protein and release the dystrophin protein for incorporation into the muscle cells and treatment of the subject's dystrophinopathy. In some embodiments, the MMP cleavage site encodes for amino acids PLGLWAL (SEQ ID NO: 9), which is a known putative cleavage site for all the MMPs. In some embodiments, the MMP cleavage site comprises a sequence defined by the amino acids P-X-X-Hy-(S/T), characterized in that P identifies proline, X is any residue, Hy is a hydrophobic residue, and S/T may either serine or threonine. In some embodiments, the MMP cleavage site is selected from the sequences PLGLWAL (SEQ ID NO: 9), P-X-X-Hy-(S/T), and variants and mutations thereof In some embodiments, the cleavage site is eliminated.

This strategy can also be extended to other conditions which are caused by a lack of a single protein by replacing dystrophin with the protein of interest for the respective conditions. In some embodiments, the dystrophin is replaced by another therapeutic construct. In these embodiments, the therapeutic construct would be selected to treat the pathological conditions of other diseases, such as diastrophic dysplasia, malignant melanoma, porphyria, alpha-1 antitrypsin deficiency, Aicardi-Goutieres syndrome, cystic fibrosis, progeria, Marfan syndrome, tuberous sclerosis, adrenoleukodystrophy, and the like. In some embodiments, other proteins may be fused to the N- and C-termini of the proteins included in the chimeric protein. Table 1 below portrays various conditions that may be effectively treated using the chimeric proteins of the present disclosure, as well as the therapeutic constructs that may, in some embodiments, be substituted for dystrophin.

TABLE 1

Therapeutic constructs for incorporation into the chimeric protein of the present disclosure for use in the treatment of various conditions.

| Condition | Therapeutic Construct |
|---|---|
| diastrophic dysplasia | SLC26A2. A transmembrane glycoprotein which is a sulfate transporter and a member of the solute family. |
| malignant melanoma | p16(INK4a) and the p14(ARF); proteins encoded by the CDKN2A and PTEN genes. |
| porphyria | Delta-aminolevulinate dehydratase; 5-aminolevulinate synthase 2; coproporphyrinogen oxidase; ferrochelatase; hydroxymethylbilane synthase; protoporphyrinogen oxidase; uroporphyrinogen decarboxylase; uroporphyrinogen III synthase. Proteins encoded by the ALAD, ALAS2, CPOX, FECH, HMBS, PPOX, UROD, or UROS genes. |
| alpha-1 antitrypsin deficiency | Alpha-1 antitrypsin. A plasma protein and serine protease inhibitor. |
| Aicardi-Goutieres syndrome | Proteins encoded by the TREX1, RNASEH2A, RNASEH2B, and RNASEH2C genes. Mutations in these genes may result in absent or dysfunctional nuclease enzymes. Proteins encoded by the SAMHD1 genes. These proteins may be involved in immune response and/or inflammatory processes. |
| cystic fibrosis | Cystic fibrosis transmembrane conductance regulator. A transmembrane chloride channel protein. |
| progeria | Lamin A; lamin C. Proteins located at the nuclear lamina. |
| Marfan syndrome | Fibrillin-1. A large extracellular matrix protein. |
| tuberous sclerosis | Hamartin; tuberin. Hamartin is a peripheral membrane protein. Tuberin associates with hamartin in a cytosolic complex. |
| adrenoleukodystrophy | Adrenoleukodystrophy protein. A peroxisome membrane protein. |

Figure 6:
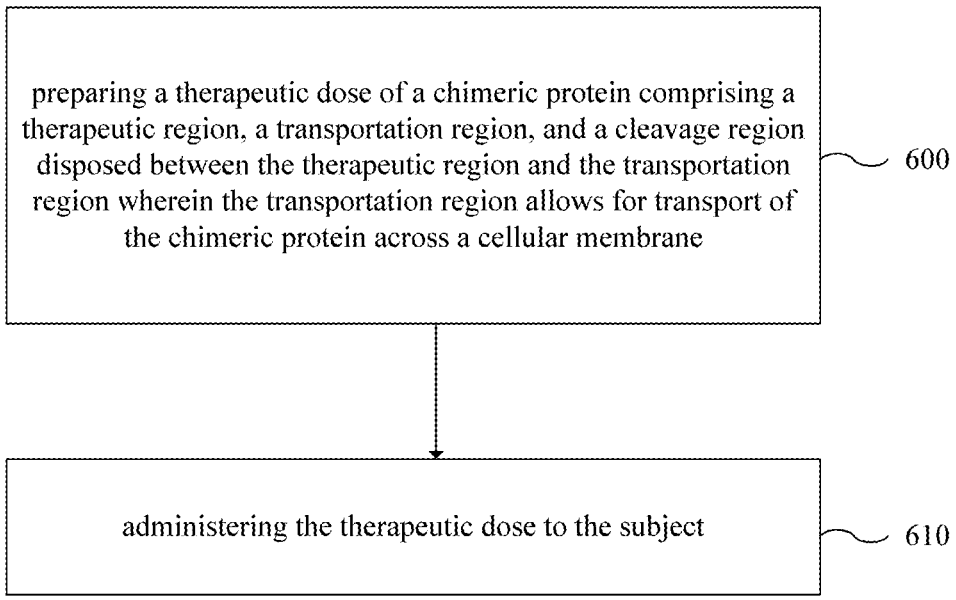
FIG. 6 shows a flowchart of a method of treating a subject having a medical condition using the chimeric protein shown in FIG. 1.

In some embodiments, the present disclosure is also directed to a method of using a chimeric protein consistent with the embodiments described above in the treatment of dystrophinopathies. As shown in FIG. 6, un some embodiments, the method of treating a subject having a dystrophinopathy includes the steps of preparing 600 a therapeutic dose of a chimeric protein comprising a therapeutic region, a transportation region, and a cleavage region disposed between the therapeutic region and the transportation region, wherein the transportation region allows for transport of the chimeric protein across a cellular membrane; and administering 610 the therapeutic dose to the subject. As used herein, the term therapeutic dose means any suitable volume and concentration of the chimeric protein to be administered to a subject as part of a prescribed regimen that is effective for treating a dystrophinopathy. The specific dosage is a matter of design choice and may vary with the characteristics of the subject.

Figure 7:
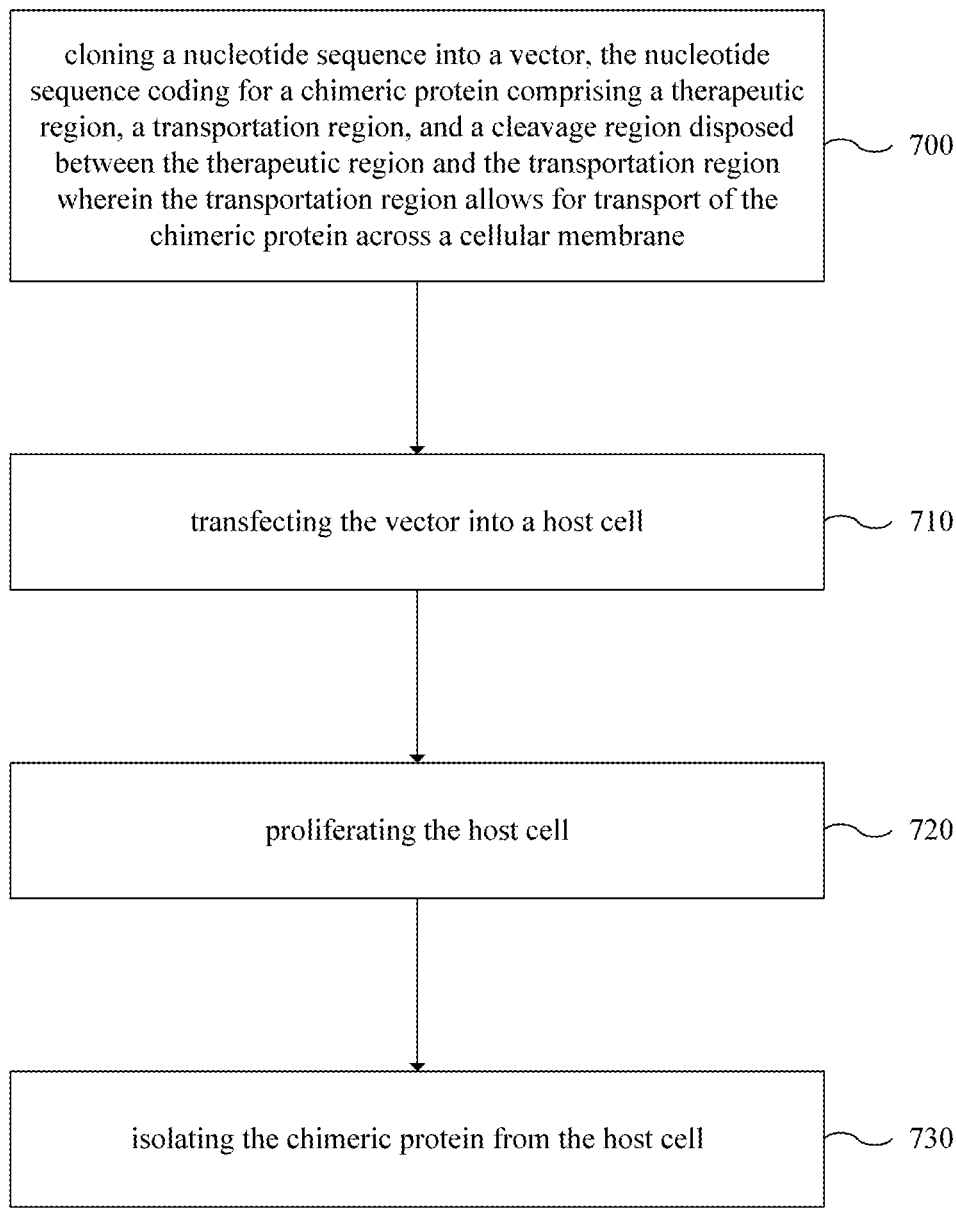
FIG. 7 shows a flowchart of a method of making the chimeric protein shown in FIG. 1 for use in the treatment of a condition.
Figure 8:
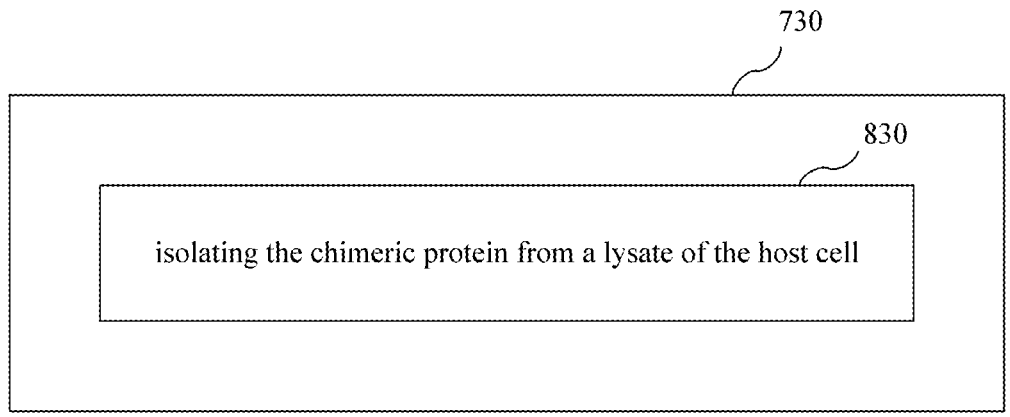
FIG. 8 shows another embodiment of the method of making a chimeric protein for use in the treatment of a condition as shown in FIG. 7.

Methods:

In some embodiments, the present disclosure is also directed to a method of making a chimeric protein consistent with the embodiments described above for use in the treatment of dystrophinopathies. As shown in FIG. 7, in some embodiments, the method of making the chimeric protein includes the steps of cloning 700 a nucleotide sequence into a vector, the nucleotide sequence coding for a chimeric protein comprising a therapeutic region, a transportation region, and a cleavage region disposed between the therapeutic region and the transportation region, wherein the transportation region allows for transport of the chimeric protein across a cellular membrane, transfecting 710 the vector into a host cell, proliferating 720 the host cell, and isolating 730 the chimeric protein from the host cell. In some embodiments, as shown in FIG. 8, isolating step 730 includes the step of isolating 830 the chimeric protein from a lysate of the host cell. Specific examples consistent with some embodiments of the method of making the chimeric protein are as follows:

The dystrophin protein has been described by Kunkel et al., under patent application Ser. No. 07/136,618 and family ID 22473616, the contents of which are incorporated herein by reference in its entirety. The complete mRNA sequence of human dystrophin protein is available at gene bank under accession number M18533, M17154, M18026, and M20250.

The following studies were all performed on a chimeric dystrophin protein without a cleavage region and with VSV-G as the transportation region at the N-terminus of the therapeutic dystrophin.

Plasmid harboring cDNA for full-length Homo Sapiens dystrophin was sourced from Transomic Technologies, 601 Genome Way, Suite 1222, Huntsville, AL 35806. Cloning vector pRK-Flag-Myc (Sigma) and pMD2.G (Addgene) harboring the VSV-G cDNA were obtained. The VSV-G protein was cloned at the ApaI and NotI sites of the pRK-Flag-Myc vector thereby replacing the Flag tag with VSV-G. VSV-G protein was cloned by polymerase chain reaction (PCR) using pMD2.G vector as the template and forward and reverse primers as 5' AAT TAT GGG CCC GAC ACC ATG GAG TGC CTT TTG TAC TTA 3' (SEQ ID NO: 10) and 5' CTC TAC TTG GCT GAA CCT CGC CGG CGG TTT AGG 3' (SEQ ID NO: 11) respectively.

Next, PCR was performed to amplify the dystrophin open reading frame (ORF) with forward and reverse primers as CCG TCA GCG GCC GCC ATG CTT TGG TGG GAA GAA GTA (SEQ ID NO: 12) and TAC TCT CTC CTG TGT TAC CAG CTG GAG TAC (SEQ ID NO: 13) respectively, designed to include restriction enzyme sites Not I and Sal I. The dystrophin ORF was cloned at the Not I and Sal I sites of the pRK-Flag-Myc vector following the VSV-G, yielding the chimeric dystrophin with VSV-G at the N-terminal. The KAPA HiFi HotStart ReadyMix PCR kit was used for performing PCR.

Dystrophin and truncated dystrophin chimeric gene sequences with N-terminal VSV-G were synthesized by IDT DNA using their propriety technology and put into appropriate vector for protein expression using a baculovirus system. Methods of protein purification using a baculovirus system are well established and well within the capabilities of one having ordinary skill in the art.

Once the chimeric sequence was generated, it was transfected in mammalian cells to ensure that the chimeric dystrophin protein is being expressed properly. HEK-293 cells were seeded on coverslips in a 6-well plate at a confluence of 60%. Cells were transfected with vectors containing either the VSV-G protein alone or the chimeric dystrophin-VSV-G protein using the Viafect™ reagent from Promega. A day after transfection the media were changed to normal media (10% FBS in DMEM). 48 hours post transfection, the media from the cells was removed.

Figure 2:
FIG. 2 shows an immunostaining of HEK-293 cells transfected with VSV-G only against VSV-G antibody.
Figure 3:
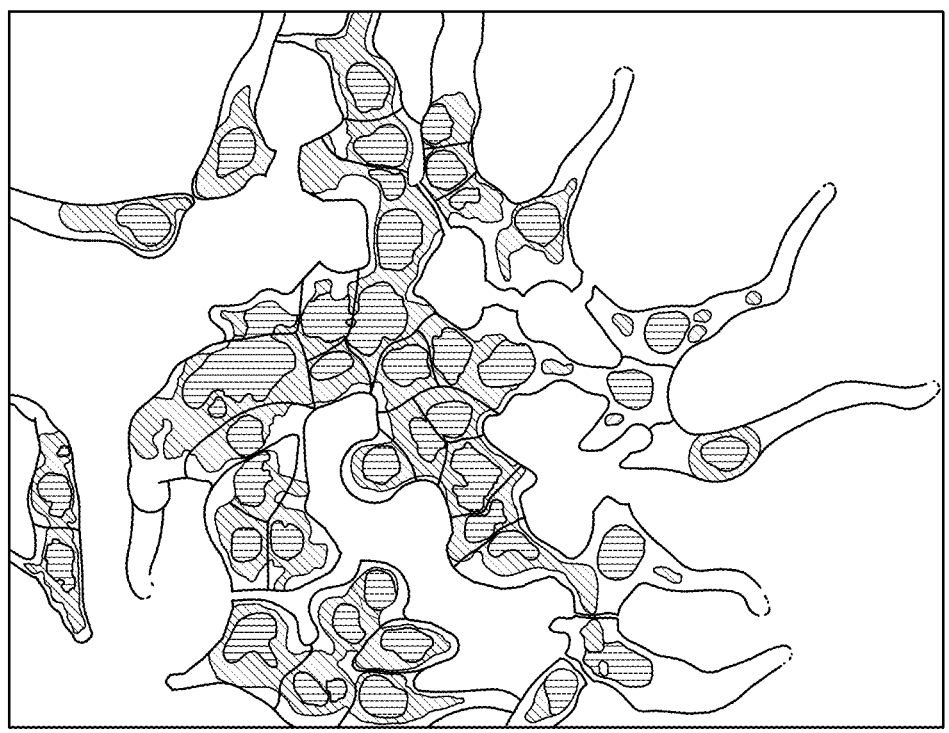
FIG. 3 shows an immunostaining of HEK-293 cells transfected with the chimeric dystrophin protein shown in FIG. 1 having VSV-G at the N-terminus against anti-VSV-G antibody.

As shown in FIGS. 2 and 3, the transfected cells seeded on coverslips were fixed and stained for detection of dystrophin chimeric protein expression and compared to that of VSV-G alone. For fixation, cells were washed in Dulbecco's phosphate buffered saline (DPBS) and fixed in 4% paraformaldehyde solution for 10 minutes. Cells were washed in DPBS again followed by treatment with 0.5% Triton-X-100 for an additional 5 minutes. Following 3 washes in DPBS, cells were blocked for an hour in 10% BSA. Then primary antibody against VSV-G protein (VSV-G-tag Antibody, pAb, Rabbit, source: GenScript) or dystrophin (monoclonal anti-dystrophin, clone MANDYS8) was added at a dilution of 1:100 in 2.5% BSA-DPBS for one and half hours. Cells were again washed in DPBS. Anti-rabbit FITC conjugated secondary antibody against anti-VSV-G primary or Anti-mouse Texas Red conjugated secondary antibody against anti-dystrophin primary were also added at a dilution of 1:100 in 2.5% BSA-DPBS and incubated for 30 minutes. Cells were washed in DPBS and stained with DAPI in DPBS. Cells were mounted in anti-fade mounting medium.

The stained transfected HEK-293 cells were detected for indirect immunofluorescence under a fluorescence microscope. The transfected cells displayed fluorescence in the cytoplasm confirming the expression of the chimeric protein (FIG. 3). The distribution of the VSV-G protein alone was different from that of the chimeric protein (FIG. 2).

DMD patient cells (GM05169 and GM03604 A) were sourced from Coriell Institute of Biomedical Research. For treatment of DMD patient cells with conditioned media, GM05169 and GM03604 A cells were seeded onto coverslips in 6-well plate. HEK 293 cells were transfected as described above and the media after being changed 24 hours post transfection was left for another 48 hours. 72 hours post transfection, medium from the transfected cells were collected and centrifuged. Different amounts of conditioned HEK transfection media 2.0 ml, 1.0 ml, and 0.5 ml (making a total volume of 2 ml by adding 15% FBS DMEM media) were added to the DMD patient cells and then cells were fixed and stained as described above.

Figure 4:
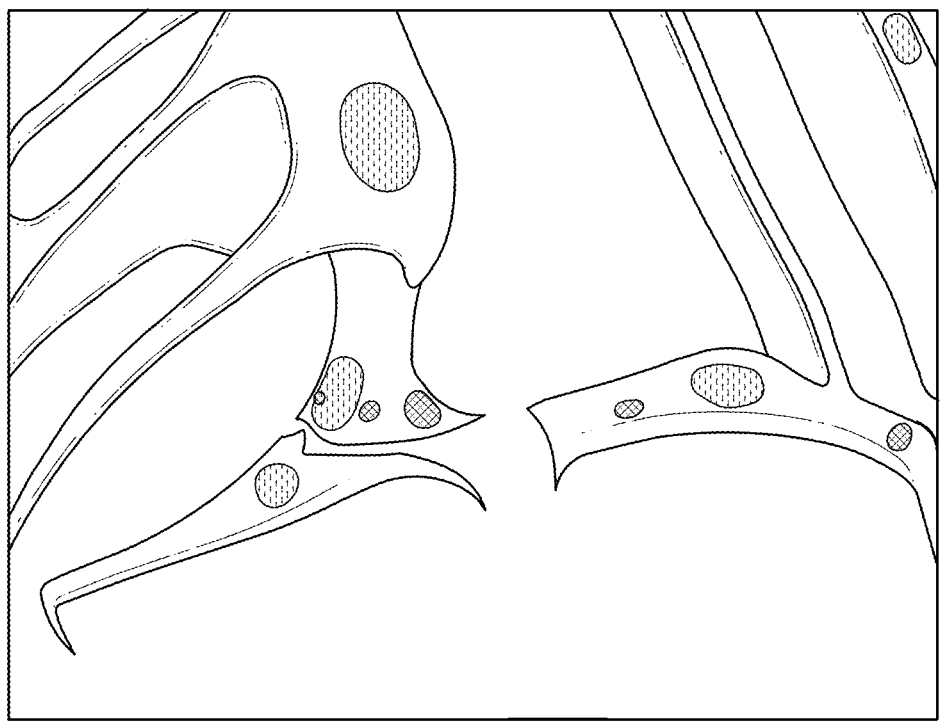
FIG. 4 shows an immunostaining of DMD patient cells with an anti-dystrophin antibody treated with 0.5 ml of conditioned media derived from HEK-293 cells transfected with chimeric dystrophin having VSV-G at the N-terminus.
Figure 5:
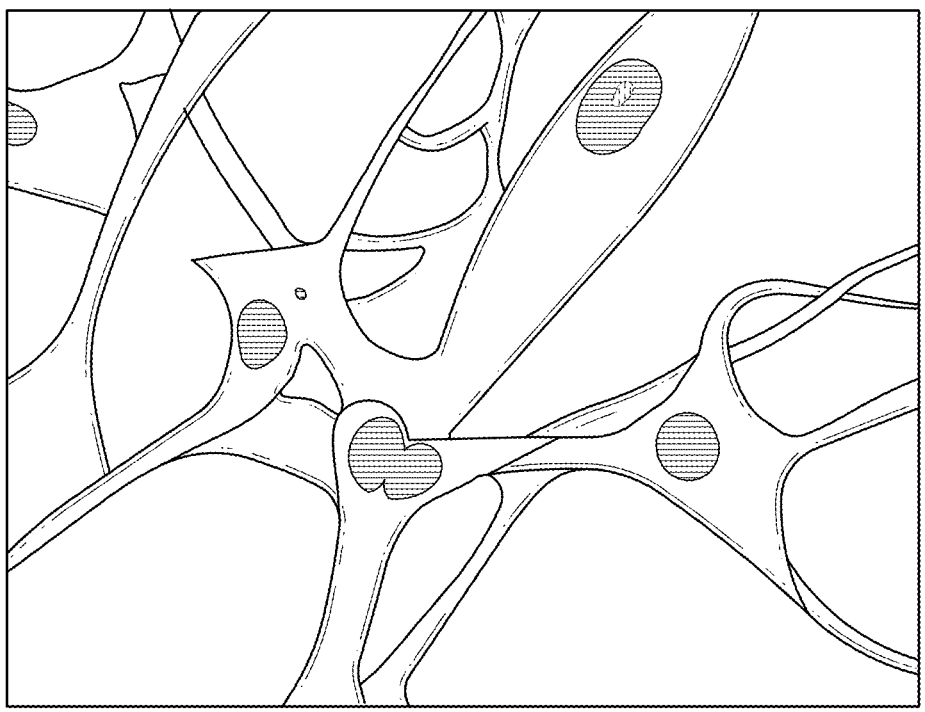
FIG. 5 shows an immunostaining of DMD patient cells with an anti-dystrophin antibody treated with 2.0 ml of conditioned media derived from HEK-293 cells transfected with chimeric dystrophin having VSV-G at the N-terminus.

DMD patient cells were then analyzed under a fluorescence microscope for chimeric protein transduction from media to patient cells. As shown in FIGS. 4 and 5, treatment of conditioned transfected HEK-293 cell media indeed resulted in the transduction of chimeric protein that was secreted in the media as displayed by the fluorescence in the cytoplasm of patient cells.

It was postulated that fusion of VSV-G protein with the dystrophin protein would facilitate the entry of the dystrophin protein in the target muscle tissues. VSV-G is a vesicular protein which when overexpressed is secreted in vesicles known as gesicles. It was assumed, therefore, that chimeric dystrophin protein might be secreted as well in the transfection media upon expression. DMD patient cells displaying fluorescence positive for chimeric protein proves that the chimeric protein is secreted in the media of HEK-293 transfected cells and upon treatment of the conditioned media to DMD patient cells, the chimeric protein is taken up by the patient cells.

As discussed above, in some embodiments, chimeric protein expression and functionality is confirmed by inserting DNA encoding the chimeric protein into baculovirus for recombinant protein production. DNA insertion into the baculovirus for recombinant protein production is accomplished using the commercially available pOET1 transfer plasmid (Oxford Expression Technologies) and recombinant baculovirus stocks are prepared for baculovirus-mediated protein expression according to the manufacturer protocols.

Chimeric proteins are produced using recombinant baculovirus stocks to infect suspension cultures of insect cells grown in flasks or bioreactors with commercially available cell lines such as Sf9, Sf21 or Tni and commercially available culture media according to manufacturer protocols. Infected cultures are then harvested between 48 and 96 hours post infection and chimeric proteins are purified from culture media or clarified cell lysate by column chromatography involving one or more methods such as affinity, ion exchange, hydrophobic interaction, and size exclusion.

Purified chimeric proteins are identified by Western blot using one or more dystrophin-specific primary antibodies. Protein purity is determined by densitometry analysis of SDS PAGE stained with SYPRO Orange or Coomassie Blue, and by reverse phase high performance liquid chromatography (RP-HPLC). Protein stability in phosphate buffered saline (PBS) or similar formulation buffer is assessed by analytical size exclusion chromatography (aSEC) to detect changes in protein monodispersity over time and after multiple freeze/thaw cycles. Endotoxin level in purified protein samples is measured by Limulus Amebocyte Lysate (LAL) assay.

Purified chimeric protein produced by the methods described above is administered in mdx mice for further validation of its activity to improve the pathologic effects observed during dystrophinopathies. All the animal studies are done by The Jackson Laboratory.

A variant of mdx mouse in a different background (DBA/2J) is used for the studies. Eighteen hemizygous D2.B10-Dmdmdx/J male mutant mice and six DBA/2J male control mice are produced in the Jackson Laboratory Facility. Three groups of 6 D2.B10-Dmdmdx/J males, age 28 days±3 days, are administered the chimeric protein or vehicle for a six week period. A group of 6 DBA/2J male controls, age 28 days±3 days, are administered just the chimeric protein administration vehicle.

At the end of the treatment period, the following measurements are performed:

Serum Creatine Kinase (CK) activity. Serum CK is measured with a Beckman Coulter AU Clinical Chemistry analyzer from serum collected by retro-orbital bleeding and frozen immediately and until analysis;

Evans Blue Dye (EBD) uptake by the skeletal muscle. EBD is injected 24 hours prior to euthanasia but after serum collection for CK measurement. After euthanasia, the gastrocnemius is collected and flash frozen. Muscles are then homogenized, the lysate is cleared, and EBD concentration in the supernatant is measured by spectrophotometry;

Histology. Hematoxylin and eosin stain for illustration purposes, reticulin stain for muscle fiber morphometry, quantification of the extent of atrophy/hypertrophy and centrally-located nuclei, and Masson Trichrome stain for the visualization of the fibrosis are performed. After sacrifice, one hind limb and one hemi-diaphragm are collected and fixed in paraformaldehyde. Muscles are dissected, paraffin-embedded, and cross-sectioned. Three sections per muscle are prepared to be stained with hematoxylin and eosin for illustration purposes with two mice per group and reticulin stain for automated fiber size measurements and central nuclei counts;

Anti-dystrophin immunofluorescence on the quadriceps, myocardium, and diaphragm. Tibialis anterior and quadriceps muscles are used. One quadriceps and the heart are flash-frozen without fixation for cryo-sectioning and cross-sections are stained by anti-dystrophin immunofluorescence; and RNA extraction and quantification of the following mRNAs in the tibialis anterior: markers of inflammation, markers of fibrosis, markers of muscle fiber regeneration. One tibialis anterior is preserved in RNA. Later, RNAs are extracted, reverse-transcribed, and the following mRNA quantified by SYBR-Green qPCR: Mpeg1 and Lgals3 (macrophages markers), Ly6c1 (pro-fibrotic monocytes marker), Tnf-alpha (inflammatory cytokine), neonatal myosin (fiber regeneration marker), and collagen I.

One or more embodiments of the present invention have been described. Nevertheless, it will be understood that various modifications may be made without departing from the spirit and scope of the invention. Accordingly, other embodiments are within the scope of the following claims.

What is claimed is:

1. A chimeric protein consisting of a therapeutic region, a transportation region, and a tissue-specific cleavage region disposed between the therapeutic region and the transportation region, wherein the transportation region facilitates for transport of the chimeric protein across a cellular membrane and the transportation region is selected from the group consisting of: a full length vesicular stomatitis virus G (VSV-G) and functional variants of a vesicular stomatitis virus G, wherein at least a portion of a sequence of the chimeric protein is selected from the group consisting of: SEQ ID NO: 2, SEQ ID NO: 4, SEQ ID NO: 6, SEQ ID NO: 8.

2. The chimeric protein according to claim 1, wherein the tissue-specific cleavage region is disposed at the N-terminal end of the therapeutic region.

3. The chimeric protein according to claim 1, wherein the tissue-specific cleavage region is disposed at the C-terminal end of the therapeutic region.

4. The chimeric protein according to claim 1, wherein the therapeutic region is selected from the group consisting of: a full-length dystrophin, a truncated dystrophin, and combinations thereof.

5. The chimeric protein according to claim 1, wherein the vesicular stomatitis virus G variants has at least a sequence identity with a wild-type vesicular stomatitis virus G selected from the group consisting of: at least 90%, at least 95%, at least 96%, at least 97%, at least 98%, or at least 99% sequence identity.

6. The chimeric protein according to claim 1, wherein the tissue-specific cleavage region is a cleavage site for a membrane metalloprotease (MMP).

7. A chimeric protein for the treatment of a subject having a muscular dystrophy, the chimeric protein having a sequence wherein at least a portion of the sequence is selected from the group consisting of: SEQ ID NO: 2, SEQ ID NO: 4, SEQ ID NO: 6, SEQ ID NO: 8.

* * * * *

SEQUENCE LISTING

```
<160> NUMBER OF SEQ ID NOS: 13

<210> SEQ ID NO 1
<211> LENGTH: 12594
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic nucleotide sequence of proposed Dystrophin-VSV-G
      chimeric protein with VSV-G at N-terminal"

<400> SEQUENCE: 1
atgaagtgcc ttttgtactt agcttttta ttcatcgggg tgaattgcaa gttcaccata          60 gttttccac acaaccaaaa aggaaactgg aaaaatgttc cttccaatta ccattattgc         120
ccgtcaagct cagatttaaa ttggcataat gacttaatag gcacagcctt acaagtcaaa        180
atgcccaaga gtcacaaggc tattcaagca gacggttgga tgtgtcatgc ttccaaatgg        240
gtcactactt gtgatttccg ctggtacgga ccgaagtata taacacattc catccgatcc        300
ttcactccat ctgtagaaca atgcaaggaa agcattgaac aaacgaaaca aggaacttgg        360
ctgaatccag gcttccctcc tcaaagttgt ggatatgcaa ctgtgacgga tgctgaagca        420
```

```
gcgattgtcc aggtgactcc tcaccatgtg cttgttgatg aatacacagg agaatgggtt    480
gattcacagt tcatcaacgg aaaatgcagc aatgacatat gccccactgt ccataactcc    540
acaacctggc attccgacta aaggtcaaa gggctatgtg attctaacct catttccacg     600
gacatcacct tcttctcaga ggacggagag ctatcatccc taggaaagga gggcacaggg    660
ttcagaagta actactttgc ttatgaaact ggagacaagg cctgcaaaat gcagtactgc    720
aagcattggg gagtcagact cccatcaggt gtctggttcg agatggctga taaggatctc    780
tttgctgcag ccagattccc tgaatgccca gaagggtcaa gtatctctgc tccatctcag    840
acctcagtgg atgtaagtct cattcaggac gttgagagga tcttggatta ttccctctgc    900
caagaaacct ggagcaaaat cagagcgggt cttcccatct ctccagtgga tctcagctat    960
cttgctccta aaacccagg aaccggtcct gtctttacca taatcaatgg taccctaaaa   1020
tactttgaga ccagatacat cagagtcgat attgctgctc aatcctctc aagaatggtc   1080
ggaatgatca gtggaactac cacagaaagg gaactgtggg atgactgggc tccatatgaa   1140
gacgtggaaa ttgacccaa tggagttctg aggaccagtt taggatataa gtttccttta   1200
tatatgattg acatggtat gttggactcc gatcttcatc ttagctcaaa ggctcaggtg   1260
tttgaacatc ctcacattca agacgctgct tcgcagcttc ctgatgatga actttattt   1320
tttggtgata ctgggctatc caaaaatcca atcgagtttg tagaaggttg gttcagtagt   1380
tggaagagct ctattgcctc ttttttcttt atcatagggt taatcattgg actattcttg   1440
gttctccgag ttggtattta tctttgcatt aaattaaagc acaccaagaa aagacagatt   1500
tatacagaca tagagatgaa cccacttgga ctgtgggcgc tttggtggga agaagtagag   1560
gactgttatg aaagagaaga tgttcaaaag aaaacattca caaatgggt aaatgcacaa   1620
ttttctaagt ttgggaagca gcatattgag aacctcttca gtgacctaca ggatgggagg   1680
cgcctcctag acctcctcga aggcctgaca gggcaaaaac tgccaaaaga aaaggatcc   1740
acaagagttc atgccctgaa caatgtcaac aaggcactgc gggttttgca gaacaataat   1800
gttgatttag tgaatattgg aagtactgac atcgtagatg gaaatcataa actgactctt   1860
ggtttgattt ggaatataat cctccactgg caggtcaaaa atgtaatgaa aaatatcatg   1920
gctggattgc aacaaaccaa cagtgaaaag attctcctga gctgggtccg acaatcaact   1980
cgtaattatc cacaggttaa tgtaatcaac ttcaccacca gctggtctga tggcctggct   2040
ttgaatgctc tcatccatag tcataggcca gacctatttg actggaatag tgtggtttgc   2100
cagcagtcag ccacacaacg actgaacat gcattcaaca tcgccagata tcaattaggc   2160
atagagaaac tactcgatcc tgaagatgtt gataccacct atccagataa gaagtccatc   2220
ttaatgtaca tcacatcact cttccaagtt ttgcctcaac aagtgagcat tgaagccatc   2280
caggaagtgg aaatgttgcc aaggccacct aaagtgacta agaagaaaca ttttcagtta   2340
catcatcaaa tgcactattc tcaacagatc acggtcagtc tagcacaggg atatgagaga   2400
acttcttccc ctaagcctcg attcaagagc tatgcctaca cacaggctgc ttatgtcacc   2460
acctctgacc ctacacggag cccatttcct tcacagcatt ggaagctcc tgaagacaag   2520
tcatttggca gttcattgat ggagagtgaa gtaaacctgg accgttatca acagctttta   2580
gaagaagtat tatcgtggct tctttctgct gaggacacat tgcaagcaca aggagagatt   2640
tctaatgatg tggaagtggt gaaagaccag tttcatactc atgaggggta catgatggat   2700
ttgacagccc atcagggccg ggttggtaat attctacaat tgggaagtaa gctgattgga   2760
acaggaaaat tatcagaaga tgaagaaact gaagtacaag agcagatgaa tctcctaaat   2820
```

```
tcaagatggg aatgcctcag ggtagctagc atggaaaaac aaagcaattt acatagagtt   2880
ttaatggatc tccagaatca gaaactgaaa gagttgaatg actggctaac aaaaacagaa   2940
gaaagaacaa ggaaaatgga ggaagagcct cttggacctg atcttgaaga cctaaaacgc   3000
caagtacaac aacataaggt gcttcaagaa gatctagaaa agaacaagt cagggtcaat   3060 tctctcactc acatggtggt ggtagttgat gaatctagtg gagatcacgc aactgctgct   3120
ttggaagaac aacttaaggt attgggagat cgatgggcaa acatctgtag atggacagaa   3180
gaccgctggg ttcttttaca agacatcctt ctcaaatggc aacgtcttac tgaagaacag   3240
tgccttttta gtgcatggct ttcagaaaaa gaagatgcag tgaacaagat tcacacaact   3300
ggctttaaag atcaaaatga aatgttatca agtcttcaaa aactggccgt tttaaaagcg   3360
gatctagaaa agaaaaagca atccatgggc aaactgtatt cactcaaaca agatcttctt   3420
tcaacactga agaataagtc agtgacccag aagacggaag catggctgga taactttgcc   3480
cggtgttggg ataatttagt ccaaaaactt gaaaagagta cagcacagat ttcacaggct   3540
gtcaccacca ctcagccatc actaacacag acaactgtaa tggaaacagt aactacggtg   3600
accacaaggg aacagatcct ggtaaagcat gctcaagagg aacttccacc accacctccc   3660
caaaagaaga ggcagattac tgtggattct gaaattagga aaaggttgga tgttgatata   3720
actgaacttc acagctggat tactcgctca gaagctgtgt tgcagagtcc tgaatttgca   3780
atctttcgga aggaaggcaa cttctcagac ttaaaagaaa aagtcaatgc catagagcga   3840
gaaaaagctg agaagttcag aaaactgcaa gatgccagca gatcagctca ggccctggtg   3900
gaacagatgg tgaatgaggg tgttaatgca gatagcatca acaagcctc agaacaactg   3960 aacagccggt ggatcgaatt ctgccagttg ctaagtgaga gacttaactg gctggagtat   4020
cagaacaaca tcatcgcttt ctataatcag ctacaacaat tggagcagat gacaactact   4080
gctgaaaact ggttgaaaat ccaacccacc accccatcag agccaacagc aattaaaagt   4140
cagttaaaaa tttgtaagga tgaagtcaac cggctatcag gtcttcaacc tcaaattgaa   4200
cgattaaaaa ttcaaagcat agccctgaaa gagaaaggac aaggacccat gttcctggat   4260
gcagactttg tggcctttac aaatcatttt aagcaagtct tttctgatgt gcaggccaga   4320
gagaaagagc tacagacaat ttttgacact tgccaccaa tgcgctatca ggagaccatg   4380
agtgccatca ggacatgggt ccagcagtca gaaaccaaac tctccatacc tcaacttagt   4440
gtcaccgact atgaaatcat ggagcagaga ctcggggaat tgcaggcttt acaaagttct   4500
ctgcaagagc aacaaagtgg cctatactat ctcagcacca ctgtgaaaga gatgtcgaag   4560
aaagcgccct ctgaaattag ccggaaatat caatcagaat ttgaagaaat tgagggacgc   4620
tggaagaagc tctcctccca gctggttgag cattgtcaaa agctagagga gcaaatgaat   4680
aaactccgaa aaattcagaa tcacatacaa accctgaaga aatggatggc tgaagttgat   4740 gttttttctga aggaggaatg gcctgccctt gggattcag aaattctaaa aaagcagctg   4800
aaacagtgca gacttttagt cagtgatatt cagacaattc agcccagtct aaacagtgtc   4860
aatgaaggtg ggcagaagat aaagaatgaa gcagagccag agtttgcttc gagacttgag   4920
acagaactca agaacttaa cactcagtgg gatcacatgt gccaacaggt ctatgccaga   4980
aaggaggcct tgaagggagg tttggagaaa actgtaagcc tccagaaaga tctatcagag   5040
atgcacgaat ggatgacaca agctgaagaa gagtatcttg agagagattt tgaatataaa   5100
actccagatg aattacagaa agcagttgaa gagatgaaga gagctaaaga agaggcccaa   5160
```

-continued

```
caaaaagaag cgaaagtgaa actccttact gagtctgtaa atagtgtcat agctcaagct    5220
ccacctgtag cacaagaggc cttaaaaaag gaacttgaaa ctctaaccac caactaccag    5280
tggctctgca ctaggctgaa tgggaaatgc aagactttgg aagaagtttg ggcatgttgg    5340
catgagttat tgtcatactt ggagaaagca aacaagtggc taaatgaagt agaatttaaa    5400
cttaaaacca ctgaaaacat tcctggcgga gctgaggaaa tctctgaggt gctagattca    5460
cttgaaaatt tgatgcgaca ttcagaggat aacccaaatc agattcgcat attggcacag    5520
accctaacag atggcggagt catggatgag ctaatcaatg aggaacttga gacatttaat    5580
tctcgttgga gggaactaca tgaagaggct gtaaggaggc aaaagttgct tgaacagagc    5640
atccagtctg cccaggagac tgaaaaatcc ttacacttaa tccaggagtc cctcacattc    5700
attgacaagc agttggcagc ttatattgca gacaaggtgg acgcagctca aatgcctcag    5760
gaagcccaga aaatccaatc tgatttgaca agtcatgaga tcagtttaga gaaatgaag    5820 aaacataatc aggggaagga ggctgcccaa agagtcctgt ctcagattga tgttgcacag    5880
aaaaaattac aagatgtctc catgaagttt cgattattcc agaaaccagc caattttgag    5940
ctgcgtctac aagaaagtaa gatgatttta gatgaagtga gatgcactt gcctgcattg    6000 gaaacaaaga gtgtggaaca ggaagtagta cagtcacagc taaatcattg tgtgaacttg    6060
tataaaagtc tgagtgaagt gaagtctgaa gtggaaatgg tgataaagac tggacgtcag    6120
attgtacaga aaaagcagac ggaaaatccc aaagaacttg atgaaagagt aacagctttg    6180
aaattgcatt ataatgagct gggagcaaag gtaacagaaa gaaagcaaca gttggagaaa    6240
tgcttgaaat tgtcccgtaa gatgcgaaag gaaatgaatg tcttgacaga atggctggca    6300
gctacagata tggaattgac aaagagatca gcagttgaag gaatgcctag taatttggat    6360
tctgaagttg cctggggaaa ggctactcaa aaagagattg agaaacagaa ggtgcacctg    6420
aagagtatca cagaggtagg agaggccttg aaaacagttt tgggcaagaa ggagacgttg    6480
gtggaagata aactcagtct tctgaatagt aactggatag ctgtcacctc ccgagcagaa    6540
gagtggttaa atcttttgtt ggaataccag aaacacatgg aaacttttga ccagaatgtg    6600
gaccacatca caaagtggat cattcaggct gacacacttt tggatgaatc agagaaaaag    6660
aaaccccagc aaaaagaaga cgtgcttaag cgtttaaagg cagaactgaa tgacatacgc    6720 ccaaggtgg actctacacg tgaccaagca gcaaacttga tggcaaaccg cggtgaccac    6780
tgcaggaaat tagtagagcc ccaaatctca gagctcaacc atcgatttgc agccatttca    6840
cacagaatta agactggaaa ggcctccatt cctttgaagg aattggagca gtttaactca    6900
gatatacaaa aattgcttga accactggag gctgaaattc agcaggggt gaatctgaaa    6960 gaggaagact tcaataaaga tatgaatgaa gacaatgagg gtactgtaaa agaattgttg    7020
caaagaggag acaacttaca acaaagaatc acagatgaga gaaagagaga ggaaataaag    7080
ataaaacagc agctgttaca gacaaaaacat aatgctctca aggatttgag gtctcaaaga    7140
agaaaaaagg ctctagaaat ttctcatcag tggtatcagt acaagaggca ggctgatgat    7200
ctcctgaaat gcttggatga cattgaaaaa aaattagcca gcctacctga gcccagagat    7260
gaaaggaaaa taaggaaat tgatcgggaa ttgcagaaga agaaagagga gctgaatgca    7320
gtgcgtaggc aagctgaggg cttgtctgag gatggggccg caatggcagt ggagccaact    7380
cagatccagc tcagcaagcg ctggcgggaa attgagagca aatttgctca gtttcgaaga    7440
ctcaactttg cacaaattca cactgtccgt gaagaaacga tgatggtgat gactgaagac    7500
atgcctttgg aaatttctta tgtgccttct acttatttga ctgaaatcac tcatgtctca    7560
```

```
caagccctat tagaagtgga acaacttctc aatgctcctg acctctgtgc taaggacttt    7620
gaagatctct ttaagcaaga ggagtctctg aagaatataa aagatagtct acaacaaagc    7680
tcaggtcgga ttgacattat tcatagcaag aagacagcag cattgcaaag tgcaacgcct    7740
gtggaaaggg tgaagctaca ggaagctctc tcccagcttg atttccaatg ggaaaaagtt    7800
aacaaaatgt acaaggaccg acaagggcga tttgacagat ctgttgagaa atggcggcgt    7860
tttcattatg atataaagat atttaatcag tggctaacag aagctgaaca gtttctcaga    7920
aagacacaaa ttcctgagaa ttgggaacat gctaaataca aatggtatct taaggaactc    7980
caggatggca ttgggcagcg gcaaactgtt gtcagaacat gaatgcaac tggggaagaa    8040 ataattcagc aatcctcaaa aacagatgcc agtattctac aggaaaaatt gggaagcctg    8100
aatctgcggt ggcaggaggt ctgcaaacag ctgtcagaca gaaaaagag ctagaagaa    8160 caaaagaata tcttgtcaga atttcaaaga gatttaaatg aatttgtttt atggttggag    8220
gaagcagata acattgctag tatcccactt gaacctggaa aagagcagca actaaaagaa    8280
aagcttgagc aagtcaagtt actggtggaa gagttgcccc tgcgccaggg aattctcaaa    8340
caattaaatg aaactggagg acccgtgctt gtaagtgctc ccataagccc agaagagcaa    8400
gataaacttg aaaataagct caagcagaca aatctccagt ggataaaggt ttccagagct    8460
ttacctgaga acaaggaga aattgaagct caaataaaag accttgggca gcttgaaaaa    8520
aagcttgaag accttgaaga gcagttaaat catctgctgc tgtggttatc tcctattagg    8580
aatcagttgg aaatttataa ccaaccaaac caagaaggac catttgacgt tcaggaaact    8640
gaaatagcag ttcaagctaa acaaccggat gtggaagaga ttttgtctaa agggcagcat    8700
ttgtacaagg aaaaaccagc cactcagcca gtgaagagga agttagaaga tctgagctct    8760
gagtggaagg cggtaaaccg tttacttcaa gagctgaggg caaagcagcc tgacctagct    8820
cctggactga ccactattgg agcctctcct actcagactg ttactctggt gacacaacct    8880
gtggttacta aggaaactgc catctccaaa ctagaaatgc catcttcctt gatgttggag    8940
gtacctgctc tggcagattt caaccgggct tggacagaac ttaccgactg gctttctctg    9000
cttgatcaag ttataaaatc acagagggtg atggtgggtg accttgagga tatcaacgag    9060
atgatcatca gcagaaggc aacaatgcag gatttggaac agaggcgtcc ccagttggaa    9120
gaactcatta ccgctgccca aaatttgaaa aacaagacca gcaatcaaga ggctagaaca    9180
atcattacgg atcgaattga agaattcag aatcagtggg atgaagtaca agaacacctt    9240
cagaaccgga ggcaacagtt gaatgaaatg ttaaaggatt caacacaatg gctgaaagct    9300
aaggaagaag ctgagcaggt cttaggacag gccagagcca agcttgagtc atggaaggag    9360
ggtccctata cagtagatgc aatccaaaag aaaatcacag aaaccaagca gttggccaaa    9420
gacctccgcc agtggcagac aaatgtagat gtggcaaatg acttggccct gaaacttctc    9480
cgggattatt ctgcagatga taccagaaaa gtccacatga taacagagaa tatcaatgcc    9540
tcttggagaa gcattcataa aagggtgagt gagcgagagg ctgctttgga agaaactcat    9600
agattactgc aacagttccc cctggaccctg gaaaagtttc ttgcctggct tacagaagct    9660
gaaacaactg ccaatgtcct acaggatgct acccgtaagg aaaggctcct agaagactcc    9720
aagggagtaa aagagctgat gaaacaatgg caagacctcc aaggtgaaat tgaagctcac    9780
acagatgttt atcacaacct ggatgaaaac agccaaaaaa tcctgagatc cctgaaggt    9840 tccgatgatg cagtcctgtt acaaagacgt ttggataaca tgaacttcaa gtggagtgaa    9900
```

```
cttcggaaaa agtctctcaa cattaggtcc catttggaag ccagttctga ccagtggaag   9960
cgtctgcacc tttctctgca ggaacttctg gtgtggctac agctgaaaga tgatgaatta  10020
agccggcagg cacctattgg aggcgacttt ccagcagttc agaagcagaa cgatgtacat  10080
agggccttca agagggaatt gaaaactaaa gaacctgtaa tcatgagtac tcttgagact  10140
gtacgaatat ttctgacaga gcagcctttg aaggactaga gaaactcta ccaggagccc   10200
agagagctgc ctcctgagga gagagcccag aatgtcactc ggcttctacg aaagcaggct  10260
gaggaggtca atactgagtg ggaaaaattg aacctgcact ccgctgactg gcagagaaaa  10320
atagatgaga cccttgaaag actccaggaa cttcaagagg ccacggatga gctggacctc  10380
aagctgcgcc aagctgaggt gatcaaggga tcctggcagc ccgtgggcga tctcctcatt  10440
gactctctcc aagatcacct cgagaaagtc aaggcacttc gaggagaaat tgcgcctctg  10500
aaagagaacg tgagccacgt caatgacctt gctcgccagc ttaccacttt gggcattcag  10560
ctctcaccgt ataacctcag cactctggaa gacctgaaca ccagatggaa gcttctgcag  10620
gtggccgtcg aggaccgagt caggcagctg catgaagccc acaggacttt ggtccagca  10680
tctcagcact ttctttccac gtctgtccag ggtccctggg agagagccat ctcgccaaac  10740
aaagtgccct actatatcaa ccacgagact caaacaactt gctgggacca tcccaaaatg  10800
acagagctct accagtcttt agctgacctg aataatgtca gattctcagc ttataggact  10860
gccatgaaac tccgaagact gcagaaggcc ctttgcttgg atctcttgag cctgtcagct  10920
gcatgtgatg ccttggacca gcacaacctc aagcaaaatg accagcccat ggatatcctg  10980
cagattatta attgtttgac cactatttat gaccgcctgg agcaagagca caacaatttg  11040
gtcaacgtcc ctctctgcgt ggatatgtgt ctgaactggc tgctgaatgt tatgatacg   11100
ggacgaacag ggaggatccg tgtcctgtct tttaaaactg gcatcatttc cctgtgtaaa  11160
gcacatttgg aagacaagta cagataccct tcaagcaag tggcaagttc aacaggattt   11220
tgtgaccagc gcaggctggg cctccttctg catgattcta ccaaattcc aagacagttg   11280
ggtgaagttg catcctttgg gggcagtaac attgagccaa gtgtccggag ctgcttccaa  11340
tttgctaata taagccaga gatcgaagcg gccctcttcc tagactggat gagactggaa   11400
ccccagtcca tggtgtggct gcccgtcctg cacagagtgg ctgctgcaga aactgccaag  11460
catcaggcca aatgtaacat ctgcaaagag tgtccaatca ttggattcag gtacaggagt  11520
ctaaagcact ttaattatga catctgccaa agctgctttt tttctggtcg agttgcaaaa  11580
ggccataaaa tgcactatcc catggtggaa tattgcactc cgactacatc aggagaagat  11640
gttcgagact ttgccaaggt actaaaaaac aaatttcgaa ccaaaaggta ttttgcgaag  11700
catccccgaa tgggctacct gccagtgcag actgtcttag aggggacaa catggaaact   11760
cccgttactc tgatcaactt ctggccagta gattctgcgc ctgcctcgtc ccctcagctt  11820
tcacacgatg atactcattc acgcattgaa cattatgcta gcaggctagc agaaatggaa  11880
aacagcaatg gatcttatct aaatgatagc atctctccta tgagagcat agatgatgaa   11940
catttgttaa tccagcatta ctgccaaagt ttgaaccagg actcccccct gagccagcct  12000
cgtagtcctg cccagatctt gatttcctta gagagtgagg aaagagggga gctagagaga  12060
atcctagcag atcttgagga agaaaacagg aatctgcaag cagaatatga ccgtctaaag  12120
cagcagcacg aacataaagg cctgtcccca ctgccgtccc ctcctgaaat gatgccacc   12180
tctccccaga gtcccggga tgctgagctc attgctgagg ccaagctact gcgtcaacac  12240
aaaggccgcc tggaagccag gatgcaaatc ctggaagacc acaataaaca gctggagtca  12300
```

```
cagttacaca ggctaaggca gctgctggag caaccccagg cagaggccaa agtgaatggc    12360
acaacggtgt cctctccttc tacctctcta cagaggtccg acagcagtca gcctatgctg    12420
ctccgagtgg ttggcagtca aacttcggac tccatgggtg aggaagatct tctcagtcct    12480
ccccaggaca caagcacagg gttagaggag gtgatggagc aactcaacaa ctccttccct    12540
agttcaagag gaagaaatac ccctggaaag ccaatgagag aggacacaat gtag          12594
```

<210> SEQ ID NO 2
<211> LENGTH: 4197
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic amino acid sequence of Dystrophin-VSV-G Chimeric protein
    with VSV-G at N-terminal"

<400> SEQUENCE: 2

```
Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Leu Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Ala Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Thr Asp Ile Thr Phe Phe Ser Glu Asp
        195                 200                 205

Gly Glu Leu Ser Ser Leu Gly Lys Glu Gly Thr Gly Phe Arg Ser Asn
    210                 215                 220

Tyr Phe Ala Tyr Glu Thr Gly Asp Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
```

```
            290                 295                 300
Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Val Phe Thr Ile Ile Asn
                325                 330                 335

Gly Thr Leu Lys Tyr Phe Glu Thr Arg Tyr Ile Arg Val Asp Ile Ala
                340                 345                 350

Ala Pro Ile Leu Ser Arg Met Val Gly Met Ile Ser Gly Thr Thr Thr
                355                 360                 365

Glu Arg Glu Leu Trp Asp Asp Trp Ala Pro Tyr Glu Asp Val Glu Ile
370                 375                 380

Gly Pro Asn Gly Val Leu Arg Thr Ser Leu Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
                420                 425                 430

Leu Pro Asp Asp Glu Thr Leu Phe Phe Gly Asp Thr Gly Leu Ser Lys
                435                 440                 445

Asn Pro Ile Glu Phe Val Glu Gly Trp Phe Ser Ser Trp Lys Ser Ser
                450                 455                 460

Ile Ala Ser Phe Phe Phe Ile Ile Gly Leu Ile Ile Gly Leu Phe Leu
465                 470                 475                 480

Val Leu Arg Val Gly Ile Tyr Leu Cys Ile Lys Leu Lys His Thr Lys
                485                 490                 495

Lys Arg Gln Ile Tyr Thr Asp Ile Glu Met Asn Pro Leu Gly Leu Trp
                500                 505                 510

Ala Leu Trp Trp Glu Glu Val Gly Asp Cys Tyr Glu Arg Glu Asp Val
                515                 520                 525

Gln Lys Lys Thr Phe Thr Lys Trp Val Asn Ala Gln Phe Ser Lys Phe
                530                 535                 540

Gly Lys Gln His Ile Glu Asn Leu Phe Ser Asp Leu Gln Asp Gly Arg
545                 550                 555                 560

Arg Leu Leu Asp Leu Leu Glu Gly Leu Thr Gly Gln Lys Leu Pro Lys
                565                 570                 575

Glu Lys Gly Ser Thr Arg Val His Ala Leu Asn Asn Val Asn Lys Ala
                580                 585                 590

Leu Arg Val Leu Gln Asn Asn Asn Val Asp Leu Val Asn Ile Gly Ser
                595                 600                 605

Thr Asp Ile Val Asp Gly Asn His Lys Leu Thr Leu Gly Leu Ile Trp
610                 615                 620

Asn Ile Ile Leu His Trp Gln Val Lys Asn Val Met Lys Asn Ile Met
625                 630                 635                 640

Ala Gly Leu Gln Gln Thr Asn Ser Glu Lys Ile Leu Leu Ser Trp Val
                645                 650                 655

Arg Gln Ser Thr Arg Asn Tyr Pro Gln Val Asn Val Ile Asn Phe Thr
                660                 665                 670

Thr Ser Trp Ser Asp Gly Leu Ala Leu Asn Ala Leu Ile His Ser His
                675                 680                 685

Arg Pro Asp Leu Phe Asp Trp Asn Ser Val Val Cys Gln Gln Ser Ala
                690                 695                 700

Thr Gln Arg Leu Glu His Ala Phe Asn Ile Ala Arg Tyr Gln Leu Gly
705                 710                 715                 720
```

-continued

```
Ile Glu Lys Leu Leu Asp Pro Glu Asp Val Asp Thr Thr Tyr Pro Asp
                725                 730                 735
Lys Lys Ser Ile Leu Met Tyr Ile Thr Ser Leu Phe Gln Val Leu Pro
            740                 745                 750
Gln Gln Val Ser Ile Glu Ala Ile Gln Glu Val Glu Met Leu Pro Arg
        755                 760                 765
Pro Pro Lys Val Thr Lys Glu Glu His Phe Gln Leu His His Gln Met
    770                 775                 780
His Tyr Ser Gln Gln Ile Thr Val Ser Leu Ala Gln Gly Tyr Glu Arg
785                 790                 795                 800
Thr Ser Ser Pro Lys Pro Arg Phe Lys Ser Tyr Ala Tyr Thr Gln Ala
                805                 810                 815
Ala Tyr Val Thr Thr Ser Asp Pro Thr Arg Ser Pro Phe Pro Ser Gln
            820                 825                 830
His Leu Glu Ala Pro Glu Asp Lys Ser Phe Gly Ser Ser Leu Met Glu
        835                 840                 845
Ser Glu Val Asn Leu Asp Arg Tyr Gln Thr Ala Leu Glu Glu Val Leu
    850                 855                 860
Ser Trp Leu Leu Ser Ala Glu Asp Thr Leu Gln Ala Gln Gly Glu Ile
865                 870                 875                 880
Ser Asn Asp Val Glu Val Val Lys Asp Gln Phe His Thr His Glu Gly
                885                 890                 895
Tyr Met Met Asp Leu Thr Ala His Gln Gly Arg Val Gly Asn Ile Leu
            900                 905                 910
Gln Leu Gly Ser Lys Leu Ile Gly Thr Gly Lys Leu Ser Glu Asp Glu
        915                 920                 925
Glu Thr Glu Val Gln Glu Gln Met Asn Leu Leu Asn Ser Arg Trp Glu
    930                 935                 940
Cys Leu Arg Val Ala Ser Met Glu Lys Gln Ser Asn Leu His Arg Val
945                 950                 955                 960
Leu Met Asp Leu Gln Asn Gln Lys Leu Lys Glu Leu Asn Asp Trp Leu
                965                 970                 975
Thr Lys Thr Glu Glu Arg Thr Arg Lys Met Glu Glu Pro Leu Gly
            980                 985                 990
Pro Asp Leu Glu Asp Leu Lys Arg  Gln Val Gln Gln His  Lys Val Leu
        995                 1000                1005
Gln Glu  Asp Leu Glu Gln Glu  Gln Val Arg Val Asn  Ser Leu Thr
    1010                1015                1020
His Met  Val Val Val Val Asp  Glu Ser Ser Gly Asp  His Ala Thr
    1025                1030                1035
Ala Ala  Leu Glu Glu Gln Leu  Lys Val Leu Gly Asp  Arg Trp Ala
    1040                1045                1050
Asn Ile  Cys Arg Trp Thr Glu  Asp Arg Trp Val Leu  Leu Gln Asp
    1055                1060                1065
Ile Leu  Leu Lys Trp Gln Arg  Leu Thr Glu Glu Gln  Cys Leu Phe
    1070                1075                1080
Ser Ala  Trp Leu Ser Glu Lys  Glu Asp Ala Val Asn  Lys Ile His
    1085                1090                1095
Thr Thr  Gly Phe Lys Asp Gln  Asn Glu Met Leu Ser  Ser Leu Gln
    1100                1105                1110
Lys Leu  Ala Val Leu Lys Ala  Asp Leu Glu Lys Lys  Lys Gln Ser
    1115                1120                1125
```

-continued

```
Met Gly Lys Leu Tyr Ser Leu Lys Gln Asp Leu Leu Ser Thr Leu
    1130                1135                1140
Lys Asn Lys Ser Val Thr Gln Lys Thr Glu Ala Trp Leu Asp Asn
    1145                1150                1155
Phe Ala Arg Cys Trp Asp Asn Leu Val Gln Lys Leu Glu Lys Ser
    1160                1165                1170
Thr Ala Gln Ile Ser Gln Ala Val Thr Thr Gln Pro Ser Leu
    1175                1180                1185
Thr Gln Thr Thr Val Met Glu Thr Val Thr Val Thr Thr Arg
    1190                1195                1200
Glu Gln Ile Leu Val Lys His Ala Gln Glu Leu Pro Pro Pro
    1205                1210                1215
Pro Pro Gln Lys Lys Arg Gln Ile Thr Val Asp Ser Glu Ile Arg
    1220                1225                1230
Lys Arg Leu Asp Val Asp Ile Thr Glu Leu His Ser Trp Ile Thr
    1235                1240                1245
Arg Ser Glu Ala Val Leu Gln Ser Pro Glu Phe Ala Ile Phe Arg
    1250                1255                1260
Lys Glu Gly Asn Phe Ser Asp Leu Lys Glu Lys Val Asn Ala Ile
    1265                1270                1275
Glu Arg Glu Lys Ala Glu Lys Phe Arg Lys Leu Gln Asp Ala Ser
    1280                1285                1290
Arg Ser Ala Gln Ala Leu Val Glu Gln Met Val Asn Glu Gly Val
    1295                1300                1305
Asn Ala Asp Ser Ile Lys Gln Ala Ser Glu Gln Leu Asn Ser Arg
    1310                1315                1320
Trp Ile Glu Phe Cys Gln Leu Leu Ser Glu Arg Leu Asn Trp Leu
    1325                1330                1335
Glu Tyr Gln Asn Asn Ile Ile Ala Phe Tyr Asn Gln Leu Gln Gln
    1340                1345                1350
Leu Glu Gln Met Thr Thr Thr Ala Glu Asn Trp Leu Lys Ile Gln
    1355                1360                1365
Pro Thr Thr Pro Ser Glu Pro Thr Ala Ile Lys Ser Gln Leu Lys
    1370                1375                1380
Ile Cys Lys Asp Glu Val Asn Arg Leu Ser Gly Leu Gln Pro Gln
    1385                1390                1395
Ile Glu Arg Leu Lys Ile Gln Ser Ile Ala Leu Lys Glu Lys Gly
    1400                1405                1410
Gln Gly Pro Met Phe Leu Asp Ala Asp Phe Val Ala Phe Thr Asn
    1415                1420                1425
His Phe Lys Gln Val Phe Ser Asp Val Gln Ala Arg Glu Lys Glu
    1430                1435                1440
Leu Gln Thr Ile Phe Asp Thr Leu Pro Pro Met Arg Tyr Gln Glu
    1445                1450                1455
Thr Met Ser Ala Ile Arg Thr Trp Val Gln Ser Glu Thr Lys
    1460                1465                1470
Leu Ser Ile Pro Gln Leu Ser Val Thr Asp Tyr Glu Ile Met Glu
    1475                1480                1485
Gln Arg Leu Gly Glu Leu Gln Ala Leu Gln Ser Ser Leu Gln Glu
    1490                1495                1500
Gln Gln Ser Gly Leu Tyr Tyr Leu Ser Thr Thr Val Lys Glu Met
    1505                1510                1515
Ser Lys Lys Ala Pro Ser Glu Ile Ser Arg Lys Tyr Gln Ser Glu
```

-continued

```
            1520                1525                1530

Phe Glu Glu Ile Glu Gly Arg Trp Lys Lys Leu Ser Ser Gln Leu
            1535                1540                1545

Val Glu His Cys Gln Lys Leu Glu Glu Gln Met Asn Lys Leu Arg
            1550                1555                1560

Lys Ile Gln Asn His Ile Gln Thr Leu Lys Lys Trp Met Ala Glu
            1565                1570                1575

Val Asp Val Phe Leu Lys Glu Glu Trp Pro Ala Leu Gly Asp Ser
            1580                1585                1590

Glu Ile Leu Lys Lys Gln Leu Lys Gln Cys Arg Leu Leu Val Ser
            1595                1600                1605

Asp Ile Gln Thr Ile Gln Pro Ser Leu Asn Ser Val Asn Glu Gly
            1610                1615                1620

Gly Gln Lys Ile Lys Asn Glu Ala Glu Pro Glu Phe Ala Ser Arg
            1625                1630                1635

Leu Glu Thr Glu Leu Lys Glu Leu Asn Thr Gln Trp Asp His Met
            1640                1645                1650

Cys Gln Gln Val Tyr Ala Arg Lys Glu Ala Leu Lys Gly Gly Leu
            1655                1660                1665

Glu Lys Thr Val Ser Leu Gln Lys Asp Leu Ser Glu Met His Glu
            1670                1675                1680

Trp Met Thr Gln Ala Glu Glu Glu Tyr Leu Glu Arg Asp Phe Glu
            1685                1690                1695

Tyr Lys Thr Pro Asp Glu Leu Gln Lys Ala Val Glu Glu Met Lys
            1700                1705                1710

Arg Ala Lys Glu Glu Ala Gln Gln Lys Glu Ala Lys Val Lys Leu
            1715                1720                1725

Leu Thr Glu Ser Val Asn Ser Val Ile Ala Gln Ala Pro Pro Val
            1730                1735                1740

Ala Gln Glu Ala Leu Lys Lys Glu Leu Glu Thr Leu Thr Thr Asn
            1745                1750                1755

Tyr Gln Trp Leu Cys Thr Arg Leu Asn Gly Lys Cys Lys Thr Leu
            1760                1765                1770

Glu Glu Val Trp Ala Cys Trp His Glu Leu Leu Ser Tyr Leu Glu
            1775                1780                1785

Lys Ala Asn Lys Trp Leu Asn Glu Val Glu Phe Lys Leu Lys Thr
            1790                1795                1800

Thr Glu Asn Ile Pro Gly Gly Ala Glu Glu Ile Ser Glu Val Leu
            1805                1810                1815

Asp Ser Leu Glu Asn Leu Met Arg His Ser Glu Asp Asn Pro Asn
            1820                1825                1830

Gln Ile Arg Ile Leu Ala Gln Thr Leu Thr Asp Gly Gly Val Met
            1835                1840                1845

Asp Glu Leu Ile Asn Glu Glu Leu Glu Thr Phe Asn Ser Arg Trp
            1850                1855                1860

Arg Glu Leu His Glu Glu Ala Val Arg Arg Gln Lys Leu Leu Glu
            1865                1870                1875

Gln Ser Ile Gln Ser Ala Gln Glu Thr Glu Lys Ser Leu His Leu
            1880                1885                1890

Ile Gln Glu Ser Leu Thr Phe Ile Asp Lys Gln Leu Ala Ala Tyr
            1895                1900                1905

Ile Ala Asp Lys Val Asp Ala Ala Gln Met Pro Gln Glu Ala Gln
            1910                1915                1920
```

```
Lys Ile Gln Ser Asp Leu Thr Ser His Glu Ile Ser Leu Glu Glu
    1925                1930                1935

Met Lys Lys His Asn Gln Gly Lys Glu Ala Ala Gln Arg Val Leu
    1940                1945                1950

Ser Gln Ile Asp Val Ala Gln Lys Lys Leu Gln Asp Val Ser Met
    1955                1960                1965

Lys Phe Arg Leu Phe Gln Lys Pro Ala Asn Phe Glu Leu Arg Leu
    1970                1975                1980

Gln Glu Ser Lys Met Ile Leu Asp Glu Val Lys Met His Leu Pro
    1985                1990                1995

Ala Leu Glu Thr Lys Ser Val Glu Gln Glu Val Val Gln Ser Gln
    2000                2005                2010

Leu Asn His Cys Val Asn Leu Tyr Lys Ser Leu Ser Glu Val Lys
    2015                2020                2025

Ser Glu Val Glu Met Val Ile Lys Thr Gly Arg Gln Ile Val Gln
    2030                2035                2040

Lys Lys Gln Thr Glu Asn Pro Lys Glu Leu Asp Glu Arg Val Thr
    2045                2050                2055

Ala Leu Lys Leu His Tyr Asn Glu Leu Gly Ala Lys Val Thr Glu
    2060                2065                2070

Arg Lys Gln Gln Leu Glu Lys Cys Leu Lys Leu Ser Arg Lys Met
    2075                2080                2085

Arg Lys Glu Met Asn Val Leu Thr Glu Trp Leu Ala Ala Thr Asp
    2090                2095                2100

Met Glu Leu Thr Lys Arg Ser Ala Val Glu Gly Met Pro Ser Asn
    2105                2110                2115

Leu Asp Ser Glu Val Ala Trp Gly Lys Ala Thr Gln Lys Glu Ile
    2120                2125                2130

Glu Lys Gln Lys Val His Leu Lys Ser Ile Thr Glu Val Gly Glu
    2135                2140                2145

Ala Leu Lys Thr Val Leu Gly Lys Lys Glu Thr Leu Val Glu Asp
    2150                2155                2160

Lys Leu Ser Leu Leu Asn Ser Asn Trp Ile Ala Val Thr Ser Arg
    2165                2170                2175

Ala Glu Glu Trp Leu Asn Leu Leu Leu Glu Tyr Gln Lys His Met
    2180                2185                2190

Glu Thr Phe Asp Gln Asn Val Asp His Ile Thr Lys Trp Ile Ile
    2195                2200                2205

Gln Ala Asp Thr Leu Leu Asp Glu Ser Glu Lys Lys Lys Pro Gln
    2210                2215                2220

Gln Lys Glu Asp Val Leu Lys Arg Leu Lys Ala Glu Leu Asn Asp
    2225                2230                2235

Ile Arg Pro Lys Val Asp Ser Thr Arg Asp Gln Ala Ala Asn Leu
    2240                2245                2250

Met Ala Asn Arg Gly Asp His Cys Arg Lys Leu Val Glu Pro Gln
    2255                2260                2265

Ile Ser Glu Leu Asn His Arg Phe Ala Ala Ile Ser His Arg Ile
    2270                2275                2280

Lys Thr Gly Lys Ala Ser Ile Pro Leu Lys Glu Leu Glu Gln Phe
    2285                2290                2295

Asn Ser Asp Ile Gln Lys Leu Leu Glu Pro Leu Glu Ala Glu Ile
    2300                2305                2310
```

```
Gln Gln Gly Val Asn Leu Lys Glu Glu Asp Phe Asn Lys Asp Met
    2315                2320                2325

Asn Glu Asp Asn Glu Gly Thr Val Lys Glu Leu Leu Gln Arg Gly
    2330                2335                2340

Asp Asn Leu Gln Gln Arg Ile Thr Asp Glu Arg Lys Arg Glu Glu
    2345                2350                2355

Ile Lys Ile Lys Gln Gln Leu Leu Gln Thr Lys His Asn Ala Leu
    2360                2365                2370

Lys Asp Leu Arg Ser Gln Arg Arg Lys Lys Ala Leu Glu Ile Ser
    2375                2380                2385

His Gln Trp Tyr Gln Tyr Lys Arg Gln Ala Asp Asp Leu Leu Lys
    2390                2395                2400

Cys Leu Asp Asp Ile Glu Lys Lys Leu Ala Ser Leu Pro Glu Pro
    2405                2410                2415

Arg Asp Glu Arg Lys Ile Lys Glu Ile Asp Arg Glu Leu Gln Lys
    2420                2425                2430

Lys Lys Glu Glu Leu Asn Ala Val Arg Arg Gln Ala Glu Gly Leu
    2435                2440                2445

Ser Glu Asp Gly Ala Ala Met Ala Val Glu Pro Thr Gln Ile Gln
    2450                2455                2460

Leu Ser Lys Arg Trp Arg Glu Ile Glu Ser Lys Phe Ala Gln Phe
    2465                2470                2475

Arg Arg Leu Asn Phe Ala Gln Ile His Thr Val Arg Glu Glu Thr
    2480                2485                2490

Met Met Val Met Thr Glu Asp Met Pro Leu Glu Ile Ser Tyr Val
    2495                2500                2505

Pro Ser Thr Tyr Leu Thr Glu Ile Thr His Val Ser Gln Ala Leu
    2510                2515                2520

Leu Glu Val Glu Gln Leu Leu Asn Ala Pro Asp Leu Cys Ala Lys
    2525                2530                2535

Asp Phe Glu Asp Leu Phe Lys Gln Glu Glu Ser Leu Lys Asn Ile
    2540                2545                2550

Lys Asp Ser Leu Gln Gln Ser Ser Gly Arg Ile Asp Ile Ile His
    2555                2560                2565

Ser Lys Lys Thr Ala Ala Leu Gln Ser Ala Thr Pro Val Glu Arg
    2570                2575                2580

Val Lys Leu Gln Glu Ala Leu Ser Gln Leu Asp Phe Gln Trp Glu
    2585                2590                2595

Lys Val Asn Lys Met Tyr Lys Asp Arg Gln Gly Arg Phe Asp Arg
    2600                2605                2610

Ser Val Glu Lys Trp Arg Arg Phe His Tyr Asp Ile Lys Ile Phe
    2615                2620                2625

Asn Gln Trp Leu Thr Glu Ala Glu Gln Phe Leu Arg Lys Thr Gln
    2630                2635                2640

Ile Pro Glu Asn Trp Glu His Ala Lys Tyr Lys Trp Tyr Leu Lys
    2645                2650                2655

Glu Leu Gln Asp Gly Ile Gly Gln Arg Gln Thr Val Val Arg Thr
    2660                2665                2670

Leu Asn Ala Thr Gly Glu Glu Ile Ile Gln Gln Ser Ser Lys Thr
    2675                2680                2685

Asp Ala Ser Ile Leu Gln Glu Lys Leu Gly Ser Leu Asn Leu Arg
    2690                2695                2700

Trp Gln Glu Val Cys Lys Gln Leu Ser Asp Arg Lys Lys Arg Leu
```

-continued

```
                2705                2710                2715
Glu Glu Gln Lys Asn Ile Leu Ser Glu Phe Gln Arg Asp Leu Asn
        2720                2725                2730
Glu Phe Val Leu Trp Leu Glu Glu Ala Asp Asn Ile Ala Ser Ile
        2735                2740                2745
Pro Leu Glu Pro Gly Lys Glu Gln Gln Leu Lys Glu Lys Leu Glu
        2750                2755                2760
Gln Val Lys Leu Leu Val Glu Glu Leu Pro Leu Arg Gln Gly Ile
        2765                2770                2775
Leu Lys Gln Leu Asn Glu Thr Gly Gly Pro Val Leu Val Ser Ala
        2780                2785                2790
Pro Ile Ser Pro Glu Glu Gln Asp Lys Leu Glu Asn Lys Leu Lys
        2795                2800                2805
Gln Thr Asn Leu Gln Trp Ile Lys Val Ser Arg Ala Leu Pro Glu
        2810                2815                2820
Lys Gln Gly Glu Ile Glu Ala Gln Ile Lys Asp Leu Gly Gln Leu
        2825                2830                2835
Glu Lys Lys Leu Glu Asp Leu Glu Glu Gln Leu Asn His Leu Leu
        2840                2845                2850
Leu Trp Leu Ser Pro Ile Arg Asn Gln Leu Glu Ile Tyr Asn Gln
        2855                2860                2865
Pro Asn Gln Glu Gly Pro Phe Asp Val Gln Glu Thr Glu Ile Ala
        2870                2875                2880
Val Gln Ala Lys Gln Pro Asp Val Glu Glu Ile Leu Ser Lys Gly
        2885                2890                2895
Gln His Leu Tyr Lys Glu Lys Pro Ala Thr Gln Pro Val Lys Arg
        2900                2905                2910
Lys Leu Glu Asp Leu Ser Ser Glu Trp Lys Ala Val Asn Arg Leu
        2915                2920                2925
Leu Gln Glu Leu Arg Ala Lys Gln Pro Asp Leu Ala Pro Gly Leu
        2930                2935                2940
Thr Thr Ile Gly Ala Ser Pro Thr Gln Thr Val Thr Leu Val Thr
        2945                2950                2955
Gln Pro Val Val Thr Lys Glu Thr Ala Ile Ser Lys Leu Glu Met
        2960                2965                2970
Pro Ser Ser Leu Met Leu Glu Val Pro Ala Leu Ala Asp Phe Asn
        2975                2980                2985
Arg Ala Trp Thr Glu Leu Thr Asp Trp Leu Ser Leu Leu Asp Gln
        2990                2995                3000
Val Ile Lys Ser Gln Arg Val Met Val Gly Asp Leu Glu Asp Ile
        3005                3010                3015
Asn Glu Met Ile Ile Lys Gln Lys Ala Thr Met Gln Asp Leu Glu
        3020                3025                3030
Gln Arg Arg Pro Gln Leu Glu Glu Leu Ile Thr Ala Ala Gln Asn
        3035                3040                3045
Leu Lys Asn Lys Thr Ser Asn Gln Glu Ala Arg Thr Ile Ile Thr
        3050                3055                3060
Asp Arg Ile Glu Arg Ile Gln Asn Gln Trp Asp Glu Val Gln Glu
        3065                3070                3075
His Leu Gln Asn Arg Arg Gln Gln Leu Asn Glu Met Leu Lys Asp
        3080                3085                3090
Ser Thr Gln Trp Leu Glu Ala Lys Glu Glu Ala Glu Gln Val Leu
        3095                3100                3105
```

-continued

Gly Gln Ala Arg Ala Lys Leu Glu Ser Trp Lys Glu Gly Pro Tyr
3110            3115                3120

Thr Val Asp Ala Ile Gln Lys Lys Ile Thr Glu Thr Lys Gln Leu
3125            3130                3135

Ala Lys Asp Leu Arg Gln Trp Gln Thr Asn Val Asp Val Ala Asn
3140            3145                3150

Asp Leu Ala Leu Lys Leu Leu Arg Asp Tyr Ser Ala Asp Asp Thr
3155            3160                3165

Arg Lys Val His Met Ile Thr Glu Asn Ile Asn Ala Ser Trp Arg
3170            3175                3180

Ser Ile His Lys Arg Val Ser Glu Arg Glu Ala Ala Leu Glu Glu
3185            3190                3195

Thr His Arg Leu Leu Gln Gln Phe Pro Leu Asp Leu Glu Lys Phe
3200            3205                3210

Leu Ala Trp Leu Thr Glu Ala Glu Thr Thr Ala Asn Val Leu Gln
3215            3220                3225

Asp Ala Thr Arg Lys Glu Arg Leu Leu Glu Asp Ser Lys Gly Val
3230            3235                3240

Lys Glu Leu Met Lys Gln Trp Gln Asp Leu Gln Gly Glu Ile Glu
3245            3250                3255

Ala His Thr Asp Val Tyr His Asn Leu Asp Glu Asn Ser Gln Lys
3260            3265                3270

Ile Leu Arg Ser Leu Glu Gly Ser Asp Asp Ala Val Leu Leu Gln
3275            3280                3285

Arg Arg Leu Asp Asn Met Asn Phe Lys Trp Ser Glu Leu Arg Lys
3290            3295                3300

Lys Ser Leu Asn Ile Arg Ser His Leu Glu Ala Ser Ser Asp Gln
3305            3310                3315

Trp Lys Arg Leu His Leu Ser Leu Gln Glu Leu Leu Val Trp Leu
3320            3325                3330

Gln Leu Lys Asp Asp Glu Leu Ser Arg Gln Ala Pro Ile Gly Gly
3335            3340                3345

Asp Phe Pro Ala Val Gln Lys Gln Asn Asp Val His Arg Ala Phe
3350            3355                3360

Lys Arg Glu Leu Lys Thr Lys Glu Pro Val Ile Met Ser Thr Leu
3365            3370                3375

Glu Thr Val Arg Ile Phe Leu Thr Glu Gln Pro Leu Glu Gly Leu
3380            3385                3390

Glu Lys Leu Tyr Gln Glu Pro Arg Glu Leu Pro Pro Glu Glu Arg
3395            3400                3405

Ala Gln Asn Val Thr Arg Leu Leu Arg Lys Gln Ala Glu Glu Val
3410            3415                3420

Asn Thr Glu Trp Glu Lys Leu Asn Leu His Ser Ala Asp Trp Gln
3425            3430                3435

Arg Lys Ile Asp Glu Thr Leu Glu Arg Leu Gln Glu Leu Gln Glu
3440            3445                3450

Ala Thr Asp Glu Leu Asp Leu Lys Leu Arg Gln Ala Glu Val Ile
3455            3460                3465

Lys Gly Ser Trp Gln Pro Val Gly Asp Leu Leu Ile Asp Ser Leu
3470            3475                3480

Gln Asp His Leu Glu Lys Val Lys Ala Leu Arg Gly Glu Ile Ala
3485            3490                3495

```
Pro Leu Lys Glu Asn Val Ser His Val Asn Asp Leu Ala Arg Gln
3500                3505                3510

Leu Thr Thr Leu Gly Ile Gln Leu Ser Pro Tyr Asn Leu Ser Thr
    3515                3520                3525

Leu Glu Asp Leu Asn Thr Arg Trp Lys Leu Leu Gln Val Ala Val
3530                3535                3540

Glu Asp Arg Val Arg Gln Leu His Glu Ala His Arg Asp Phe Gly
3545                3550                3555

Pro Ala Ser Gln His Phe Leu Ser Thr Ser Val Gln Gly Pro Trp
3560                3565                3570

Glu Arg Ala Ile Ser Pro Asn Lys Val Pro Tyr Tyr Ile Asn His
3575                3580                3585

Glu Thr Gln Thr Thr Cys Trp Asp His Pro Lys Met Thr Glu Leu
3590                3595                3600

Tyr Gln Ser Leu Ala Asp Leu Asn Asn Val Arg Phe Ser Ala Tyr
3605                3610                3615

Arg Thr Ala Met Lys Leu Arg Arg Leu Gln Lys Ala Leu Cys Leu
3620                3625                3630

Asp Leu Leu Ser Leu Ser Ala Ala Cys Asp Ala Leu Asp Gln His
3635                3640                3645

Asn Leu Lys Gln Asn Asp Gln Pro Met Asp Ile Leu Gln Ile Ile
3650                3655                3660

Asn Cys Leu Thr Thr Ile Tyr Asp Arg Leu Glu Gln Glu His Asn
3665                3670                3675

Asn Leu Val Asn Val Pro Leu Cys Val Asp Met Cys Leu Asn Trp
3680                3685                3690

Leu Leu Asn Val Tyr Asp Thr Gly Arg Thr Gly Arg Ile Arg Val
3695                3700                3705

Leu Ser Phe Lys Thr Gly Ile Ile Ser Leu Cys Lys Ala His Leu
3710                3715                3720

Glu Asp Lys Tyr Arg Tyr Leu Phe Lys Gln Val Ala Ser Ser Thr
3725                3730                3735

Gly Phe Cys Asp Gln Arg Arg Leu Gly Leu Leu Leu His Asp Ser
3740                3745                3750

Ile Gln Ile Pro Arg Gln Leu Gly Glu Val Ala Ser Phe Gly Gly
3755                3760                3765

Ser Asn Ile Glu Pro Ser Val Arg Ser Cys Phe Gln Phe Ala Asn
3770                3775                3780

Asn Lys Pro Glu Ile Glu Ala Ala Leu Phe Leu Asp Trp Met Arg
3785                3790                3795

Leu Glu Pro Gln Ser Met Val Trp Leu Pro Val Leu His Arg Val
3800                3805                3810

Ala Ala Ala Glu Thr Ala Lys His Gln Ala Lys Cys Asn Ile Cys
3815                3820                3825

Lys Glu Cys Pro Ile Ile Gly Phe Arg Tyr Arg Ser Leu Lys His
3830                3835                3840

Phe Asn Tyr Asp Ile Cys Gln Ser Cys Phe Phe Ser Gly Arg Val
3845                3850                3855

Ala Lys Gly His Lys Met His Tyr Pro Met Val Glu Tyr Cys Thr
3860                3865                3870

Pro Thr Thr Ser Gly Glu Asp Val Arg Asp Phe Ala Lys Val Leu
3875                3880                3885

Lys Asn Lys Phe Arg Thr Lys Arg Tyr Phe Ala Lys His Pro Arg
```

Met Gly Tyr Leu Pro Val Gln Thr Val Leu Glu Gly Asp Asn Met
3905                3910                3915

Glu Thr Pro Val Thr Leu Ile Asn Phe Trp Pro Val Asp Ser Ala
3920                3925                3930

Pro Ala Ser Ser Pro Gln Leu Ser His Asp Asp Thr His Ser Arg
3935                3940                3945

Ile Glu His Tyr Ala Ser Arg Leu Ala Glu Met Glu Asn Ser Asn
3950                3955                3960

Gly Ser Tyr Leu Asn Asp Ser Ile Ser Pro Asn Glu Ser Ile Asp
3965                3970                3975

Asp Glu His Leu Leu Ile Gln His Tyr Cys Gln Ser Leu Asn Gln
3980                3985                3990

Asp Ser Pro Leu Ser Gln Pro Arg Ser Pro Ala Gln Ile Leu Ile
3995                4000                4005

Ser Leu Glu Ser Glu Glu Arg Gly Glu Leu Glu Arg Ile Leu Ala
4010                4015                4020

Asp Leu Glu Glu Glu Asn Arg Asn Leu Gln Ala Glu Tyr Asp Arg
4025                4030                4035

Leu Lys Gln Gln His Glu His Lys Gly Leu Ser Pro Leu Pro Ser
4040                4045                4050

Pro Pro Glu Met Met Pro Thr Ser Pro Gln Ser Pro Arg Asp Ala
4055                4060                4065

Glu Leu Ile Ala Glu Ala Lys Leu Leu Arg Gln His Lys Gly Arg
4070                4075                4080

Leu Glu Ala Arg Met Gln Ile Leu Glu Asp His Asn Lys Gln Leu
4085                4090                4095

Glu Ser Gln Leu His Arg Leu Arg Gln Leu Leu Glu Gln Pro Gln
4100                4105                4110

Ala Glu Ala Lys Val Asn Gly Thr Thr Val Ser Ser Pro Ser Thr
4115                4120                4125

Ser Leu Gln Arg Ser Asp Ser Ser Gln Pro Met Leu Leu Arg Val
4130                4135                4140

Val Gly Ser Gln Thr Ser Asp Ser Met Gly Glu Glu Asp Leu Leu
4145                4150                4155

Ser Pro Pro Gln Asp Thr Ser Thr Gly Leu Glu Glu Val Met Glu
4160                4165                4170

Gln Leu Asn Asn Ser Phe Pro Ser Ser Arg Gly Arg Asn Thr Pro
4175                4180                4185

Gly Lys Pro Met Arg Glu Asp Thr Met
4190                4195

<210> SEQ ID NO 3
<211> LENGTH: 7488
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic nucleotide sequence of proposed Dystrophin (truncated)
      -VSV-G chimeric protein with VSV-G at N-terminal"

<400> SEQUENCE: 3
atgaagtgcc ttttgtactt agctttttta ttcatcgggg tgaattgcaa gttcaccata      60
gttttttcca caacccaaaa aggaaactgg aaaaatgttc cttccaatta ccattattgc     120

```
ccgtcaagct cagatttaaa ttggcataat gacttaatag gcacagcctt acaagtcaaa    180
atgcccaaga gtcacaaggc tattcaagca gacggttgga tgtgtcatgc ttccaaatgg    240
gtcactactt gtgatttccg ctggtacgga ccgaagtata acacattc catccgatcc      300 ttcactccat ctgtagaaca atgcaaggaa agcattgaac aaacgaaaca aggaacttgg    360
ctgaatccag gcttccctcc tcaaagttgt ggatatgcaa ctgtgacgga tgctgaagca    420
gcgattgtcc aggtgactcc tcaccatgtg cttgttgatg aatacacagg agaatgggtt    480
gattcacagt tcatcaacgg aaaatgcagc aatgacatat gccccactgt ccataactcc    540
acaacctggc attccgacta aaggtcaaa gggctatgtg attctaacct catttccacg     600
gacatcacct tcttctcaga ggacggagag ctatcatccc taggaaagga gggcacaggg    660
ttcagaagta actactttgc ttatgaaact ggagacaagg cctgcaaaat gcagtactgc    720
aagcattggg gagtcagact cccatcaggt gtctggttcg agatggctga taaggatctc    780
tttgctgcag ccagattccc tgaatgccca aagggtcaa gtatctctgc tccatctcag     840
acctcagtgg atgtaagtct cattcaggac gttgagagga tcttggatta ttccctctgc    900
caagaaacct ggagcaaaat cagagcgggt cttcccatct ctccagtgga tctcagctat    960
cttgctccta aaaacccagg aaccggtcct gtctttacca taatcaatgg tacccctaaaa  1020 tactttgaga ccagatacat cagagtcgat attgctgctc caatcctctc aagaatggtc    1080
ggaatgatca gtgaactac cacagaaagg gaactgtggg atgactgggc tccatatgaa     1140
gacgtggaaa ttggacccaa tggagttctg aggaccagtt taggatataa gtttccttta    1200
tatatgattg acatggtat gttggactcc gatcttcatc ttagctcaaa ggctcaggtg      1260
tttgaacatc ctcacattca agacgctgct tcgcagcttc ctgatgatga gactttatt     1320 tttggtgata ctgggctatc caaaaatcca atcgagtttg tagaaggttg gttcagtagt    1380
tggaagagct ctattgcctc ttttttcttt atcatagggt taatcattgg actattcttg    1440
gttctccgag ttggtattta tctttgcatt aaattaaagc acaccaagaa aagacagatt    1500
tatacagaca tagagatgaa cccacttgga ctgtgggcgc tttggtggga agaagtagag    1560
gactgttatg aaagagaaga tgttcaaaag aaaacattca caaatgggt aaatgcacaa    1620 ttttctaagt ttgggaagca gcatattgag aacctcttca gtgacctaca ggatgggagg    1680
cgcctcctag acctcctcga aggcctgaca gggcaaaaac tgccaaaaga aaaggatcc    1740 acaagagttc atgccctgaa caatgtcaac aaggcactgc gggttttgca gaacaataat    1800
gttgatttag tgaatattgg aagtactgac atcgtagatg gaaatcataa actgactctt    1860
ggtttgattt ggaatataat cctccactgg caggtcaaaa atgtaatgaa aaatatcatg    1920
gctggattgc aacaaccaa cagtgaaaag attctcctga ctgggtccg acaatcaact     1980 cgtaattatc cacaggttaa tgtaatcaac ttcaccacca gctggtctga tggcctggct    2040
ttgaatgctc tcatccatag tcataggcca gacctatttg actggaatag tgtggtttgc    2100
cagcagtcag ccacacaacg actggaacat gcattcaaca tcgccagata tcaattaggc    2160
atagagaaac tactcgatcc tgaagatgtt gataccacct atccagataa gaagtccatc    2220
ttaatgtaca tcatcact cttccaagtt ttgcctcaac aagtgagcat tgaagccatc     2280
caggaagtgg aaatgttgcc aaggccacct aaagtgacta agaagaaca ttttcagtta    2340 catcatcaaa tgcactattc tcaacagatc acggtcagtc tagcacaggg atatgagaga    2400
acttcttccc ctaagcctcg attcaagagc tatgcctaca cacaggctgc ttatgtcacc    2460
acctctgacc ctacacggag cccatttcct tcacagcatt tggaagctcc tgaagacaag    2520
```

```
tcatttggca gttcattgat ggagagtgaa gtaaacctgg accgttatca aacagcttta    2580
gaagaagtat tatcgtggct tctttctgct gaggacacat tgcaagcaca aggagagatt    2640
tctaatgatg tggaagtggt gaaagaccag tttcatactc atgagggta catgatggat     2700 ttgacagccc atcagggccg ggttggtaat attctacaat tgggaagtaa gctgattgga    2760
acaggaaaat tatcagaaga tgaagaaact gaagtacaag agcagatgaa tctcctaaat    2820
tcaagatggg aatgcctcag ggtagctagc atggaaaaac aaagcaattt acatagagtt    2880
ttaatggatc tccagaatca gaaactgaaa gagttgaatg actggctaac aaaaacagaa    2940
gaaagaacaa ggaaaatgga ggaagagcct cttggacctg atcttgaaga cctaaaacgc    3000
caagtacaac aacataaggt gcttcaagaa gatctagaac aagaacaagt cagggtcaat    3060
tctctcactc acatggtggt ggtagttgat gaatctagtg gagatcacgc aactgctgct    3120
ttggaagaac aacttaaggt attgggagat cgatgggcaa acatctgtag atggacagaa    3180
gaccgctggg ttcttttaca agacatcctt ctcaaatggc aacgtcttac tgaagaacag    3240 tgcctttta gtgcatggct ttcagaaaaa gaagatgcag tgaacaagat tcacacaact    3300
ggctttaaag atcaaaatga aatgttatca agtcttcaaa aactggccgt tttaaaagcg    3360
gatctagaaa agaaaaagca atccatgggc aaactgtatt cactcaaaca agatcttctt    3420
tcaacactga gaataagtc agtgacccag aagacggaag catggctgga taactttgcc    3480
cggtgttggg ataatttagt ccaaaaactt gaaaagagta cagcacagga aactgaaata    3540
gcagttcaag ctaaacaacc ggatgtggaa gagattttgt ctaaagggca gcatttgtac    3600
aaggaaaaac cagccactca gccagtgaag aggaagttag aagatctgag ctctgagtgg    3660
aaggcggtaa accgtttact tcaagagctg agggcaaagc agcctgacct agctcctgga    3720
ctgaccacta ttggagcctc tcctactcag actgttactc tggtgacaca acctgtggtt    3780
actaaggaaa ctgccatctc caaactagaa atgccatctt ccttgatgtt ggaggtacct    3840
gctctggcag atttcaaccg ggcttggaca gaacttaccg actggctttc tctgcttgat    3900
caagttataa atcacagag ggtgatggtg ggtgaccttg aggatatcaa cgagatgatc    3960
atcaagcaga aggcaacaat gcaggatttg aacagaggc gtccccagtt ggaagaactc    4020
attaccgctg cccaaaattt gaaaaacaag accagcaatc aagaggctag aacaatcatt    4080
acggatcgaa ttgaaagaat tcagaatcag tgggatgaag tacaagaaca ccttcagaac    4140
cggaggcaac agttgaatga aatgttaaag gattcaacac aatggctgga agctaaggaa    4200
gaagctgagc aggtcttagg acaggccaga gccaagcttg agtcatggaa ggagggtccc    4260
tatacagtag atgcaatcca aaagaaaatc acagaaacca gcagttggc caaagacctc    4320 cgccagtggc agacaaatgt agatgtggca atgactggg ccctgaaact ctccgggat    4380 tattctgcag atgataccag aaaagtccac atgataacag agaatatcaa tgcctcttgg    4440
agaagcattc ataaaagggt gagtgagcga gaggctgctt tggaagaaac tcatagatta    4500
ctgcaacagt tcccctgga cctggaaaag tttcttgcct ggcttacaga agctgaaaca    4560
actgccaatg tcctacagga tgctacccgt aaggaaggc tcctagaaga ctccaaggga    4620
gtaaaagagc tgatgaaaca atggcaagac ctccaaggtg aaattgaagc tcacacagat    4680
gtttatcaca acctggatga aacagccaa aaaatcctga atccctggaa aggttccgat    4740
gatgcagtcc tgttacaaag acgtttggat aacatgaact tcaagtggag tgaacttcgg    4800
aaaaagtctc tcaacattag gtcccatttg gaagccagtt ctgaccagtg gaagcgtctg    4860
```

-continued

```
caccttctc tgcaggaact tctggtgtgg ctacagctga aagatgatga attaagccgg      4920
caggcaccta ttggaggcga ctttccagca gttcagaagc agaacgatgt acatagggcc      4980
ttcaagaggg aattgaaaac taaagaacct gtaatcatga gtactcttga gactgtacga      5040
atatttctga cagagcagcc tttgaagga ctagagaaac tctaccagga gcccagagag       5100
ctgcctcctg aggagagagc ccagaatgtc actcggcttc tacgaaagca ggctgaggag      5160
gtcaatactg agtgggaaaa attgaacctg cactccgctg actggcagag aaaaatagat      5220
gagacccttg aaagactcca ggaacttcaa gaggccacgg atgagctgga cctcaagctg      5280
cgccaagctg aggtgatcaa gggatcctgg cagcccgtgg gcgatctcct cattgactct      5340
ctccaagatc acctcgagaa agtcaaggca cttcgaggag aaattgcgcc tctgaaagag      5400
aacgtgagcc acgtcaatga ccttgctcgc cagcttacca cttttgggcat tcagctctca     5460
ccgtataacc tcagcactct ggaagacctg aacaccagat ggaagcttct gcaggtggcc      5520
gtcgaggacc gagtcaggca gctgcatgaa gcccacaggg actttggtcc agcatctcag      5580
cactttcttt ccacgtctgt ccagggtccc tgggagagag ccatctcgcc aaacaaagtg      5640
ccctactata tcaaccacga gactcaaaca acttgctggg accatcccaa aatgacagag      5700
ctctaccagt ctttagctga cctgaataat gtcagattct cagcttatag gactgccatg      5760
aaactccgaa gactgcagaa ggcccttttgc ttggatctct tgagcctgtc agctgcatgt     5820
gatgccttgg accagcacaa cctcaagcaa aatgaccagc ccatggatat cctgcagatt      5880
attaattgtt tgaccactat ttatgaccgc ctggagcaag agcacaacaa tttggtcaac      5940
gtccctctct gcgtggatat gtgtctgaac tggctgctga atgtttatga tacgggacga      6000
acagggagga tccgtgtcct gtcttttaaa actggcatca tttccctgtg taaagcacat      6060
ttggaagaca agtacagata ccttttcaag caagtggcaa gttcaacagg attttgtgac      6120
cagcgcaggc tgggcctcct tctgcatgat tctatccaaa ttccaagaca gttgggtgaa      6180
gttgcatcct ttgggggcag taacattgag ccaagtgtcc ggagctgctt ccaatttgct      6240
aataataagc cagagatcga agcggccctc ttcctagact ggatgagact ggaaccccag      6300
tccatggtgt ggctgcccgt cctgcacaga gtggctgctg cagaaactgc caagcatcag      6360
gccaaatgta acatctgcaa agagtgtcca atcattggat tcaggtacag gagtctaaag      6420
cactttaatt atgacatctg ccaaagctgc ttttttctg gtcgagttgc aaaaggccat      6480
aaaatgcact atcccatggt ggaatattgc actccgacta catcaggaga gatgttcga       6540
gactttgcca aggtactaaa aaacaaattt cgaaccaaaa ggtatttgc gaagcatccc       6600
cgaatgggct acctgccagt gcagactgtc ttagagggg acaacatgga aactcccgtt       6660
actctgatca acttctggcc agtagattct gcgcctgcct cgtcccctca gctttcacac      6720
gatgatactc attcacgcat tgaacattat gctagcaggc tagcagaaat ggaaaacagc      6780
aatggatctt atctaaatga tagcatctct cctaatgaga gcatagatga tgaacatttg      6840
ttaatccagc attactgcca aagttgaac caggactccc cctgagcca gcctcgtagt        6900
cctgcccaga tcttgatttc cttagagagt gaggaaagag gggagctaga gagaatccta     6960
gcagatcttg aggaagaaaa caggaatctg caagcagaat atgaccgtct aaagcagcag     7020
cacgaacata aaggcctgtc cccactgccg tcccctcctg aaatgatgcc cacctctccc     7080
cagagtcccc gggatgctga gctcattgct gaggccaagc tactgcgtca acacaaaggc      7140
cgcctggaag ccaggatgca aatcctggaa gaccacaata aacagctgga gtcacagtta      7200
cacaggctaa ggcagctgct ggagcaaccc caggcagagg ccaaagtgaa tggcacaacg      7260
```

-continued

```
gtgtcctctc cttctacctc tctacagagg tccgacagca gtcagcctat gctgctccga      7320
gtggttggca gtcaaacttc ggactccatg ggtgaggaag atcttctcag tcctccccag      7380
gacacaagca cagggttaga ggaggtgatg gagcaactca acaactcctt ccctagttca      7440
agaggaagaa ataccctggg aaagccaatg agagaggaca caatgtag                  7488
```

```
<210> SEQ ID NO 4
<211> LENGTH: 2495
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic amino acid sequence of proposed Dystrophin (truncated)
      -VSV-G chimeric protein with VSV-G at N-terminal"

<400> SEQUENCE: 4

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Leu Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Ala Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Thr Asp Ile Thr Phe Phe Ser Glu Asp
        195                 200                 205

Gly Glu Leu Ser Ser Leu Gly Lys Glu Gly Thr Gly Phe Arg Ser Asn
    210                 215                 220

Tyr Phe Ala Tyr Glu Thr Gly Asp Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
    290                 295                 300
```

```
Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Val Phe Thr Ile Ile Asn
            325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Asp Trp Ala Pro Tyr Glu Asp Val Glu Ile
    370                 375                 380

Gly Pro Asn Gly Val Leu Arg Thr Ser Leu Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Thr Leu Phe Phe Gly Asp Thr Gly Leu Ser Lys
        435                 440                 445

Asn Pro Ile Glu Phe Val Glu Gly Trp Phe Ser Ser Trp Lys Ser Ser
450                 455                 460

Ile Ala Ser Phe Phe Ile Ile Gly Leu Ile Ile Gly Leu Phe Leu
465                 470                 475                 480

Val Leu Arg Val Gly Ile Tyr Leu Cys Ile Lys Leu Lys His Thr Lys
                485                 490                 495

Lys Arg Gln Ile Tyr Thr Asp Ile Glu Met Asn Pro Leu Gly Leu Trp
            500                 505                 510

Ala Leu Trp Trp Glu Glu Val Glu Asp Cys Tyr Glu Arg Glu Asp Val
        515                 520                 525

Gln Lys Lys Thr Phe Thr Lys Trp Val Asn Ala Gln Phe Ser Lys Phe
    530                 535                 540

Gly Lys Gln His Ile Glu Asn Leu Phe Ser Asp Leu Gln Asp Gly Arg
545                 550                 555                 560

Arg Leu Leu Asp Leu Leu Glu Gly Leu Thr Gly Gln Lys Leu Pro Lys
                565                 570                 575

Glu Lys Gly Ser Thr Arg Val His Ala Leu Asn Asn Val Asn Lys Ala
            580                 585                 590

Leu Arg Val Leu Gln Asn Asn Asn Val Asp Leu Val Asn Ile Gly Ser
        595                 600                 605

Thr Asp Ile Val Asp Gly Asn His Lys Leu Thr Leu Gly Leu Ile Trp
    610                 615                 620

Asn Ile Ile Leu His Trp Gln Val Lys Asn Val Met Lys Asn Ile Met
625                 630                 635                 640

Ala Gly Leu Gln Gln Thr Asn Ser Glu Lys Ile Leu Leu Ser Trp Val
                645                 650                 655

Arg Gln Ser Thr Arg Asn Tyr Pro Gln Val Asn Val Ile Asn Phe Thr
            660                 665                 670

Thr Ser Trp Ser Asp Gly Leu Ala Leu Asn Ala Leu Ile His Ser His
        675                 680                 685

Arg Pro Asp Leu Phe Asp Trp Asn Ser Val Val Cys Gln Gln Ser Ala
    690                 695                 700

Thr Gln Arg Leu Glu His Ala Phe Asn Ile Ala Arg Tyr Gln Leu Gly
705                 710                 715                 720

Ile Glu Lys Leu Leu Asp Pro Glu Asp Val Asp Thr Thr Tyr Pro Asp
```

-continued

```
                725                 730                 735
Lys Lys Ser Ile Leu Met Tyr Ile Thr Ser Leu Phe Gln Val Leu Pro
            740                 745                 750
Gln Gln Val Ser Ile Glu Ala Ile Gln Glu Val Glu Met Leu Pro Arg
            755                 760                 765
Pro Pro Lys Val Thr Lys Glu Glu His Phe Gln Leu His His Gln Met
        770                 775                 780
His Tyr Ser Gln Gln Ile Thr Val Ser Leu Ala Gln Gly Tyr Glu Arg
785                 790                 795                 800
Thr Ser Ser Pro Lys Pro Arg Phe Lys Ser Tyr Ala Tyr Thr Gln Ala
                805                 810                 815
Ala Tyr Val Thr Thr Ser Asp Pro Thr Arg Ser Pro Phe Pro Ser Gln
            820                 825                 830
His Leu Glu Ala Pro Glu Asp Lys Ser Phe Gly Ser Ser Leu Met Glu
            835                 840                 845
Ser Glu Val Asn Leu Asp Arg Tyr Gln Thr Ala Leu Glu Glu Val Leu
        850                 855                 860
Ser Trp Leu Leu Ser Ala Glu Asp Thr Leu Gln Ala Gln Gly Glu Ile
865                 870                 875                 880
Ser Asn Asp Val Glu Val Lys Asp Gln Phe His Thr His Glu Gly
                885                 890                 895
Tyr Met Met Asp Leu Thr Ala His Gln Gly Arg Val Gly Asn Ile Leu
            900                 905                 910
Gln Leu Gly Ser Lys Leu Ile Gly Thr Gly Lys Leu Ser Glu Asp Glu
            915                 920                 925
Glu Thr Glu Val Gln Glu Gln Met Asn Leu Leu Asn Ser Arg Trp Glu
        930                 935                 940
Cys Leu Arg Val Ala Ser Met Glu Lys Gln Ser Asn Leu His Arg Val
945                 950                 955                 960
Leu Met Asp Leu Gln Asn Gln Lys Leu Lys Glu Leu Asn Asp Trp Leu
                965                 970                 975
Thr Lys Thr Glu Glu Arg Thr Arg Lys Met Glu Glu Glu Pro Leu Gly
            980                 985                 990
Pro Asp Leu Glu Asp Leu Lys Arg Gln Val Gln Gln His Lys Val Leu
            995                1000                1005
Gln Glu Asp Leu Glu Gln Glu Gln Val Arg Val Asn Ser Leu Thr
        1010                1015                1020
His Met Val Val Val Asp Glu Ser Ser Gly Asp His Ala Thr
        1025                1030                1035
Ala Ala Leu Glu Glu Gln Leu Lys Val Leu Gly Asp Arg Trp Ala
        1040                1045                1050
Asn Ile Cys Arg Trp Thr Glu Asp Arg Trp Val Leu Leu Gln Asp
        1055                1060                1065
Ile Leu Leu Lys Trp Gln Arg Leu Thr Glu Glu Gln Cys Leu Phe
        1070                1075                1080
Ser Ala Trp Leu Ser Glu Lys Glu Asp Ala Val Asn Lys Ile His
        1085                1090                1095
Thr Thr Gly Phe Lys Asp Gln Asn Glu Met Leu Ser Ser Leu Gln
        1100                1105                1110
Lys Leu Ala Val Leu Lys Ala Asp Leu Glu Lys Lys Gln Ser
        1115                1120                1125
Met Gly Lys Leu Tyr Ser Leu Lys Gln Asp Leu Leu Ser Thr Leu
        1130                1135                1140
```

```
Lys Asn Lys Ser Val Thr Gln Lys Thr Glu Ala Trp Leu Asp Asn
    1145            1150                1155

Phe Ala Arg Cys Trp Asp Asn Leu Val Gln Lys Leu Glu Lys Ser
    1160            1165                1170

Thr Ala Gln Glu Thr Glu Ile Ala Val Gln Ala Lys Gln Pro Asp
    1175            1180                1185

Val Glu Glu Ile Leu Ser Lys Gly Gln His Leu Tyr Lys Glu Lys
    1190            1195                1200

Pro Ala Thr Gln Pro Val Lys Arg Lys Leu Glu Asp Leu Ser Ser
    1205            1210                1215

Glu Trp Lys Ala Val Asn Arg Leu Leu Gln Glu Leu Arg Ala Lys
    1220            1225                1230

Gln Pro Asp Leu Ala Pro Gly Leu Thr Thr Ile Gly Ala Ser Pro
    1235            1240                1245

Thr Gln Thr Val Thr Leu Val Thr Gln Pro Val Val Thr Lys Glu
    1250            1255                1260

Thr Ala Ile Ser Lys Leu Glu Met Pro Ser Ser Leu Met Leu Glu
    1265            1270                1275

Val Pro Ala Leu Ala Asp Phe Asn Arg Ala Trp Thr Glu Leu Thr
    1280            1285                1290

Asp Trp Leu Ser Leu Leu Asp Gln Val Ile Lys Ser Gln Arg Val
    1295            1300                1305

Met Val Gly Asp Leu Glu Asp Ile Asn Glu Met Ile Ile Lys Gln
    1310            1315                1320

Lys Ala Thr Met Gln Asp Leu Glu Gln Arg Arg Pro Gln Leu Glu
    1325            1330                1335

Glu Leu Ile Thr Ala Ala Gln Asn Leu Lys Asn Lys Thr Ser Asn
    1340            1345                1350

Gln Glu Ala Arg Thr Ile Ile Thr Asp Arg Ile Glu Arg Ile Gln
    1355            1360                1365

Asn Gln Trp Asp Glu Val Gln Glu His Leu Gln Asn Arg Arg Gln
    1370            1375                1380

Gln Leu Asn Glu Met Leu Lys Asp Ser Thr Gln Trp Leu Glu Ala
    1385            1390                1395

Lys Glu Glu Ala Glu Gln Val Leu Gly Gln Ala Arg Ala Lys Leu
    1400            1405                1410

Glu Ser Trp Lys Glu Gly Pro Tyr Thr Val Asp Ala Ile Gln Lys
    1415            1420                1425

Lys Ile Thr Glu Thr Lys Gln Leu Ala Lys Asp Leu Arg Gln Trp
    1430            1435                1440

Gln Thr Asn Val Asp Val Ala Asn Asp Leu Ala Leu Lys Leu Leu
    1445            1450                1455

Arg Asp Tyr Ser Ala Asp Asp Thr Arg Lys Val His Met Ile Thr
    1460            1465                1470

Glu Asn Ile Asn Ala Ser Trp Arg Ser Ile His Lys Arg Val Ser
    1475            1480                1485

Glu Arg Glu Ala Ala Leu Glu Glu Thr His Arg Leu Leu Gln Gln
    1490            1495                1500

Phe Pro Leu Asp Leu Glu Lys Phe Leu Ala Trp Leu Thr Glu Ala
    1505            1510                1515

Glu Thr Thr Ala Asn Val Leu Gln Asp Ala Thr Arg Lys Glu Arg
    1520            1525                1530
```

| | | | | | | | | | | |
|---|---|---|---|---|---|---|---|---|---|---|
| Leu | Leu | Glu | Asp | Ser | Lys | Gly | Val | Lys | Glu | Leu | Met | Lys | Gln | Trp |
| | 1535 | | | | 1540 | | | | | 1545 | | | | |
| Gln | Asp | Leu | Gln | Gly | Glu | Ile | Glu | Ala | His | Thr | Asp | Val | Tyr | His |
| 1550 | | | | | 1555 | | | | | 1560 | | | | |
| Asn | Leu | Asp | Glu | Asn | Ser | Gln | Lys | Ile | Leu | Arg | Ser | Leu | Glu | Gly |
| 1565 | | | | | 1570 | | | | | 1575 | | | | |
| Ser | Asp | Asp | Ala | Val | Leu | Leu | Gln | Arg | Arg | Leu | Asp | Asn | Met | Asn |
| 1580 | | | | | 1585 | | | | | 1590 | | | | |
| Phe | Lys | Trp | Ser | Glu | Leu | Arg | Lys | Lys | Ser | Leu | Asn | Ile | Arg | Ser |
| 1595 | | | | | 1600 | | | | | 1605 | | | | |
| His | Leu | Glu | Ala | Ser | Ser | Asp | Gln | Trp | Lys | Arg | Leu | His | Leu | Ser |
| 1610 | | | | | 1615 | | | | | 1620 | | | | |
| Leu | Gln | Glu | Leu | Leu | Val | Trp | Leu | Gln | Leu | Lys | Asp | Asp | Glu | Leu |
| 1625 | | | | | 1630 | | | | | 1635 | | | | |
| Ser | Arg | Gln | Ala | Pro | Ile | Gly | Gly | Asp | Phe | Pro | Ala | Val | Gln | Lys |
| 1640 | | | | | 1645 | | | | | 1650 | | | | |
| Gln | Asn | Asp | Val | His | Arg | Ala | Phe | Lys | Arg | Glu | Leu | Lys | Thr | Lys |
| 1655 | | | | | 1660 | | | | | 1665 | | | | |
| Glu | Pro | Val | Ile | Met | Ser | Thr | Leu | Glu | Thr | Val | Arg | Ile | Phe | Leu |
| 1670 | | | | | 1675 | | | | | 1680 | | | | |
| Thr | Glu | Gln | Pro | Leu | Glu | Gly | Leu | Glu | Lys | Leu | Tyr | Gln | Glu | Pro |
| 1685 | | | | | 1690 | | | | | 1695 | | | | |
| Arg | Glu | Leu | Pro | Pro | Glu | Glu | Arg | Ala | Gln | Asn | Val | Thr | Arg | Leu |
| 1700 | | | | | 1705 | | | | | 1710 | | | | |
| Leu | Arg | Lys | Gln | Ala | Glu | Glu | Val | Asn | Thr | Glu | Trp | Glu | Lys | Leu |
| 1715 | | | | | 1720 | | | | | 1725 | | | | |
| Asn | Leu | His | Ser | Ala | Asp | Trp | Gln | Arg | Lys | Ile | Asp | Glu | Thr | Leu |
| 1730 | | | | | 1735 | | | | | 1740 | | | | |
| Glu | Arg | Leu | Gln | Glu | Leu | Gln | Glu | Ala | Thr | Asp | Glu | Leu | Asp | Leu |
| 1745 | | | | | 1750 | | | | | 1755 | | | | |
| Lys | Leu | Arg | Gln | Ala | Glu | Val | Ile | Lys | Gly | Ser | Trp | Gln | Pro | Val |
| 1760 | | | | | 1765 | | | | | 1770 | | | | |
| Gly | Asp | Leu | Leu | Ile | Asp | Ser | Leu | Gln | Asp | His | Leu | Glu | Lys | Val |
| 1775 | | | | | 1780 | | | | | 1785 | | | | |
| Lys | Ala | Leu | Arg | Gly | Glu | Ile | Ala | Pro | Leu | Lys | Glu | Asn | Val | Ser |
| 1790 | | | | | 1795 | | | | | 1800 | | | | |
| His | Val | Asn | Asp | Leu | Ala | Arg | Gln | Leu | Thr | Thr | Leu | Gly | Ile | Gln |
| 1805 | | | | | 1810 | | | | | 1815 | | | | |
| Leu | Ser | Pro | Tyr | Asn | Leu | Ser | Thr | Leu | Glu | Asp | Leu | Asn | Thr | Arg |
| 1820 | | | | | 1825 | | | | | 1830 | | | | |
| Trp | Lys | Leu | Leu | Gln | Val | Ala | Val | Glu | Asp | Arg | Val | Arg | Gln | Leu |
| 1835 | | | | | 1840 | | | | | 1845 | | | | |
| His | Glu | Ala | His | Arg | Asp | Phe | Gly | Pro | Ala | Ser | Gln | His | Phe | Leu |
| 1850 | | | | | 1855 | | | | | 1860 | | | | |
| Ser | Thr | Ser | Val | Gln | Gly | Pro | Trp | Glu | Arg | Ala | Ile | Ser | Pro | Asn |
| 1865 | | | | | 1870 | | | | | 1875 | | | | |
| Lys | Val | Pro | Tyr | Tyr | Ile | Asn | His | Glu | Thr | Gln | Thr | Thr | Cys | Trp |
| 1880 | | | | | 1885 | | | | | 1890 | | | | |
| Asp | His | Pro | Lys | Met | Thr | Glu | Leu | Tyr | Gln | Ser | Leu | Ala | Asp | Leu |
| 1895 | | | | | 1900 | | | | | 1905 | | | | |
| Asn | Asn | Val | Arg | Phe | Ser | Ala | Tyr | Arg | Thr | Ala | Met | Lys | Leu | Arg |
| 1910 | | | | | 1915 | | | | | 1920 | | | | |
| Arg | Leu | Gln | Lys | Ala | Leu | Cys | Leu | Asp | Leu | Leu | Ser | Leu | Ser | Ala |

-continued

```
           1925                1930                1935
Ala Cys Asp Ala Leu Asp Gln His Asn Leu Lys Gln Asn Asp Gln
       1940                1945                1950
Pro Met Asp Ile Leu Gln Ile Ile Asn Cys Leu Thr Thr Ile Tyr
       1955                1960                1965
Asp Arg Leu Glu Gln Glu His Asn Asn Leu Val Asn Val Pro Leu
       1970                1975                1980
Cys Val Asp Met Cys Leu Asn Trp Leu Leu Asn Val Tyr Asp Thr
       1985                1990                1995
Gly Arg Thr Gly Arg Ile Arg Val Leu Ser Phe Lys Thr Gly Ile
       2000                2005                2010
Ile Ser Leu Cys Lys Ala His Leu Glu Asp Lys Tyr Arg Tyr Leu
       2015                2020                2025
Phe Lys Gln Val Ala Ser Ser Thr Gly Phe Cys Asp Gln Arg Arg
       2030                2035                2040
Leu Gly Leu Leu Leu His Asp Ser Ile Gln Ile Pro Arg Gln Leu
       2045                2050                2055
Gly Glu Val Ala Ser Phe Gly Gly Ser Asn Ile Glu Pro Ser Val
       2060                2065                2070
Arg Ser Cys Phe Gln Phe Ala Asn Asn Lys Pro Glu Ile Glu Ala
       2075                2080                2085
Ala Leu Phe Leu Asp Trp Met Arg Leu Glu Pro Gln Ser Met Val
       2090                2095                2100
Trp Leu Pro Val Leu His Arg Val Ala Ala Glu Thr Ala Lys
       2105                2110                2115
His Gln Ala Lys Cys Asn Ile Cys Lys Glu Cys Pro Ile Ile Gly
       2120                2125                2130
Phe Arg Tyr Arg Ser Leu Lys His Phe Asn Tyr Asp Ile Cys Gln
       2135                2140                2145
Ser Cys Phe Phe Ser Gly Arg Val Ala Lys Gly His Lys Met His
       2150                2155                2160
Tyr Pro Met Val Glu Tyr Cys Thr Pro Thr Thr Ser Gly Glu Asp
       2165                2170                2175
Val Arg Asp Phe Ala Lys Val Leu Lys Asn Lys Phe Arg Thr Lys
       2180                2185                2190
Arg Tyr Phe Ala Lys His Pro Arg Met Gly Tyr Leu Pro Val Gln
       2195                2200                2205
Thr Val Leu Glu Gly Asp Asn Met Glu Thr Pro Val Thr Leu Ile
       2210                2215                2220
Asn Phe Trp Pro Val Asp Ser Ala Pro Ala Ser Ser Pro Gln Leu
       2225                2230                2235
Ser His Asp Asp Thr His Ser Arg Ile Glu His Tyr Ala Ser Arg
       2240                2245                2250
Leu Ala Glu Met Glu Asn Ser Asn Gly Ser Tyr Leu Asn Asp Ser
       2255                2260                2265
Ile Ser Pro Asn Glu Ser Ile Asp Asp Glu His Leu Leu Ile Gln
       2270                2275                2280
His Tyr Cys Gln Ser Leu Asn Gln Asp Ser Pro Leu Ser Gln Pro
       2285                2290                2295
Arg Ser Pro Ala Gln Ile Leu Ile Ser Leu Glu Ser Glu Glu Arg
       2300                2305                2310
Gly Glu Leu Glu Arg Ile Leu Ala Asp Leu Glu Glu Glu Asn Arg
       2315                2320                2325
```

| Asn | Leu | Gln | Ala | Glu | Tyr | Asp | Arg | Leu | Lys | Gln | Gln | His | Glu | His |
|  | 2330 |  |  |  | 2335 |  |  |  | 2340 |  |  |  |  |  |

| Lys | Gly | Leu | Ser | Pro | Leu | Pro | Ser | Pro | Pro | Glu | Met | Met | Pro | Thr |
|  | 2345 |  |  |  | 2350 |  |  |  | 2355 |  |  |  |  |  |

| Ser | Pro | Gln | Ser | Pro | Arg | Asp | Ala | Glu | Leu | Ile | Ala | Glu | Ala | Lys |
|  | 2360 |  |  |  | 2365 |  |  |  | 2370 |  |  |  |  |  |

| Leu | Leu | Arg | Gln | His | Lys | Gly | Arg | Leu | Glu | Ala | Arg | Met | Gln | Ile |
|  | 2375 |  |  |  | 2380 |  |  |  | 2385 |  |  |  |  |  |

| Leu | Glu | Asp | His | Asn | Lys | Gln | Leu | Glu | Ser | Gln | Leu | His | Arg | Leu |
|  | 2390 |  |  |  | 2395 |  |  |  | 2400 |  |  |  |  |  |

| Arg | Gln | Leu | Leu | Glu | Gln | Pro | Gln | Ala | Glu | Ala | Lys | Val | Asn | Gly |
|  | 2405 |  |  |  | 2410 |  |  |  | 2415 |  |  |  |  |  |

| Thr | Thr | Val | Ser | Ser | Pro | Ser | Thr | Ser | Leu | Gln | Arg | Ser | Asp | Ser |
|  | 2420 |  |  |  | 2425 |  |  |  | 2430 |  |  |  |  |  |

| Ser | Gln | Pro | Met | Leu | Leu | Arg | Val | Val | Gly | Ser | Gln | Thr | Ser | Asp |
|  | 2435 |  |  |  | 2440 |  |  |  | 2445 |  |  |  |  |  |

| Ser | Met | Gly | Glu | Glu | Asp | Leu | Leu | Ser | Pro | Pro | Gln | Asp | Thr | Ser |
|  | 2450 |  |  |  | 2455 |  |  |  | 2460 |  |  |  |  |  |

| Thr | Gly | Leu | Glu | Glu | Val | Met | Glu | Gln | Leu | Asn | Asn | Ser | Phe | Pro |
|  | 2465 |  |  |  | 2470 |  |  |  | 2475 |  |  |  |  |  |

| Ser | Ser | Arg | Gly | Arg | Asn | Thr | Pro | Gly | Lys | Pro | Met | Arg | Glu | Asp |
|  | 2480 |  |  |  | 2485 |  |  |  | 2490 |  |  |  |  |  |

| Thr | Met |
|  | 2495 |

<210> SEQ ID NO 5
<211> LENGTH: 12588
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic nucleotide sequence of proposed Dystrophin-VSV-G
    chimeric protein with VSV-G at C-terminal"

<400> SEQUENCE: 5

```
atgctttggt gggaagaagt agaggactgt tatgaaagag aagatgttca aagaaaaca      60 ttcacaaaat gggtaaatgc acaattttct aagtttggga agcagcatat tgagaacctc    120
ttcagtgacc tacaggatgg gaggcgcctc ctagacctcc tcgaaggcct gacagggcaa    180
aaactgccaa agaaaaaagg atccacaaga gttcatgccc tgaacaatgt caacaaggca    240
ctgcgggttt tgcagaacaa taatgttgat ttagtgaata ttggaagtac tgacatcgta    300
gatggaaatc ataaactgac tcttggtttg atttggaata atcctcca ctggcaggtc      360 aaaaatgtaa tgaaaatat catggctgga ttgcaacaaa ccaacagtga aaagattctc    420
ctgagctggg tccgacaatc aactcgtaat tatccacagg ttaatgtaat caacttcacc    480
accagctggt ctgatggcct ggctttgaat gctctcatcc atagtcatag gccagaccta    540
tttgactgga atagtgtggt ttgccagcag tcagccacac aacgactgga acatgcattc    600
aacatcgcca gatatcaatt aggcatagag aaactactcg atcctgaaga tgttgatacc    660
acctatccag ataagaagtc catcttaatg tacatcacat cactcttcca agttttgcct    720
caacaagtga gcattgaagc catccaggaa gtggaaatgt tgccaaggcc acctaaagtg    780
actaaagaag aacatttca gttacatcat caaatgcact attctcaaca gatcacggtc    840
agtctagcac agggatatga gaaacttct tcccctaagc ctcgattcaa gagctatgcc    900
```

```
tacacacagg ctgcttatgt caccacctct gaccctacac ggagcccatt tccttcacag    960
catttggaag ctcctgaaga caagtcattt ggcagttcat tgatggagag tgaagtaaac   1020
ctggaccgtt atcaaacagc tttagaagaa gtattatcgt ggcttctttc tgctgaggac   1080
acattgcaag cacaaggaga gatttctaat gatgtggaag tggtgaaaga ccagtttcat   1140
actcatgagg ggtacatgat ggatttgaca gcccatcagg gccgggttgg taatattcta   1200
caattgggaa gtaagctgat tggaacagga aaattatcag aagatgaaga aactgaagta   1260
caagagcaga tgaatctcct aaattcaaga tgggaatgcc tcagggtagc tagcatggaa   1320
aaacaaagca atttacatag agtttttaatg gatctccaga atcagaaact gaaagagttg   1380
aatgactggc taacaaaaac agaagaaaga acaaggaaaa tggaggaaga gcctcttgga   1440
cctgatcttg aagacctaaa acgccaagta caacaacata aggtgcttca agaagatcta   1500
gaacaagaac aagtcagggt caattctctc actcacatgg tggtggtagt tgatgaatct   1560
agtggagatc acgcaactgc tgctttggaa gaacaactta aggtattggg agatcgatgg   1620
gcaaacatct gtagatggac agaagaccgc tgggttcttt tacaagacat ccttctcaaa   1680
tggcaacgtc ttactgaaga acagtgcctt tttagtgcat ggctttcaga aaagaagat   1740
gcagtgaaca agattcacac aactggcttt aaagatcaaa atgaaatgtt atcaagtctt   1800
caaaaactgg ccgttttaaa agcggatcta gaaaagaaaa agcaatccat gggcaaactg   1860
tattcactca acaagatctc tctttcaaca ctgaagaata agtcagtgac ccagaagacg   1920
gaagcatggc tggataactt tgcccggtgt tgggataatt tagtccaaaa acttgaaaag   1980
agtacagcac agatttcaca ggctgtcacc accactcagc catcactaac acagacaact   2040
gtaatggaaa cagtaactac ggtgaccaca agggaacaga tcctggtaaa gcatgctcaa   2100
gaggaacttc caccaccacc tccccaaaag aagaggcaga ttactgtgga ttctgaaatt   2160
aggaaaaggt tggatgttga tataactgaa cttcacagct ggattactcg ctcagaagct   2220
gtgttgcaga gtcctgaatt tgcaatcttt cggaaggaag gcaacttctc agacttaaaa   2280
gaaaaagtca atgccataga gcgagaaaaa gctgagaagt tcagaaaact gcaagatgcc   2340
agcagatcag ctcaggccct ggtggaacag atggtgaatg agggtgttaa tgcagatagc   2400
atcaaacaag cctcagaaca actgaacagc cggtggatcg aattctgcca gttgctaagt   2460
gagagactta actggctgga gtatcagaac aacatcatcg ctttctataa tcagctacaa   2520
caattggagc agatgacaac tactgctgaa aactggttga aaatccaacc caccacccca   2580
tcagagccaa cagcaattaa aagtcagtta aaaatttgta aggatgaagt caaccggcta   2640
tcaggtcttc aacctcaaat tgaacgatta aaaattcaaa gcatagccct gaaagagaaa   2700
ggacaaggac ccatgttcct ggatgcagac tttgtggcct ttacaaatca ttttaagcaa   2760
gtcttttctg atgtgcaggc cagagagaaa gagctacaga caattttga cactttgcca   2820
ccaatgcgct atcaggagac catgagtgcc atcaggacat gggtccagca gtcagaaacc   2880
aaactctcca tacctcaact tagtgtcacc gactatgaaa tcatggagca gagactcggg   2940
gaattgcagg ctttacaaag ttctctgcaa gagcaacaaa gtggcctata ctatctcagc   3000
accactgtga aagagatgtc gaagaaagcg ccctctgaaa ttagccggaa atatcaatca   3060
gaatttgaag aaattgaggg acgctggaag aagctctcct cccagctggt tgagcattgt   3120
caaaagctag aggagcaaat gaataaactc cgaaaaattc agaatcacat acaaaccctg   3180
aagaaatgga tggctgaagt tgatgttttt ctgaaggagg aatggcctgc ccttgggat   3240
```

```
tcagaaattc taaaaaagca gctgaaacag tgcagacttt tagtcagtga tattcagaca    3300
attcagccca gtctaaacag tgtcaatgaa ggtgggcaga agataaagaa tgaagcagag    3360
ccagagtttg cttcgagact tgagacagaa ctcaaagaac ttaacactca gtgggatcac    3420
atgtgccaac aggtctatgc cagaaaggag gccttgaagg gaggtttgga gaaaactgta    3480
agcctccaga aagatctatc agagatgcac gaatggatga cacaagctga agaagagtat    3540
cttgagagag attttgaata taaaactcca gatgaattac agaaagcagt tgaagagatg    3600
aagagagcta agaagaggc ccaacaaaaa gaagcgaaag tgaaactcct tactgagtct    3660
gtaaatagtg tcatagctca agctccacct gtagcacaag aggccttaaa aaaggaactt    3720
gaaactctaa ccaccaacta ccagtggctc tgcactaggc tgaatgggaa atgcaagact    3780
ttggaagaag tttgggcatg ttggcatgag ttattgtcat acttggagaa agcaaacaag    3840
tggctaaatg aagtagaatt taaacttaaa accactgaaa acattcctgg cggagctgag    3900
gaaatctctg aggtgctaga ttcacttgaa aatttgatgc acattcaga ggataaccca     3960
aatcagattc gcatattggc acagacccta acagatggcg gagtcatgga tgagctaatc    4020
aatgaggaac ttgagacatt taattctcgt tggagggaac tacatgaaga ggctgtaagg    4080
aggcaaaagt tgcttgaaca gagcatccag tctgcccagg agactgaaaa atccttacac    4140
ttaatccagg agtccctcac attcattgac aagcagttgg cagcttatat tgcagacaag    4200
gtggacgcag ctcaaatgcc tcaggaagcc cagaaaatcc aatctgattt gacaagtcat    4260
gagatcagtt tagaagaaat gaagaaacat aatcagggga aggaggctgc ccaaagagtc    4320
ctgtctcaga ttgatgttgc acagaaaaaa ttacaagatg tctccatgaa gtttcgatta    4380
ttccagaaac cagccaattt tgagctgcgt ctacaagaaa gtaagatgat tttagatgaa    4440
gtgaagatgc acttgcctgc attggaaaca aagagtgtgg aacaggaagt agtacagtca    4500
cagctaaatc attgtgtgaa cttgtataaa agtctgagtg aagtgaagtc tgaagtggaa    4560
atggtgataa agactggacg tcagattgta cagaaaaagc agacggaaaa tcccaaagaa    4620
cttgatgaaa gagtaacagc tttgaaattg cattataatg agctgggagc aaaggtaaca    4680
gaaagaaagc aacagttgga gaaatgcttg aaattgtccc gtaagatgcg aaaggaaatg    4740
aatgtcttga cagaatggct ggcagctaca gatatggaat tgacaaagag atcagcagtt    4800
gaaggaatgc ctagtaattt ggattctgaa gttgcctggg gaaaggctac tcaaaaagag    4860
attgagaaac agaaggtgca cctgaagagt atcacagagg taggagaggc cttgaaaaca    4920
gttttgggca agaaggagac gttggtgaa gataaactca gtcttctgaa tagtaactgg    4980
atagctgtca cctcccgagc agaagagtgg ttaaatcttt tgttggaata ccagaaacac    5040
atggaaactt tgaccagaa tgtggaccac atcacaaagt ggatcattca ggctgacaca    5100
cttttggatg aatcagagaa aaagaaaccc cagcaaaaag aagacgtgct taagcgttta    5160
aaggcagaac tgaatgacat acgcccaaag gtggactcta cacgtgacca agcagcaaac    5220
ttgatggcaa accgcggtga ccactgcagg aaattagtag agccccaaat ctcagagctc    5280
aaccatcgat ttgcagccat ttcacacaga attaagactg aaaaggcctc cattcctttg    5340
aaggaattgg agcagtttaa ctcagatata caaaaattgc ttgaaccact ggaggctgaa    5400
attcagcagg gggtgaatct gaaagaggaa gacttcaata agatatgaa tgaagacaat    5460
gagggtactg taaagaatt gttgcaaaga ggagacaact acaacaaag aatcacagat    5520
gagagaaaga gagaggaaat aaagataaaa cagcagctgt tacagacaaa acataatgct    5580
ctcaaggatt tgaggtctca aagaagaaaa aaggctctag aaatttctca tcagtggtat    5640
```

```
cagtacaaga ggcaggctga tgatctcctg aaatgcttgg atgacattga aaaaaaatta    5700
gccagcctac ctgagcccag agatgaaagg aaaataaagg aaattgatcg ggaattgcag    5760
aagaagaaag aggagctgaa tgcagtgcgt aggcaagctg agggcttgtc tgaggatggg    5820
gccgcaatgg cagtggagcc aactcagatc cagctcagca agcgctggcg ggaaattgag    5880
agcaaatttg ctcagtttcg aagactcaac tttgcacaaa ttcacactgt ccgtgaagaa    5940
acgatgatga tgatgactga agacatgcct ttggaaattt cttatgtgcc ttctacttat    6000
ttgactgaaa tcactcatgt ctcacaagcc ctattagaag tggaacaact tctcaatgct    6060
cctgacctct gtgctaagga cttgaagat ctctttaagc aagaggagtc tctgaagaat    6120
ataaaagata gtctacaaca aagctcaggt cggattgaca ttattcatag caagaagaca    6180
gcagcattgc aaagtgcaac gcctgtggaa agggtgaagc tacaggaagc tctctcccag    6240
cttgatttcc aatgggaaaa agttaacaaa atgtacaagg accgacaagg gcgatttgac    6300
agatctgttg agaaatggcg gcgttttcat tatgatataa agatatttaa tcagtggcta    6360
acagaagctg aacagtttct cagaaagaca caaattcctg agaattggga acatgctaaa    6420
tacaaatggt atcttaagga actccaggat ggcattgggc agcggcaaac tgttgtcaga    6480
acattgaatg caactgggga agaaataatt cagcaatcct caaaaacaga tgccagtatt    6540
ctacaggaaa aattgggaag cctgaatctg cggtggcagg aggtctgcaa acagctgtca    6600
gacagaaaaa agaggctaga agaacaaaag aatatcttgt cagaatttca aagagattta    6660
aatgaatttg ttttatggtt ggaggaagca gataacattg ctagtatccc acttgaacct    6720
ggaaaagagc agcaactaaa agaaaagctt gagcaagtca agttactggt ggaagagttg    6780
cccctgcgcc agggaattct caaacaatta atgaaactg gaggacccgt gcttgtaagt    6840
gctcccataa gcccagaaga gcaagataaa cttgaaaata agctcaagca gacaaatctc    6900
cagtggataa aggtttccag agctttacct gagaaacaag gagaaattga agctcaaata    6960
aaagaccttg ggcagcttga aaaaaagctt gaagaccttg aagagcagtt aaatcatctg    7020
ctgctgtggt tatctcctat taggaatcag ttggaaattt ataaccaacc aaaccaagaa    7080
ggaccatttg acgttcagga aactgaaata gcagttcaag ctaaacaacc ggatgtggaa    7140
gagattttgt ctaaagggca gcatttgtac aaggaaaaac cagccactca gccagtgaag    7200
aggaagttag aagatctgag ctctgagtgg aaggcggtaa accgtttact tcaagagctg    7260
agggcaaagc agcctgacct agctcctgga ctgaccacta ttggagcctc tcctactcag    7320
actgttactc tggtgacaca acctgtggtt actaaggaaa ctgccatctc caaactagaa    7380
atgccatctt ccttgatgtt ggaggtacct gctctggcag atttcaaccg gcttggaca    7440 gaacttaccg actggctttc tctgcttgat caagttataa aatcacagag ggtgatggtg    7500
ggtgaccttg aggatatcaa cgagatgatc atcaagcaga aggcaacaat gcaggatttg    7560
gaacagaggc gtccccagtt ggaagaactc attaccgctg cccaaaattt gaaaaacaag    7620
accagcaatc aagaggctag aacaatcatt acggatcgaa ttgaaagaat tcagaatcag    7680
tgggatgaag tacaagaaca ccttcagaac cggaggcaac agttgaatga atgttaaag    7740 gattcaacac aatggctgga agctaaggaa gaagctgagc aggtcttagg acaggccaga    7800
gccaagcttg agtcatggaa ggagggtccc tatacagtag atgcaatcca aagaaaatc    7860 acagaaacca agcagttggc caaagacctc cgccagtggc agacaaatgt agatgtggca    7920
aatgacttgg ccctgaaact tctccgggat tattctgcag atgataccag aaaagtccac    7980
```

```
atgataacag agaatatcaa tgcctcttgg agaagcattc ataaaagggt gagtgagcga    8040
gaggctgctt tggaagaaac tcatagatta ctgcaacagt tccccctgga cctggaaaag    8100
tttcttgcct ggcttacaga agctgaaaca actgccaatg tcctacagga tgctacccgt    8160
aaggaaaggc tcctagaaga ctccaaggga gtaaaagagc tgatgaaaca atggcaagac    8220
ctccaaggtg aaattgaagc tcacacagat gtttatcaca acctggatga aaacagccaa    8280
aaaatcctga gatccctgga aggttccgat gatgcagtcc tgttacaaag cgtttggat     8340 aacatgaact tcaagtggag tgaacttcgg aaaaagtctc tcaacattag gtcccatttg    8400
gaagccagtt ctgaccagtg gaagcgtctg caccttttctc tgcaggaact tctggtgtgg   8460
ctacagctga aagatgatga attaagccgg caggcaccta ttggaggcga ctttccagca    8520
gttcagaagc agaacgatgt acatagggcc ttcaagaggg aattgaaaac taaagaacct    8580
gtaatcatga gtactcttga gactgtacga atatttctga cagagcagcc tttggaagga    8640
ctagagaaac tctaccagga gcccagagag ctgcctcctg aggagagagc ccagaatgtc    8700
actcggcttc tacgaaagca ggctgaggag gtcaatactg agtgggaaaa attgaacctg    8760
cactccgctg actggcagag aaaaatagat gagacccttg aaagactcca ggaacttcaa    8820
gaggccacgg atgagctgga cctcaagctg cgccaagctg aggtgatcaa gggatcctgg    8880
cagcccgtgg gcgatctcct cattgactct ctccaagatc acctcgagaa agtcaaggca    8940
cttcgaggag aaattgcgcc tctgaaagag aacgtgagcc acgtcaatga ccttgctcgc    9000
cagcttacca ctttgggcat tcagctctca ccgtataacc tcagcactct ggaagacctg    9060
aacaccagat ggaagcttct gcaggtggcc gtcgaggacc gagtcaggca gctgcatgaa    9120
gcccacaggg actttggtcc agcatctcag cactttcttt ccacgtctgt ccagggtccc    9180
tgggagagag ccatctcgcc aaacaaagtg ccctactata tcaaccacga gactcaaaca    9240
acttgctggg accatcccaa aatgacagag ctctaccagt ctttagctga cctgaataat    9300
gtcagattct cagcttatag gactgccatg aaactccgaa gactgcagaa ggcccttttgc   9360 ttggatctct tgagcctgtc agctgcatgt gatgccttgg accagcacaa cctcaagcaa    9420
aatgaccagc ccatggatat cctgcagatt attaattgtt tgaccactat ttatgaccgc    9480
ctggagcaag agcacaacaa tttggtcaac gtccctctct gcgtggatat gtgtctgaac    9540
tggctgctga atgtttatga tacgggacga acagggagga tccgtgtcct gtcttttaaa    9600
actggcatca tttccctgtg taaagcacat ttggaagaca agtacagata ccttttcaag    9660
caagtggcaa gttcaacagg attttgtgac cagcgcaggc tgggcctcct tctgcatgat    9720
tctatccaaa ttccaagaca gttgggtgaa gttgcatcct ttgggggcag taacattgag    9780
ccaagtgtcc ggagctgctt ccaatttgct aataataagc cagagatcga agcggccctc    9840
ttcctagact ggatgagact ggaaccccag tccatggtgt ggctgcccgt cctgcacaga    9900
gtggctgctg cagaaactgc caagcatcag gccaaatgta acatctgcaa agagtgtcca    9960
atcattggat tcaggtacag gagtctaaag cactttaatt atgacatctg ccaaagctgc    10020 ttttttctg gtcgagttgc aaaaggccat aaaatgcact atcccatggt ggaatattgc    10080
actccgacta catcaggaga agatgttcga gactttgcca aggtactaaa aaacaaattt    10140
cgaaccaaaa ggtattttgc gaagcatccc cgaatgggct acctgccagt gcagactgtc    10200 ttagagggggg acaacatgga aactcccgtt actctgatca acttctggcc agtagattct    10260
gcgcctgcct cgtcccctca gctttcacac gatgatactg attcacgcat tgaacattat    10320
gctagcaggc tagcagaaat ggaaaacagc aatggatctt atctaaatga tagcatctct    10380
```

```
cctaatgaga gcatagatga tgaacatttg ttaatccagc attactgcca aagtttgaac  10440
caggactccc ccctgagcca gcctcgtagt cctgcccaga tcttgatttc cttagagagt  10500
gaggaaagag gggagctaga gagaatccta gcagatcttg aggaagaaaa caggaatctg  10560
caagcagaat atgaccgtct aaagcagcag cacgaacata aaggcctgtc cccactgccg  10620
tcccctcctg aaatgatgcc cacctctccc cagagtcccc gggatgctga gctcattgct  10680
gaggccaagc tactgcgtca acacaaaggc cgcctggaag ccaggatgca aatcctggaa  10740
gaccacaata aacagctgga gtcacagtta cacaggctaa ggcagctgct ggagcaaccc  10800
caggcagagg ccaaagtgaa tggcacaacg gtgtcctctc cttctacctc tctacagagg  10860
tccgacagca gtcagcctat gctgctccga gtggttggca gtcaaacttc ggactccatg  10920
ggtgaggaag atcttctcag tcctccccag gacacaagca cagggttaga ggaggtgatg  10980
gagcaactca acaactcctt ccctagttca agaggaagaa ataccCctgg aaagccactg  11040
ggactgtggg cactgaagtg ccttttgtac ttagcttttt tattcatcgg ggtgaattgc  11100
aagttcacca tagttttttcc acacaaccaa aaggaaact ggaaaaatgt tccttccaat  11160
taccattatt gcccgtcaag ctcagattta aattggcata atgacttaat aggcacagcc  11220
ttacaagtca aaatgcccaa gagtcacaag gctattcaag cagacggttg gatgtgtcat  11280
gcttccaaat gggtcactac ttgtgatttc cgctggtacg gaccgaagta tataacacat  11340
tccatccgat ccttcactcc atctgtagaa caatgcaagg aaagcattga acaaacgaaa  11400
caaggaactt ggctgaatcc aggcttccct cctcaaagtt gtggatatgc aactgtgacg  11460
gatgctgaag cagcgattgt ccaggtgact cctcaccatg tgcttgttga tgaatacaca  11520
ggagaatggg ttgattcaca gttcatcaac ggaaaatgca gcaatgacat atgccccact  11580
gtccataact ccacaacctg gcattccgac tataaggtca aagggctatg tgattctaac  11640
ctcatttcca cggacatcac cttcttctca gaggacggag agctatcatc cctaggaaag  11700
gagggcacag ggttcagaag taactacttt gcttatgaaa ctggagacaa ggcctgcaaa  11760
atgcagtact gcaagcattg gggagtcaga ctcccatcag gtgtctggtt cgagatggct  11820
gataaggatc tctttgctgc agccagattc cctgaatgcc cagaagggtc aagtatctct  11880
gctccatctc agacctcagt ggatgtaagt ctcattcagg acgttgagag gatcttggat  11940
tattccctct gccaagaaac ctggagcaaa atcagagcgg tcttcccat ctctccagtg  12000 gatctcagct atcttgctcc taaaaaccca ggaaccggtc ctgtctttac cataatcaat  12060 ggtacccctaa aatactttga gaccagatac atcgagtcg atattgctgc tccaatcctc  12120
tcaagaatgg tcggaatgat cagtggaact accacagaaa gggaactgtg ggatgactgg  12180
gctccatatg aagacgtgga aattggaccc aatggagttc tgaggaccag tttaggatat  12240
aagtttcctt tatatatgat tggacatggt atgttggact ccgatcttca tcttagctca  12300
aaggctcagg tgtttgaaca tcctcacatt caagacgctg cttcgcagct tcctgatgat  12360
gagactttat tttttggtga tactgggcta tccaaaaatc caatcgagtt tgtagaaggt  12420
tggttcagta gttggaagag ctctattgcc tcttttttct ttatcatagg gttaatcatt  12480
ggactattct tggttctccg agttggtatt tatctttgca ttaaattaaa gcacaccaag  12540
aaaagacaga tttatacaga catagagatg aaccgacttg gaaagtaa           12588

<210> SEQ ID NO 6
<211> LENGTH: 4194
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic amino acid sequence of proposed Dystrophin-VSV-G
      chimeric protein with VSV-G at C-terminal"

<400> SEQUENCE: 6

Met Leu Trp Trp Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly

```
                370             375             380
Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
                420                 425                 430

Cys Leu Arg Val Ala Ser Met Glu Lys Gln Ser Asn Leu His Arg Val
                435                 440                 445

Leu Met Asp Leu Gln Asn Gln Lys Leu Lys Glu Leu Asn Asp Trp Leu
            450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
                500                 505                 510

Met Val Val Val Asp Glu Ser Ser Gly Asp His Ala Thr Ala Ala
            515                 520                 525

Leu Glu Glu Gln Leu Lys Val Leu Gly Asp Arg Trp Ala Asn Ile Cys
            530                 535                 540

Arg Trp Thr Glu Asp Arg Trp Val Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575

Glu Lys Glu Asp Ala Val Asn Lys Ile His Thr Thr Gly Phe Lys Asp
                580                 585                 590

Gln Asn Glu Met Leu Ser Ser Leu Gln Lys Leu Ala Val Leu Lys Ala
                595                 600                 605

Asp Leu Glu Lys Lys Lys Gln Ser Met Gly Lys Leu Tyr Ser Leu Lys
            610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Ile Ser Gln Ala Val Thr Thr Thr
                660                 665                 670

Gln Pro Ser Leu Thr Gln Thr Thr Val Met Glu Thr Val Thr Thr Val
            675                 680                 685

Thr Thr Arg Glu Gln Ile Leu Val Lys His Ala Gln Glu Glu Leu Pro
690                 695                 700

Pro Pro Pro Gln Lys Lys Arg Gln Ile Thr Val Asp Ser Glu Ile
705                 710                 715                 720

Arg Lys Arg Leu Asp Val Asp Ile Thr Glu Leu His Ser Trp Ile Thr
                725                 730                 735

Arg Ser Glu Ala Val Leu Gln Ser Pro Glu Phe Ala Ile Phe Arg Lys
                740                 745                 750

Glu Gly Asn Phe Ser Asp Leu Lys Glu Lys Val Asn Ala Ile Glu Arg
                755                 760                 765

Glu Lys Ala Glu Lys Phe Arg Lys Leu Gln Asp Ala Ser Arg Ser Ala
            770                 775                 780

Gln Ala Leu Val Glu Gln Met Val Asn Glu Gly Val Asn Ala Asp Ser
785                 790                 795                 800
```

-continued

```
Ile Lys Gln Ala Ser Glu Gln Leu Asn Ser Arg Trp Ile Glu Phe Cys
            805                 810                 815
Gln Leu Leu Ser Glu Arg Leu Asn Trp Leu Glu Tyr Gln Asn Asn Ile
            820                 825                 830
Ile Ala Phe Tyr Asn Gln Leu Gln Gln Leu Glu Gln Met Thr Thr Thr
            835                 840                 845
Ala Glu Asn Trp Leu Lys Ile Gln Pro Thr Thr Pro Ser Glu Pro Thr
            850                 855                 860
Ala Ile Lys Ser Gln Leu Lys Ile Cys Lys Asp Glu Val Asn Arg Leu
865                 870                 875                 880
Ser Gly Leu Gln Pro Gln Ile Glu Arg Leu Lys Ile Gln Ser Ile Ala
            885                 890                 895
Leu Lys Glu Lys Gly Gln Gly Pro Met Phe Leu Asp Ala Asp Phe Val
            900                 905                 910
Ala Phe Thr Asn His Phe Lys Gln Val Phe Ser Asp Val Gln Ala Arg
            915                 920                 925
Glu Lys Glu Leu Gln Thr Ile Phe Asp Thr Leu Pro Pro Met Arg Tyr
            930                 935                 940
Gln Glu Thr Met Ser Ala Ile Arg Thr Trp Val Gln Gln Ser Glu Thr
945                 950                 955                 960
Lys Leu Ser Ile Pro Gln Leu Ser Val Thr Asp Tyr Glu Ile Met Glu
            965                 970                 975
Gln Arg Leu Gly Glu Leu Gln Ala Leu Gln Ser Ser Leu Gln Glu Gln
            980                 985                 990
Gln Ser Gly Leu Tyr Tyr Leu Ser Thr Thr Val Lys Glu Met Ser Lys
            995                 1000                1005
Lys Ala Pro Ser Glu Ile Ser Arg Lys Tyr Gln Ser Glu Phe Glu
            1010                1015                1020
Glu Ile Glu Gly Arg Trp Lys Lys Leu Ser Ser Gln Leu Val Glu
            1025                1030                1035
His Cys Gln Lys Leu Glu Glu Gln Met Asn Lys Leu Arg Lys Ile
            1040                1045                1050
Gln Asn His Ile Gln Thr Leu Lys Lys Trp Met Ala Glu Val Asp
            1055                1060                1065
Val Phe Leu Lys Glu Glu Trp Pro Ala Leu Gly Asp Ser Glu Ile
            1070                1075                1080
Leu Lys Lys Gln Leu Lys Gln Cys Arg Leu Leu Val Ser Asp Ile
            1085                1090                1095
Gln Thr Ile Gln Pro Ser Leu Asn Ser Val Asn Glu Gly Gly Gln
            1100                1105                1110
Lys Ile Lys Asn Glu Ala Glu Pro Glu Phe Ala Ser Arg Leu Glu
            1115                1120                1125
Thr Glu Leu Lys Glu Leu Asn Thr Gln Trp Asp His Met Cys Gln
            1130                1135                1140
Gln Val Tyr Ala Arg Lys Glu Ala Leu Lys Gly Gly Leu Glu Lys
            1145                1150                1155
Thr Val Ser Leu Gln Lys Asp Leu Ser Glu Met His Glu Trp Met
            1160                1165                1170
Thr Gln Ala Glu Glu Glu Tyr Leu Glu Arg Asp Phe Glu Tyr Lys
            1175                1180                1185
Thr Pro Asp Glu Leu Gln Lys Ala Val Glu Glu Met Lys Arg Ala
            1190                1195                1200
```

-continued

```
Lys Glu Glu Ala Gln Gln Lys Glu Ala Lys Val Lys Leu Leu Thr
1205                1210                1215

Glu Ser Val Asn Ser Val Ile Ala Gln Ala Pro Pro Val Ala Gln
1220                1225                1230

Glu Ala Leu Lys Lys Glu Leu Glu Thr Leu Thr Thr Asn Tyr Gln
1235                1240                1245

Trp Leu Cys Thr Arg Leu Asn Gly Lys Cys Lys Thr Leu Glu Glu
1250                1255                1260

Val Trp Ala Cys Trp His Glu Leu Leu Ser Tyr Leu Glu Lys Ala
1265                1270                1275

Asn Lys Trp Leu Asn Glu Val Glu Phe Lys Leu Lys Thr Thr Glu
1280                1285                1290

Asn Ile Pro Gly Gly Ala Glu Glu Ile Ser Glu Val Leu Asp Ser
1295                1300                1305

Leu Glu Asn Leu Met Arg His Ser Glu Asp Asn Pro Asn Gln Ile
1310                1315                1320

Arg Ile Leu Ala Gln Thr Leu Thr Asp Gly Gly Val Met Asp Glu
1325                1330                1335

Leu Ile Asn Glu Glu Leu Glu Thr Phe Asn Ser Arg Trp Arg Glu
1340                1345                1350

Leu His Glu Glu Ala Val Arg Arg Gln Lys Leu Leu Glu Gln Ser
1355                1360                1365

Ile Gln Ser Ala Gln Glu Thr Glu Lys Ser Leu His Leu Ile Gln
1370                1375                1380

Glu Ser Leu Thr Phe Ile Asp Lys Gln Leu Ala Ala Tyr Ile Ala
1385                1390                1395

Asp Lys Val Asp Ala Ala Gln Met Pro Gln Glu Ala Gln Lys Ile
1400                1405                1410

Gln Ser Asp Leu Thr Ser His Glu Ile Ser Leu Glu Glu Met Lys
1415                1420                1425

Lys His Asn Gln Gly Lys Glu Ala Ala Gln Arg Val Leu Ser Gln
1430                1435                1440

Ile Asp Val Ala Gln Lys Lys Leu Gln Asp Val Ser Met Lys Phe
1445                1450                1455

Arg Leu Phe Gln Lys Pro Ala Asn Phe Glu Leu Arg Leu Gln Glu
1460                1465                1470

Ser Lys Met Ile Leu Asp Glu Val Lys Met His Leu Pro Ala Leu
1475                1480                1485

Glu Thr Lys Ser Val Glu Gln Glu Val Val Gln Ser Gln Leu Asn
1490                1495                1500

His Cys Val Asn Leu Tyr Lys Ser Leu Ser Glu Val Lys Ser Glu
1505                1510                1515

Val Glu Met Val Ile Lys Thr Gly Arg Gln Ile Val Gln Lys Lys
1520                1525                1530

Gln Thr Glu Asn Pro Lys Glu Leu Asp Glu Arg Val Thr Ala Leu
1535                1540                1545

Lys Leu His Tyr Asn Glu Leu Gly Ala Lys Val Thr Glu Arg Lys
1550                1555                1560

Gln Gln Leu Glu Lys Cys Leu Lys Leu Ser Arg Lys Met Arg Lys
1565                1570                1575

Glu Met Asn Val Leu Thr Glu Trp Leu Ala Ala Thr Asp Met Glu
1580                1585                1590

Leu Thr Lys Arg Ser Ala Val Glu Gly Met Pro Ser Asn Leu Asp
```

-continued

```
            1595                1600                1605
Ser Glu Val Ala Trp Gly Lys Ala Thr Gln Lys Glu Ile Glu Lys
    1610                1615                1620

Gln Lys Val His Leu Lys Ser Ile Thr Glu Val Gly Glu Ala Leu
    1625                1630                1635

Lys Thr Val Leu Gly Lys Lys Glu Thr Leu Val Glu Asp Lys Leu
    1640                1645                1650

Ser Leu Leu Asn Ser Asn Trp Ile Ala Val Thr Ser Arg Ala Glu
    1655                1660                1665

Glu Trp Leu Asn Leu Leu Leu Glu Tyr Gln Lys His Met Glu Thr
    1670                1675                1680

Phe Asp Gln Asn Val Asp His Ile Thr Lys Trp Ile Ile Gln Ala
    1685                1690                1695

Asp Thr Leu Leu Asp Glu Ser Glu Lys Lys Lys Pro Gln Gln Lys
    1700                1705                1710

Glu Asp Val Leu Lys Arg Leu Lys Ala Glu Leu Asn Asp Ile Arg
    1715                1720                1725

Pro Lys Val Asp Ser Thr Arg Asp Gln Ala Ala Asn Leu Met Ala
    1730                1735                1740

Asn Arg Gly Asp His Cys Arg Lys Leu Val Glu Pro Gln Ile Ser
    1745                1750                1755

Glu Leu Asn His Arg Phe Ala Ala Ile Ser His Arg Ile Lys Thr
    1760                1765                1770

Gly Lys Ala Ser Ile Pro Leu Lys Glu Leu Glu Gln Phe Asn Ser
    1775                1780                1785

Asp Ile Gln Lys Leu Leu Glu Pro Leu Glu Ala Glu Ile Gln Gln
    1790                1795                1800

Gly Val Asn Leu Lys Glu Glu Asp Phe Asn Lys Asp Met Asn Glu
    1805                1810                1815

Asp Asn Glu Gly Thr Val Lys Glu Leu Leu Gln Arg Gly Asp Asn
    1820                1825                1830

Leu Gln Gln Arg Ile Thr Asp Glu Arg Lys Arg Glu Glu Ile Lys
    1835                1840                1845

Ile Lys Gln Gln Leu Leu Gln Thr Lys His Asn Ala Leu Lys Asp
    1850                1855                1860

Leu Arg Ser Gln Arg Arg Lys Lys Ala Leu Glu Ile Ser His Gln
    1865                1870                1875

Trp Tyr Gln Tyr Lys Arg Gln Ala Asp Asp Leu Leu Lys Cys Leu
    1880                1885                1890

Asp Asp Ile Glu Lys Lys Leu Ala Ser Leu Pro Glu Pro Arg Asp
    1895                1900                1905

Glu Arg Lys Ile Lys Glu Ile Asp Arg Glu Leu Gln Lys Lys Lys
    1910                1915                1920

Glu Glu Leu Asn Ala Val Arg Arg Gln Ala Glu Gly Leu Ser Glu
    1925                1930                1935

Asp Gly Ala Ala Met Ala Val Glu Pro Thr Gln Ile Gln Leu Ser
    1940                1945                1950

Lys Arg Trp Arg Glu Ile Glu Ser Lys Phe Ala Gln Phe Arg Arg
    1955                1960                1965

Leu Asn Phe Ala Gln Ile His Thr Val Arg Glu Glu Thr Met Met
    1970                1975                1980

Val Met Thr Glu Asp Met Pro Leu Glu Ile Ser Tyr Val Pro Ser
    1985                1990                1995
```

-continued

Thr Tyr Leu Thr Glu Ile Thr His Val Ser Gln Ala Leu Leu Glu
2000                2005                2010

Val Glu Gln Leu Leu Asn Ala Pro Asp Leu Cys Ala Lys Asp Phe
2015                2020                2025

Glu Asp Leu Phe Lys Gln Glu Ser Leu Lys Asn Ile Lys Asp
2030                2035                2040

Ser Leu Gln Gln Ser Ser Gly Arg Ile Asp Ile His Ser Lys
2045                2050                2055

Lys Thr Ala Ala Leu Gln Ser Ala Thr Pro Val Glu Arg Val Lys
2060                2065                2070

Leu Gln Glu Ala Leu Ser Gln Leu Asp Phe Gln Trp Glu Lys Val
2075                2080                2085

Asn Lys Met Tyr Lys Asp Arg Gln Gly Arg Phe Asp Arg Ser Val
2090                2095                2100

Glu Lys Trp Arg Arg Phe His Tyr Asp Ile Lys Ile Phe Asn Gln
2105                2110                2115

Trp Leu Thr Glu Ala Glu Gln Phe Leu Arg Lys Thr Gln Ile Pro
2120                2125                2130

Glu Asn Trp Glu His Ala Lys Tyr Lys Trp Tyr Leu Lys Glu Leu
2135                2140                2145

Gln Asp Gly Ile Gly Gln Arg Gln Thr Val Val Arg Thr Leu Asn
2150                2155                2160

Ala Thr Gly Glu Glu Ile Ile Gln Gln Ser Ser Lys Thr Asp Ala
2165                2170                2175

Ser Ile Leu Gln Glu Lys Leu Gly Ser Leu Asn Leu Arg Trp Gln
2180                2185                2190

Glu Val Cys Lys Gln Leu Ser Asp Arg Lys Lys Arg Leu Glu Glu
2195                2200                2205

Gln Lys Asn Ile Leu Ser Glu Phe Gln Arg Asp Leu Asn Glu Phe
2210                2215                2220

Val Leu Trp Leu Glu Glu Ala Asp Asn Ile Ala Ser Ile Pro Leu
2225                2230                2235

Glu Pro Gly Lys Glu Gln Gln Leu Lys Glu Lys Leu Glu Gln Val
2240                2245                2250

Lys Leu Leu Val Glu Glu Leu Pro Leu Arg Gln Gly Ile Leu Lys
2255                2260                2265

Gln Leu Asn Glu Thr Gly Gly Pro Val Leu Val Ser Ala Pro Ile
2270                2275                2280

Ser Pro Glu Glu Gln Asp Lys Leu Glu Asn Lys Leu Lys Gln Thr
2285                2290                2295

Asn Leu Gln Trp Ile Lys Val Ser Arg Ala Leu Pro Glu Lys Gln
2300                2305                2310

Gly Glu Ile Glu Ala Gln Ile Lys Asp Leu Gly Gln Leu Glu Lys
2315                2320                2325

Lys Leu Glu Asp Leu Glu Glu Gln Leu Asn His Leu Leu Leu Trp
2330                2335                2340

Leu Ser Pro Ile Arg Asn Gln Leu Glu Ile Tyr Asn Gln Pro Asn
2345                2350                2355

Gln Glu Gly Pro Phe Asp Val Gln Glu Thr Glu Ile Ala Val Gln
2360                2365                2370

Ala Lys Gln Pro Asp Val Glu Glu Ile Leu Ser Lys Gly Gln His
2375                2380                2385

```
Leu Tyr Lys Glu Lys Pro Ala Thr Gln Pro Val Lys Arg Lys Leu
2390                2395                2400

Glu Asp Leu Ser Ser Glu Trp Lys Ala Val Asn Arg Leu Leu Gln
2405                2410                2415

Glu Leu Arg Ala Lys Gln Pro Asp Leu Ala Pro Gly Leu Thr Thr
2420                2425                2430

Ile Gly Ala Ser Pro Thr Gln Thr Val Thr Leu Val Thr Gln Pro
2435                2440                2445

Val Val Thr Lys Glu Thr Ala Ile Ser Lys Leu Glu Met Pro Ser
2450                2455                2460

Ser Leu Met Leu Glu Val Pro Ala Leu Ala Asp Phe Asn Arg Ala
2465                2470                2475

Trp Thr Glu Leu Thr Asp Trp Leu Ser Leu Leu Asp Gln Val Ile
2480                2485                2490

Lys Ser Gln Arg Val Met Val Gly Asp Leu Glu Asp Ile Asn Glu
2495                2500                2505

Met Ile Ile Lys Gln Lys Ala Thr Met Gln Asp Leu Glu Gln Arg
2510                2515                2520

Arg Pro Gln Leu Glu Glu Leu Ile Thr Ala Ala Gln Asn Leu Lys
2525                2530                2535

Asn Lys Thr Ser Asn Gln Glu Ala Arg Thr Ile Ile Thr Asp Arg
2540                2545                2550

Ile Glu Arg Ile Gln Asn Gln Trp Asp Glu Val Gln Glu His Leu
2555                2560                2565

Gln Asn Arg Arg Gln Gln Leu Asn Glu Met Leu Lys Asp Ser Thr
2570                2575                2580

Gln Trp Leu Glu Ala Lys Glu Ala Glu Gln Val Leu Gly Gln
2585                2590                2595

Ala Arg Ala Lys Leu Glu Ser Trp Lys Glu Gly Pro Tyr Thr Val
2600                2605                2610

Asp Ala Ile Gln Lys Lys Ile Thr Glu Thr Lys Gln Leu Ala Lys
2615                2620                2625

Asp Leu Arg Gln Trp Gln Thr Asn Val Asp Val Ala Asn Asp Leu
2630                2635                2640

Ala Leu Lys Leu Leu Arg Asp Tyr Ser Ala Asp Asp Thr Arg Lys
2645                2650                2655

Val His Met Ile Thr Glu Asn Ile Asn Ala Ser Trp Arg Ser Ile
2660                2665                2670

His Lys Arg Val Ser Glu Arg Glu Ala Ala Leu Glu Glu Thr His
2675                2680                2685

Arg Leu Leu Gln Gln Phe Pro Leu Asp Leu Glu Lys Phe Leu Ala
2690                2695                2700

Trp Leu Thr Glu Ala Glu Thr Thr Ala Asn Val Leu Gln Asp Ala
2705                2710                2715

Thr Arg Lys Glu Arg Leu Leu Glu Asp Ser Lys Gly Val Lys Glu
2720                2725                2730

Leu Met Lys Gln Trp Gln Asp Leu Gln Gly Glu Ile Glu Ala His
2735                2740                2745

Thr Asp Val Tyr His Asn Leu Asp Glu Asn Ser Gln Lys Ile Leu
2750                2755                2760

Arg Ser Leu Glu Gly Ser Asp Asp Ala Val Leu Leu Gln Arg Arg
2765                2770                2775

Leu Asp Asn Met Asn Phe Lys Trp Ser Glu Leu Arg Lys Lys Ser
```

```
                    2780                2785                2790
Leu Asn Ile Arg Ser His Leu Glu Ala Ser Ser Asp Gln Trp Lys
    2795                2800                2805

Arg Leu His Leu Ser Leu Gln Glu Leu Leu Val Trp Leu Gln Leu
    2810                2815                2820

Lys Asp Asp Glu Leu Ser Arg Gln Ala Pro Ile Gly Gly Asp Phe
    2825                2830                2835

Pro Ala Val Gln Lys Gln Asn Asp Val His Arg Ala Phe Lys Arg
    2840                2845                2850

Glu Leu Lys Thr Lys Glu Pro Val Ile Met Ser Thr Leu Glu Thr
    2855                2860                2865

Val Arg Ile Phe Leu Thr Glu Gln Pro Leu Glu Gly Leu Glu Lys
    2870                2875                2880

Leu Tyr Gln Glu Pro Arg Glu Leu Pro Pro Glu Glu Arg Ala Gln
    2885                2890                2895

Asn Val Thr Arg Leu Leu Arg Lys Gln Ala Glu Glu Val Asn Thr
    2900                2905                2910

Glu Trp Glu Lys Leu Asn Leu His Ser Ala Asp Trp Gln Arg Lys
    2915                2920                2925

Ile Asp Glu Thr Leu Glu Arg Leu Gln Glu Leu Gln Glu Ala Thr
    2930                2935                2940

Asp Glu Leu Asp Leu Lys Leu Arg Gln Ala Glu Val Ile Lys Gly
    2945                2950                2955

Ser Trp Gln Pro Val Gly Asp Leu Leu Ile Asp Ser Leu Gln Asp
    2960                2965                2970

His Leu Glu Lys Val Lys Ala Leu Arg Gly Glu Ile Ala Pro Leu
    2975                2980                2985

Lys Glu Asn Val Ser His Val Asn Asp Leu Ala Arg Gln Leu Thr
    2990                2995                3000

Thr Leu Gly Ile Gln Leu Ser Pro Tyr Asn Leu Ser Thr Leu Glu
    3005                3010                3015

Asp Leu Asn Thr Arg Trp Lys Leu Leu Gln Val Ala Val Glu Asp
    3020                3025                3030

Arg Val Arg Gln Leu His Glu Ala His Arg Asp Phe Gly Pro Ala
    3035                3040                3045

Ser Gln His Phe Leu Ser Thr Ser Val Gln Gly Pro Trp Glu Arg
    3050                3055                3060

Ala Ile Ser Pro Asn Lys Val Pro Tyr Tyr Ile Asn His Glu Thr
    3065                3070                3075

Gln Thr Thr Cys Trp Asp His Pro Lys Met Thr Glu Leu Tyr Gln
    3080                3085                3090

Ser Leu Ala Asp Leu Asn Asn Val Arg Phe Ser Ala Tyr Arg Thr
    3095                3100                3105

Ala Met Lys Leu Arg Arg Leu Gln Lys Ala Leu Cys Leu Asp Leu
    3110                3115                3120

Leu Ser Leu Ser Ala Ala Cys Asp Ala Leu Asp Gln His Asn Leu
    3125                3130                3135

Lys Gln Asn Asp Gln Pro Met Asp Ile Leu Gln Ile Ile Asn Cys
    3140                3145                3150

Leu Thr Thr Ile Tyr Asp Arg Leu Glu Gln Glu His Asn Asn Leu
    3155                3160                3165

Val Asn Val Pro Leu Cys Val Asp Met Cys Leu Asn Trp Leu Leu
    3170                3175                3180
```

```
Asn Val Tyr Asp Thr Gly Arg Thr Gly Arg Ile Arg Val Leu Ser
3185                3190                3195

Phe Lys Thr Gly Ile Ile Ser Leu Cys Lys Ala His Leu Glu Asp
3200                3205                3210

Lys Tyr Arg Tyr Leu Phe Lys Gln Val Ala Ser Ser Thr Gly Phe
3215                3220                3225

Cys Asp Gln Arg Arg Leu Gly Leu Leu Leu His Asp Ser Ile Gln
3230                3235                3240

Ile Pro Arg Gln Leu Gly Glu Val Ala Ser Phe Gly Gly Ser Asn
3245                3250                3255

Ile Glu Pro Ser Val Arg Ser Cys Phe Gln Phe Ala Asn Asn Lys
3260                3265                3270

Pro Glu Ile Glu Ala Ala Leu Phe Leu Asp Trp Met Arg Leu Glu
3275                3280                3285

Pro Gln Ser Met Val Trp Leu Pro Val Leu His Arg Val Ala Ala
3290                3295                3300

Ala Glu Thr Ala Lys His Gln Ala Lys Cys Asn Ile Cys Lys Glu
3305                3310                3315

Cys Pro Ile Ile Gly Phe Arg Tyr Arg Ser Leu Lys His Phe Asn
3320                3325                3330

Tyr Asp Ile Cys Gln Ser Cys Phe Phe Ser Gly Arg Val Ala Lys
3335                3340                3345

Gly His Lys Met His Tyr Pro Met Val Glu Tyr Cys Thr Pro Thr
3350                3355                3360

Thr Ser Gly Glu Asp Val Arg Asp Phe Ala Lys Val Leu Lys Asn
3365                3370                3375

Lys Phe Arg Thr Lys Arg Tyr Phe Ala Lys His Pro Arg Met Gly
3380                3385                3390

Tyr Leu Pro Val Gln Thr Val Leu Glu Gly Asp Asn Met Glu Thr
3395                3400                3405

Pro Val Thr Leu Ile Asn Phe Trp Pro Val Asp Ser Ala Pro Ala
3410                3415                3420

Ser Ser Pro Gln Leu Ser His Asp Asp Thr His Ser Arg Ile Glu
3425                3430                3435

His Tyr Ala Ser Arg Leu Ala Glu Met Glu Asn Ser Asn Gly Ser
3440                3445                3450

Tyr Leu Asn Asp Ser Ile Ser Pro Asn Glu Ser Ile Asp Asp Glu
3455                3460                3465

His Leu Leu Ile Gln His Tyr Cys Gln Ser Leu Asn Gln Asp Ser
3470                3475                3480

Pro Leu Ser Gln Pro Arg Ser Pro Ala Gln Ile Leu Ile Ser Leu
3485                3490                3495

Glu Ser Glu Glu Arg Gly Glu Leu Glu Arg Ile Leu Ala Asp Leu
3500                3505                3510

Glu Glu Glu Asn Arg Asn Leu Gln Ala Glu Tyr Asp Arg Leu Lys
3515                3520                3525

Gln Gln His Glu His Lys Gly Leu Ser Pro Leu Pro Ser Pro Pro
3530                3535                3540

Glu Met Met Pro Thr Ser Pro Gln Ser Pro Arg Asp Ala Glu Leu
3545                3550                3555

Ile Ala Glu Ala Lys Leu Leu Arg Gln His Lys Gly Arg Leu Glu
3560                3565                3570
```

Ala Arg Met Gln Ile Leu Glu Asp His Asn Lys Gln Leu Glu Ser
3575                3580                3585

Gln Leu His Arg Leu Arg Gln Leu Leu Glu Gln Pro Gln Ala Glu
3590                3595                3600

Ala Lys Val Asn Gly Thr Thr Val Ser Ser Pro Ser Thr Ser Leu
3605                3610                3615

Gln Arg Ser Asp Ser Ser Gln Pro Met Leu Leu Arg Val Val Gly
3620                3625                3630

Ser Gln Thr Ser Asp Ser Met Gly Glu Glu Asp Leu Leu Ser Pro
3635                3640                3645

Pro Gln Asp Thr Ser Thr Gly Leu Glu Glu Val Met Glu Gln Leu
3650                3655                3660

Asn Asn Ser Phe Pro Ser Ser Arg Gly Arg Asn Thr Pro Gly Lys
3665                3670                3675

Pro Leu Gly Leu Trp Ala Leu Lys Cys Leu Leu Tyr Leu Ala Phe
3680                3685                3690

Leu Phe Ile Gly Val Asn Cys Lys Phe Thr Ile Val Phe Pro His
3695                3700                3705

Asn Gln Lys Gly Asn Trp Lys Asn Val Pro Ser Asn Tyr His Tyr
3710                3715                3720

Cys Pro Ser Ser Ser Asp Leu Asn Trp His Asn Asp Leu Ile Gly
3725                3730                3735

Thr Ala Leu Gln Val Lys Met Pro Lys Ser His Lys Ala Ile Gln
3740                3745                3750

Ala Asp Gly Trp Met Cys His Ala Ser Lys Trp Val Thr Thr Cys
3755                3760                3765

Asp Phe Arg Trp Tyr Gly Pro Lys Tyr Ile Thr His Ser Ile Arg
3770                3775                3780

Ser Phe Thr Pro Ser Val Glu Gln Cys Lys Glu Ser Ile Glu Gln
3785                3790                3795

Thr Lys Gln Gly Thr Trp Leu Asn Pro Gly Phe Pro Pro Gln Ser
3800                3805                3810

Cys Gly Tyr Ala Thr Val Thr Asp Ala Glu Ala Ala Ile Val Gln
3815                3820                3825

Val Thr Pro His His Val Leu Val Asp Glu Tyr Thr Gly Glu Trp
3830                3835                3840

Val Asp Ser Gln Phe Ile Asn Gly Lys Cys Ser Asn Asp Ile Cys
3845                3850                3855

Pro Thr Val His Asn Ser Thr Thr Trp His Ser Asp Tyr Lys Val
3860                3865                3870

Lys Gly Leu Cys Asp Ser Asn Leu Ile Ser Thr Asp Ile Thr Phe
3875                3880                3885

Phe Ser Glu Asp Gly Glu Leu Ser Ser Leu Gly Lys Glu Gly Thr
3890                3895                3900

Gly Phe Arg Ser Asn Tyr Phe Ala Tyr Glu Thr Gly Asp Lys Ala
3905                3910                3915

Cys Lys Met Gln Tyr Cys Lys His Trp Gly Val Arg Leu Pro Ser
3920                3925                3930

Gly Val Trp Phe Glu Met Ala Asp Lys Asp Leu Phe Ala Ala Ala
3935                3940                3945

Arg Phe Pro Glu Cys Pro Glu Gly Ser Ser Ile Ser Ala Pro Ser
3950                3955                3960

Gln Thr Ser Val Asp Val Ser Leu Ile Gln Asp Val Glu Arg Ile

Leu Asp Tyr Ser Leu Cys Gln Glu Thr Trp Ser Lys Ile Arg Ala
3965                3970                3975
          3980                3985                3990

Gly Leu Pro Ile Ser Pro Val Leu Ser Tyr Leu Ala Pro Lys Asn
          3995                4000                4005

Pro Gly Thr Gly Pro Val Phe Thr Ile Ile Asn Gly Thr Leu Lys
          4010                4015                4020

Tyr Phe Glu Thr Arg Tyr Ile Arg Val Asp Ile Ala Ala Pro Ile
          4025                4030                4035

Leu Ser Arg Met Val Gly Met Ile Ser Gly Thr Thr Thr Glu Arg
          4040                4045                4050

Glu Leu Trp Asp Asp Trp Ala Pro Tyr Glu Asp Val Glu Ile Gly
          4055                4060                4065

Pro Asn Gly Val Leu Arg Thr Ser Leu Gly Tyr Lys Phe Pro Leu
          4070                4075                4080

Tyr Met Ile Gly His Gly Met Leu Asp Ser Asp Leu His Leu Ser
          4085                4090                4095

Ser Lys Ala Gln Val Phe Glu His Pro His Ile Gln Asp Ala Ala
          4100                4105                4110

Ser Gln Leu Pro Asp Asp Glu Thr Leu Phe Phe Gly Asp Thr Gly
          4115                4120                4125

Leu Ser Lys Asn Pro Ile Glu Phe Val Glu Gly Trp Phe Ser Ser
          4130                4135                4140

Trp Lys Ser Ser Ile Ala Ser Phe Phe Phe Ile Ile Gly Leu Ile
          4145                4150                4155

Ile Gly Leu Phe Leu Val Leu Arg Val Gly Ile Tyr Leu Cys Ile
          4160                4165                4170

Lys Leu Lys His Thr Lys Lys Arg Gln Ile Tyr Thr Asp Ile Glu
          4175                4180                4185

Met Asn Arg Leu Gly Lys
          4190

<210> SEQ ID NO 7
<211> LENGTH: 7482
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic nucleotide sequence of proposed Dystrophin (truncated)
      -VSV-G chimeric protein with VSV-G at C-terminal"

<400> SEQUENCE: 7
atgctttggt gggaagaagt agaggactgt tatgaaagag aagatgttca aaagaaaaca    60
ttcacaaaat gggtaaatgc acaatttct aagtttggga agcagcatat tgagaacctc   120
ttcagtgacc tacaggatgg gaggcgcctc ctagacctcc tcgaaggcct gacagggcaa   180
aaactgccaa agaaaaagg atccacaaga gttcatgccc tgaacaatgt caacaaggca   240
ctgcgggttt tgcagaacaa taatgttgat ttagtgaata ttggaagtac tgacatcgta   300
gatggaaatc ataaactgac tcttggtttg atttggaata taatcctcca ctggcaggtc   360
aaaaatgtaa tgaaaatat catggctgga ttgcaacaaa ccaacagtga aaagattctc   420
ctgagctggg tccgacaatc aactcgtaat tatccacagg ttaatgtaat caacttcacc   480
accagctggt ctgatggcct ggctttgaat gctctcatcc atagtcatag gccagaccta   540
tttgactgga atagtgtggt tgccagcag tcagccacac aacgactgga acatgcattc   600

```
aacatcgcca gatatcaatt aggcatagag aaactactcg atcctgaaga tgttgatacc     660
acctatccag ataagaagtc catcttaatg tacatcacat cactcttcca agttttgcct     720
caacaagtga gcattgaagc catccaggaa gtggaaatgt tgccaaggcc acctaaagtg     780
actaaagaag aacattttca gttacatcat caaatgcact attctcaaca gatcacggtc     840
agtctagcac agggatatga gagaacttct tcccctaagc ctcgattcaa gagctatgcc     900
tacacacagg ctgcttatgt caccacctct gaccctacac ggagcccatt tccttcacag     960
catttggaag ctcctgaaga caagtcattt ggcagttcat tgatggagag tgaagtaaac    1020
ctggaccgtt atcaaacagc tttagaagaa gtattatcgt ggcttctttc tgctgaggac    1080
acattgcaag cacaaggaga gatttctaat gatgtggaag tggtgaaaga ccagtttcat    1140
actcatgagg ggtacatgat ggatttgaca gcccatcagg gccgggttgg taatattcta    1200
caattgggaa gtaagctgat tggaacagga aaattatcag aagatgaaga aactgaagta    1260
caagagcaga tgaatctcct aaattcaaga tgggaatgcc tcagggtagc tagcatggaa    1320
aaacaaagca atttacatag agttttaatg gatctccaga atcagaaact gaaagagttg    1380
aatgactggc taacaaaaac agaagaaaga acaaggaaaa tggaggaaga gcctcttgga    1440
cctgatcttg aagacctaaa acgccaagta caacaacata aggtgcttca agaagatcta    1500
gaacaagaac aagtcagggt caattctctc actcacatgg tggtggtagt tgatgaatct    1560
agtggagatc acgcaactgc tgctttggaa gaacaactta aggtattggg agatcgatgg    1620
gcaaacatct gtagatggac agaagaccgc tgggttcttt tacaagacat ccttctcaaa    1680
tggcaacgtc ttactgaaga acagtgcctt tttagtgcat ggctttcaga aaagaagat    1740 gcagtgaaca agattcacac aactggcttt aaagatcaaa atgaaatgtt atcaagtctt    1800
caaaaactgg ccgtttttaaa agcggatcta gaaaagaaaa agcaatccat gggcaaactg    1860
tattcactca aacaagatct tctttcaaca ctgaagaata agtcagtgac ccagaagacg    1920
gaagcatggc tggataactt tgcccggtgt tgggataatt tagtccaaaa acttgaaaag    1980
agtacagcac aggaaactga aatagcagtt caagctaaac aaccggatgt ggaagagatt    2040
ttgtctaaag ggcagcattt gtacaaggaa aaaccagcca ctcagccagt gaagaggaag    2100
ttagaagatc tgagctctga gtggaaggcg gtaaaccgtt tacttcaaga gctgagggca    2160
aagcagcctg acctagctcc tggactgacc actattggag cctctcctac tcagactgtt    2220
actctggtga cacaacctgt ggttactaag gaaactgcca tctccaaact agaaatgcca    2280
tcttccttga tgttggaggt acctgctctg cagatttca accgggcttg dacagaactt    2340
accgactggc tttctctgct tgatcaagtt ataaaatcac agagggtgat ggtgggtgac    2400
cttgaggata tcaacgagat gatcatcaag cagaaggcaa caatgcagga tttggaacag    2460
aggcgtcccc agttggaaga actcattacc gctgcccaaa atttgaaaaa caagaccagc    2520
aatcaagagg ctagaacaat cattacggat cgaattgaaa gaattcagaa tcagtgggat    2580
gaagtacaag aacaccttca gaaccggagg caacagttga atgaaatgtt aaaggattca    2640
acacaatggc tggaagctaa ggaagaagct gagcaggtct taggacaggc cagagccaag    2700
cttgagtcat ggaaggaggg tccctataca gtagatgcaa tccaaaagaa aatcacagaa    2760
accaagcagt tggccaaaga cctccgccag tggcagacaa atgtagatgt ggcaaatgac    2820 ttggcccctga aacttctccg ggattattct gcagatgata ccagaaaagt ccacatgata    2880
acagagaata tcaatgcctc ttggagaagc attcataaaa gggtgagtga gcgagaggct    2940
```

```
gctttggaag aaactcatag attactgcaa cagttccccc tggacctgga aaagtttctt    3000
gcctggctta cagaagctga acaactgcc aatgtcctac aggatgctac ccgtaaggaa     3060
aggctcctag aagactccaa gggagtaaaa gagctgatga acaatggca agacctccaa     3120 ggtgaaattg aagctcacac agatgtttat cacaacctgg atgaaaacag ccaaaaaatc    3180
ctgagatccc tggaaggttc cgatgatgca gtcctgttac aaagacgttt ggataacatg    3240
aacttcaagt ggagtgaact tcggaaaaag tctctcaaca ttaggtccca tttggaagcc    3300
agttctgacc agtggaagcg tctgcacctt tctctgcagg aacttctggt gtggctacag    3360
ctgaaagatg atgaattaag ccggcaggca cctattggag gcgactttcc agcagttcag    3420
aagcagaacg atgtacatag ggccttcaag agggaattga aaactaaaga acctgtaatc    3480
atgagtactc ttgagactgt acgaatattt ctgacagagc agcctttgga aggactagag    3540
aaactctacc aggagcccag agagctgcct cctgaggaga gagcccagaa tgtcactcgg    3600
cttctacgaa agcaggctga ggaggtcaat actgagtggg aaaaattgaa cctgcactcc    3660
gctgactggc agagaaaaat agatgagacc cttgaaaagc tccaggaact tcaagaggcc    3720
acggatgagc tggacctcaa gctgcgccaa gctgaggtga tcaagggatc ctggcagccc    3780
gtgggcgatc tcctcattga ctctctccaa gatcacctcg agaaagtcaa ggcacttcga    3840
ggagaaattg cgcctctgaa agagaacgtg agccacgtca atgaccttgc tcgccagctt    3900
accactttgg gcattcagct ctcaccgtat aacctcagca ctctggaaga cctgaacacc    3960
agatggaagc ttctgcaggt ggccgtcgag gaccgagtca ggcagctgca tgaagcccac    4020
agggactttg gtccagcatc tcagcacttt ctttccacgt ctgtccaggg tccctgggag    4080
agagccatct cgccaaacaa agtgccctac tatatcaacc acgagactca aacaacttgc    4140
tgggaccatc ccaaaatgac agagctctac cagtctttag ctgacctgaa taatgtcaga    4200
ttctcagctt ataggactgc catgaaactc cgaagactgc agaaggccct ttgcttggat    4260
ctcttgagcc tgtcagctgc atgtgatgcc ttggaccagc acaacctcaa gcaaaatgac    4320
cagcccatgg atatcctgca gattattaat tgtttgacca ctatttatga ccgcctggag    4380
caagagcaca caaatttggt caacgtccct ctctgcgtgg atatgtgtct gaactggctg    4440
ctgaatgttt atgatacggg acgaacaggg aggatccgtg tcctgtcttt taaaactggc    4500
atcatttccc tgtgtaaagc acatttggaa gacaagtaca gataccttt caagcaagtg    4560 gcaagttcaa caggattttg tgaccagcgc aggctgggcc tccttctgca tgattctatc    4620
caaattccaa gacagttggg tgaagttgca tcctttgggg gcagtaacat tgagccaagt    4680
gtccggagct gcttccaatt tgctaataat aagccagaga tcgaagcggc cctcttccta    4740
gactggatga actggaacc ccagtccatg gtgtggctgc ccgtcctgca cagagtggct     4800
gctgcagaaa ctgccaagca tcaggccaaa tgtaacatct gcaaagagtg tccaatcatt    4860
ggattcaggt acaggagtct aaagcacttt aattatgaca tctgccaaag ctgctttttt    4920
tctggtcgag ttgcaaaagg ccataaaatg cactatccca tggtggaata ttgcactccg    4980
actacatcag agaagatgt tcgagacttt gccaaggtac taaaaaacaa atttcgaacc    5040
aaaaggtatt ttgcgaagca tccccgaatg ggctacctgc cagtgcagac tgtcttagag    5100
ggggacaaca tggaaactcc cgttactctg atcaacttct ggccagtaga ttctgcgcct    5160
gcctcgtccc ctcagctttc acacgatgat actcattcac gcattgaaca ttatgctagc    5220
aggctagcag aaatgcgaaaa cagcaatgga tcttatctaa atgatagcat ctctcctaat    5280
gagagcatag atgatgaaca tttgttaatc cagcattact gccaaagttt gaaccaggac    5340
```

```
tcccccctga gccagcctcg tagtcctgcc cagatcttga tttccttaga gagtgaggaa    5400 agagggagc tagagagaat cctagcagat cttgaggaag aaaacaggaa tctgcaagca     5460
gaatatgacc gtctaaagca gcagcacgaa cataaaggcc tgtccccact gccgtcccct    5520
cctgaaatga tgcccacctc tccccagagt ccccgggatg ctgagctcat tgctgaggcc    5580
aagctactgc gtcaacacaa aggccgcctg gaagccagga tgcaaatcct ggaagaccac    5640
aataaacagc tggagtcaca gttacacagg ctaaggcagc tgctggagca accccaggca    5700
gaggccaaag tgaatggcac aacggtgtcc tctccttcta cctctctaca gaggtccgac    5760
agcagtcagc ctatgctgct ccgagtggtt ggcagtcaaa cttcggactc catgggtgag    5820
gaagatcttc tcagtcctcc ccaggacaca agcacagggt tagaggaggt gatggagcaa    5880
ctcaacaact ccttccctag ttcaagagga agaaataccc ctggaaagcc actgggactg    5940
tgggcactga agtgcctttt gtacttagct tttttattca tcggggtgaa ttgcaagttc    6000
accatagttt ttccacacaa ccaaaaagga aactggaaaa atgttccttc caattaccat    6060
tattgcccgt caagctcaga tttaaattgg cataatgact taataggcac agccttacaa    6120
gtcaaaatgc ccaagagtca caaggctatt caagcagacg gttggatgtg tcatgcttcc    6180
aaatgggtca ctacttgtga tttccgctgg tacggaccga agtatataac acattccatc    6240
cgatccttca ctccatctgt agaacaatgc aaggaaagca ttgaacaaac gaaacaagga    6300
acttggctga atccaggctt ccctcctcaa agttgtggat atgcaactgt gacggatgct    6360
gaagcagcga ttgtccaggt gactcctcac catgtgcttg ttgatgaata cacaggagaa    6420
tgggttgatt cacagttcat caacggaaaa tgcagcaatg acatatgccc cactgtccat    6480
aactccacaa cctggcattc cgactataag gtcaaagggc tatgtgattc taacctcatt    6540
tccacggaca tcaccttctt ctcagaggac ggagagctat catccctagg aaaggagggc    6600
acagggttca gaagtaacta ctttgcttat gaaactggag acaaggcctg caaaatgcag    6660
tactgcaagc attggggagt cagactccca tcaggtgtct ggttcgagat ggctgataag    6720
gatctctttg ctgcagccag attccctgaa tgcccagaag ggtcaagtat ctctgctcca    6780
tctcagacct cagtggatgt aagtctcatt caggacgttg agaggatctt ggattattcc    6840
ctctgccaag aaacctggag caaaatcaga gcgggtcttc ccatctctcc agtggatctc    6900
agctatcttg ctcctaaaaa cccaggaacc ggtcctgtct ttaccataat caatggtacc    6960
ctaaaatact ttgagaccag atacatcaga gtcgatattg ctgctccaat cctctcaaga    7020
atggtcggaa tgatcagtgg aactaccaca gaaagggaac tgtgggatga ctgggctcca    7080
tatgaagacg tggaaattgg acccaatgga gttctgagga ccagtttagg atataagttt    7140
cctttatata tgattggaca tggtatgttg gactccgatc ttcatcttag ctcaaaggct    7200
caggtgtttg aacatcctca cattcaagac gctgcttcgc agcttcctga tgatgagact    7260 ttatttttg gtgatactgg gctatccaaa aatccaatcg agtttgtaga aggttggttc    7320
agtagttgga agagctctat tgcctctttt ttctttatca tagggttaat cattggacta    7380
ttcttggttc tccgagttgg tatttatctt tgcattaaat taaagcacac caagaaaaga    7440
cagatttata cagacataga gatgaaccga cttggaaagt aa                      7482
```

<210> SEQ ID NO 8
<211> LENGTH: 2493
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic amino acid sequence of proposed Dystrophin (truncated)
      -VSV-G chimeric protein with VSV-G at C-terminal"

<400> SEQUENCE: 8

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
50                  55                  60

Glu Lys Gly Ser Thr Arg Val His Ala Leu Asn Asn Val Asn Lys Ala
65                  70                  75                  80

Leu Arg Val Leu Gln Asn Asn Val Asp Leu Val Asn Ile Gly Ser
                85                  90                  95

Thr Asp Ile Val Asp Gly Asn His Lys Leu Thr Leu Gly Leu Ile Trp
                100                 105                 110

Asn Ile Ile Leu His Trp Gln Val Lys Asn Val Met Lys Asn Ile Met
                115                 120                 125

Ala Gly Leu Gln Gln Thr Asn Ser Glu Lys Ile Leu Leu Ser Trp Val
            130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
            195                 200                 205

Ile Glu Lys Leu Leu Asp Pro Glu Asp Val Asp Thr Thr Tyr Pro Asp
210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
            245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
        290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
        370                 375                 380
```

```
Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
            405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Asp Glu Ser Ser Gly Asp His Ala Thr Ala Ala
        515                 520                 525

Leu Glu Glu Gln Leu Lys Val Leu Gly Asp Arg Trp Ala Asn Ile Cys
530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575

Glu Lys Glu Asp Ala Val Asn Lys Ile His Thr Thr Gly Phe Lys Asp
            580                 585                 590

Gln Asn Glu Met Leu Ser Ser Leu Gln Lys Leu Ala Val Leu Lys Ala
            595                 600                 605

Asp Leu Glu Lys Lys Lys Gln Ser Met Gly Lys Leu Tyr Ser Leu Lys
    610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Glu Thr Glu Ile Ala Val Gln Ala
            660                 665                 670

Lys Gln Pro Asp Val Glu Glu Ile Leu Ser Lys Gly Gln His Leu Tyr
        675                 680                 685

Lys Glu Lys Pro Ala Thr Gln Pro Val Lys Arg Lys Leu Glu Asp Leu
    690                 695                 700

Ser Ser Glu Trp Lys Ala Val Asn Arg Leu Leu Gln Glu Leu Arg Ala
705                 710                 715                 720

Lys Gln Pro Asp Leu Ala Pro Gly Leu Thr Thr Ile Gly Ala Ser Pro
                725                 730                 735

Thr Gln Thr Val Thr Leu Val Thr Gln Pro Val Val Thr Lys Glu Thr
            740                 745                 750

Ala Ile Ser Lys Leu Glu Met Pro Ser Ser Leu Met Leu Glu Val Pro
        755                 760                 765

Ala Leu Ala Asp Phe Asn Arg Ala Trp Thr Glu Leu Thr Asp Trp Leu
    770                 775                 780

Ser Leu Leu Asp Gln Val Ile Lys Ser Gln Arg Val Met Val Gly Asp
785                 790                 795                 800

Leu Glu Asp Ile Asn Glu Met Ile Ile Lys Gln Lys Ala Thr Met Gln
```

-continued

```
                805                 810                 815
Asp Leu Glu Gln Arg Arg Pro Gln Leu Glu Glu Leu Ile Thr Ala Ala
                820                 825                 830

Gln Asn Leu Lys Asn Lys Thr Ser Asn Gln Glu Ala Arg Thr Ile Ile
                835                 840                 845

Thr Asp Arg Ile Glu Arg Ile Gln Asn Gln Trp Asp Glu Val Gln Glu
                850                 855                 860

His Leu Gln Asn Arg Arg Gln Gln Leu Asn Glu Met Leu Lys Asp Ser
865                 870                 875                 880

Thr Gln Trp Leu Glu Ala Lys Glu Glu Ala Glu Gln Val Leu Gly Gln
                885                 890                 895

Ala Arg Ala Lys Leu Glu Ser Trp Lys Glu Gly Pro Tyr Thr Val Asp
                900                 905                 910

Ala Ile Gln Lys Lys Ile Thr Glu Thr Lys Gln Leu Ala Lys Asp Leu
                915                 920                 925

Arg Gln Trp Gln Thr Asn Val Asp Val Ala Asn Asp Leu Ala Leu Lys
                930                 935                 940

Leu Leu Arg Asp Tyr Ser Ala Asp Asp Thr Arg Lys Val His Met Ile
945                 950                 955                 960

Thr Glu Asn Ile Asn Ala Ser Trp Arg Ser Ile His Lys Arg Val Ser
                965                 970                 975

Glu Arg Glu Ala Ala Leu Glu Glu Thr His Arg Leu Leu Gln Gln Phe
                980                 985                 990

Pro Leu Asp Leu Glu Lys Phe Leu Ala Trp Leu Thr Glu Ala Glu Thr
                995                 1000                1005

Thr Ala Asn Val Leu Gln Asp Ala Thr Arg Lys Glu Arg Leu Leu
                1010                1015                1020

Glu Asp Ser Lys Gly Val Lys Glu Leu Met Lys Gln Trp Gln Asp
                1025                1030                1035

Leu Gln Gly Glu Ile Glu Ala His Thr Asp Val Tyr His Asn Leu
                1040                1045                1050

Asp Glu Asn Ser Gln Lys Ile Leu Arg Ser Leu Glu Gly Ser Asp
                1055                1060                1065

Asp Ala Val Leu Leu Gln Arg Arg Leu Asp Asn Met Asn Phe Lys
                1070                1075                1080

Trp Ser Glu Leu Arg Lys Lys Ser Leu Asn Ile Arg Ser His Leu
                1085                1090                1095

Glu Ala Ser Ser Asp Gln Trp Lys Arg Leu His Leu Ser Leu Gln
                1100                1105                1110

Glu Leu Leu Val Trp Leu Gln Leu Lys Asp Asp Glu Leu Ser Arg
                1115                1120                1125

Gln Ala Pro Ile Gly Gly Asp Phe Pro Ala Val Gln Lys Gln Asn
                1130                1135                1140

Asp Val His Arg Ala Phe Lys Arg Glu Leu Lys Thr Lys Glu Pro
                1145                1150                1155

Val Ile Met Ser Thr Leu Glu Thr Val Arg Ile Phe Leu Thr Glu
                1160                1165                1170

Gln Pro Leu Glu Gly Leu Glu Lys Leu Tyr Gln Glu Pro Arg Glu
                1175                1180                1185

Leu Pro Pro Glu Glu Arg Ala Gln Asn Val Thr Arg Leu Leu Arg
                1190                1195                1200

Lys Gln Ala Glu Glu Val Asn Thr Glu Trp Glu Lys Leu Asn Leu
                1205                1210                1215
```

```
His Ser Ala Asp Trp Gln Arg Lys Ile Asp Glu Thr Leu Glu Arg
1220                 1225                1230

Leu Gln Glu Leu Gln Glu Ala Thr Asp Glu Leu Asp Leu Lys Leu
    1235                1240                1245

Arg Gln Ala Glu Val Ile Lys Gly Ser Trp Gln Pro Val Gly Asp
        1250                1255                1260

Leu Leu Ile Asp Ser Leu Gln Asp His Leu Glu Lys Val Lys Ala
1265                 1270                1275

Leu Arg Gly Glu Ile Ala Pro Leu Lys Glu Asn Val Ser His Val
    1280                1285                1290

Asn Asp Leu Ala Arg Gln Leu Thr Thr Leu Gly Ile Gln Leu Ser
        1295                1300                1305

Pro Tyr Asn Leu Ser Thr Leu Glu Asp Leu Asn Thr Arg Trp Lys
1310                 1315                1320

Leu Leu Gln Val Ala Val Glu Asp Arg Val Arg Gln Leu His Glu
    1325                1330                1335

Ala His Arg Asp Phe Gly Pro Ala Ser Gln His Phe Leu Ser Thr
        1340                1345                1350

Ser Val Gln Gly Pro Trp Glu Arg Ala Ile Ser Pro Asn Lys Val
1355                 1360                1365

Pro Tyr Tyr Ile Asn His Glu Thr Gln Thr Thr Cys Trp Asp His
    1370                1375                1380

Pro Lys Met Thr Glu Leu Tyr Gln Ser Leu Ala Asp Leu Asn Asn
        1385                1390                1395

Val Arg Phe Ser Ala Tyr Arg Thr Ala Met Lys Leu Arg Arg Leu
1400                 1405                1410

Gln Lys Ala Leu Cys Leu Asp Leu Leu Ser Leu Ser Ala Ala Cys
    1415                1420                1425

Asp Ala Leu Asp Gln His Asn Leu Lys Gln Asn Asp Gln Pro Met
        1430                1435                1440

Asp Ile Leu Gln Ile Ile Asn Cys Leu Thr Thr Ile Tyr Asp Arg
1445                 1450                1455

Leu Glu Gln Glu His Asn Asn Leu Val Asn Val Pro Leu Cys Val
    1460                1465                1470

Asp Met Cys Leu Asn Trp Leu Leu Asn Val Tyr Asp Thr Gly Arg
        1475                1480                1485

Thr Gly Arg Ile Arg Val Leu Ser Phe Lys Thr Gly Ile Ile Ser
1490                 1495                1500

Leu Cys Lys Ala His Leu Glu Asp Lys Tyr Arg Tyr Leu Phe Lys
    1505                1510                1515

Gln Val Ala Ser Ser Thr Gly Phe Cys Asp Gln Arg Arg Leu Gly
        1520                1525                1530

Leu Leu Leu His Asp Ser Ile Gln Ile Pro Arg Gln Leu Gly Glu
1535                 1540                1545

Val Ala Ser Phe Gly Gly Ser Asn Ile Glu Pro Ser Val Arg Ser
    1550                1555                1560

Cys Phe Gln Phe Ala Asn Asn Lys Pro Glu Ile Glu Ala Ala Leu
        1565                1570                1575

Phe Leu Asp Trp Met Arg Leu Glu Pro Gln Ser Met Val Trp Leu
1580                 1585                1590

Pro Val Leu His Arg Val Ala Ala Ala Glu Thr Ala Lys His Gln
    1595                1600                1605
```

```
Ala Lys Cys Asn Ile Cys Lys Glu Cys Pro Ile Ile Gly Phe Arg
    1610            1615                1620

Tyr Arg Ser Leu Lys His Phe Asn Tyr Asp Ile Cys Gln Ser Cys
    1625            1630                1635

Phe Phe Ser Gly Arg Val Ala Lys Gly His Lys Met His Tyr Pro
    1640            1645                1650

Met Val Glu Tyr Cys Thr Pro Thr Thr Ser Gly Glu Asp Val Arg
    1655            1660                1665

Asp Phe Ala Lys Val Leu Lys Asn Lys Phe Arg Thr Lys Arg Tyr
    1670            1675                1680

Phe Ala Lys His Pro Arg Met Gly Tyr Leu Pro Val Gln Thr Val
    1685            1690                1695

Leu Glu Gly Asp Asn Met Glu Thr Pro Val Thr Leu Ile Asn Phe
    1700            1705                1710

Trp Pro Val Asp Ser Ala Pro Ala Ser Ser Pro Gln Leu Ser His
    1715            1720                1725

Asp Asp Thr His Ser Arg Ile Glu His Tyr Ala Ser Arg Leu Ala
    1730            1735                1740

Glu Met Glu Asn Ser Asn Gly Ser Tyr Leu Asn Asp Ser Ile Ser
    1745            1750                1755

Pro Asn Glu Ser Ile Asp Asp Glu His Leu Leu Ile Gln His Tyr
    1760            1765                1770

Cys Gln Ser Leu Asn Gln Asp Ser Pro Leu Ser Gln Pro Arg Ser
    1775            1780                1785

Pro Ala Gln Ile Leu Ile Ser Leu Glu Ser Glu Glu Arg Gly Glu
    1790            1795                1800

Leu Glu Arg Ile Leu Ala Asp Leu Glu Glu Asn Arg Asn Leu
    1805            1810                1815

Gln Ala Glu Tyr Asp Arg Leu Lys Gln Gln His Glu His Lys Gly
    1820            1825                1830

Leu Ser Pro Leu Pro Ser Pro Pro Glu Met Met Pro Thr Ser Pro
    1835            1840                1845

Gln Ser Pro Arg Asp Ala Glu Leu Ile Ala Glu Ala Lys Leu Leu
    1850            1855                1860

Arg Gln His Lys Gly Arg Leu Glu Ala Arg Met Gln Ile Leu Glu
    1865            1870                1875

Asp His Asn Lys Gln Leu Glu Ser Gln Leu His Arg Leu Arg Gln
    1880            1885                1890

Leu Leu Glu Gln Pro Gln Ala Glu Ala Lys Val Asn Gly Thr Thr
    1895            1900                1905

Val Ser Ser Pro Ser Thr Ser Leu Gln Arg Ser Asp Ser Ser Gln
    1910            1915                1920

Pro Met Leu Leu Arg Val Val Gly Ser Gln Thr Ser Asp Ser Met
    1925            1930                1935

Gly Glu Glu Asp Leu Leu Ser Pro Pro Gln Asp Thr Ser Thr Gly
    1940            1945                1950

Leu Glu Glu Val Met Glu Gln Leu Asn Asn Ser Phe Pro Ser Ser
    1955            1960                1965

Arg Gly Arg Asn Thr Pro Gly Lys Pro Leu Gly Leu Trp Ala Leu
    1970            1975                1980

Lys Cys Leu Leu Tyr Leu Ala Phe Leu Phe Ile Gly Val Asn Cys
    1985            1990                1995

Lys Phe Thr Ile Val Phe Pro His Asn Gln Lys Gly Asn Trp Lys
```

-continued

```
                2000                2005                2010
Asn Val Pro Ser Asn Tyr His Tyr Cys Pro Ser Ser Ser Asp Leu
                2015                2020                2025

Asn Trp His Asn Asp Leu Ile Gly Thr Ala Leu Gln Val Lys Met
        2030                2035                2040

Pro Lys Ser His Lys Ala Ile Gln Ala Asp Gly Trp Met Cys His
        2045                2050                2055

Ala Ser Lys Trp Val Thr Thr Cys Asp Phe Arg Trp Tyr Gly Pro
        2060                2065                2070

Lys Tyr Ile Thr His Ser Ile Arg Ser Phe Thr Pro Ser Val Glu
        2075                2080                2085

Gln Cys Lys Glu Ser Ile Glu Gln Thr Lys Gln Gly Thr Trp Leu
        2090                2095                2100

Asn Pro Gly Phe Pro Pro Gln Ser Cys Gly Tyr Ala Thr Val Thr
        2105                2110                2115

Asp Ala Glu Ala Ala Ile Val Gln Val Thr Pro His His Val Leu
        2120                2125                2130

Val Asp Glu Tyr Thr Gly Glu Trp Val Asp Ser Gln Phe Ile Asn
        2135                2140                2145

Gly Lys Cys Ser Asn Asp Ile Cys Pro Thr Val His Asn Ser Thr
        2150                2155                2160

Thr Trp His Ser Asp Tyr Lys Val Lys Gly Leu Cys Asp Ser Asn
        2165                2170                2175

Leu Ile Ser Thr Asp Ile Thr Phe Phe Ser Glu Asp Gly Glu Leu
        2180                2185                2190

Ser Ser Leu Gly Lys Glu Gly Thr Gly Phe Arg Ser Asn Tyr Phe
        2195                2200                2205

Ala Tyr Glu Thr Gly Asp Lys Ala Cys Lys Met Gln Tyr Cys Lys
        2210                2215                2220

His Trp Gly Val Arg Leu Pro Ser Gly Val Trp Phe Glu Met Ala
        2225                2230                2235

Asp Lys Asp Leu Phe Ala Ala Arg Phe Pro Glu Cys Pro Glu
        2240                2245                2250

Gly Ser Ser Ile Ser Ala Pro Ser Gln Thr Ser Val Asp Val Ser
        2255                2260                2265

Leu Ile Gln Asp Val Glu Arg Ile Leu Asp Tyr Ser Leu Cys Gln
        2270                2275                2280

Glu Thr Trp Ser Lys Ile Arg Ala Gly Leu Pro Ile Ser Pro Val
        2285                2290                2295

Asp Leu Ser Tyr Leu Ala Pro Lys Asn Pro Gly Thr Gly Pro Val
        2300                2305                2310

Phe Thr Ile Ile Asn Gly Thr Leu Lys Tyr Phe Glu Thr Arg Tyr
        2315                2320                2325

Ile Arg Val Asp Ile Ala Ala Pro Ile Leu Ser Arg Met Val Gly
        2330                2335                2340

Met Ile Ser Gly Thr Thr Thr Glu Arg Glu Leu Trp Asp Asp Trp
        2345                2350                2355

Ala Pro Tyr Glu Asp Val Glu Ile Gly Pro Asn Gly Val Leu Arg
        2360                2365                2370

Thr Ser Leu Gly Tyr Lys Phe Pro Leu Tyr Met Ile Gly His Gly
        2375                2380                2385

Met Leu Asp Ser Asp Leu His Leu Ser Ser Lys Ala Gln Val Phe
        2390                2395                2400
```

Glu His Pro His Ile Gln Asp Ala Ala Ser Gln Leu Pro Asp Asp
    2405                2410                2415

Glu Thr Leu Phe Phe Gly Asp Thr Gly Leu Ser Lys Asn Pro Ile
    2420                2425                2430

Glu Phe Val Glu Gly Trp Phe Ser Ser Trp Lys Ser Ser Ile Ala
    2435                2440                2445

Ser Phe Phe Phe Ile Ile Gly Leu Ile Ile Gly Leu Phe Leu Val
    2450                2455                2460

Leu Arg Val Gly Ile Tyr Leu Cys Ile Lys Leu Lys His Thr Lys
    2465                2470                2475

Lys Arg Gln Ile Tyr Thr Asp Ile Glu Met Asn Arg Leu Gly Lys
    2480                2485                2490

<210> SEQ ID NO 9
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Pro Leu Gly Leu Trp Ala Leu
1               5

<210> SEQ ID NO 10
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
aattatgggc cgacaccat ggagtgcctt ttgtactta                             39

<210> SEQ ID NO 11
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
ctctacttgg ctgaacctcg ccggcggttt agg                                  33

<210> SEQ ID NO 12
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
ccgtcagcgg ccgccatgct ttggtgggaa gaagta                               36

<210> SEQ ID NO 13
<211> LENGTH: 30

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
tactctctcc tgtgttacca gctggagtac                                           30
```